(12) United States Patent
Debnath et al.

(10) Patent No.: US 7,314,889 B2
(45) Date of Patent: Jan. 1, 2008

(54) COMPOUNDS AND THEIR USE IN MEDICINE, PROCESS FOR THEIR PREPARATION AND PHARMACEUTICAL COMPOSITIONS CONTAINING THEM

(75) Inventors: Bhuniya Debnath, Hyderabad (IN); Saibal Kumar Das, Hyderabad (IN); Gurram Ranga Madhavan, Hyderabad (IN); Javed Iqbal, Hyderabad (IN); Ranjan Chakrabarti, Hyderabad (IN); Reeba Kannimel Vikramadithyan, Hyderabad (IN)

(73) Assignees: Dr. Reddy's Laboratories, Inc., Bridgewater, NJ (US); Dr. Reddy's Laboratories Limited, Hyderabad (IN)

( * ) Notice: Subject to any disclaimer, the term of this patent is extended or adjusted under 35 U.S.C. 154(b) by 0 days.

(21) Appl. No.: 10/306,898

(22) Filed: Nov. 27, 2002

(65) Prior Publication Data
US 2003/0229083 A1    Dec. 11, 2003

(30) Foreign Application Priority Data
Dec. 3, 2001 (IN) .......................... 971/MAS/2001

(51) Int. Cl.
*A61K 31/195* (2006.01)
*C07C 229/34* (2006.01)
(52) U.S. Cl. ...................... 514/562; 562/452
(58) Field of Classification Search ................ 562/452; 514/562
See application file for complete search history.

(56) References Cited

FOREIGN PATENT DOCUMENTS

| | | |
|---|---|---|
| EP | 1 216 980 A | 6/2002 |
| WO | 99 62870 A | 12/1999 |
| WO | 99 62871 A | 12/1999 |
| WO | 99 62872 A | 12/1999 |
| WO | WO 00/64888 | 11/2000 |
| WO | WO 01/25181 A1 | 4/2001 |
| WO | 01 40172 A | 6/2001 |

OTHER PUBLICATIONS

Concise Encyclopedia Chemistry (1993) Walter de Gruyter Berlin-New York.*
A. Maureen Rouhi, Chemical & Engineering News, Feb. 24, 2003, pp. 32-35.*
Obach R. S., Drug-drug interactions: An important negative attribute in drugs, Drugs of Today, 39(5), 301-38, (2003).*
P.M. Dhamasena, et al.: "The effect of electro-withdrawing . . . " Journal of Chemical Research (Miniprint), No. 8, 1994, pp. 1601-1611, XP008015283 Royal Society of Chemistry, Letchworth, GA p. 1604, compound 28.

* cited by examiner

Primary Examiner—Rebecca Anderson
(74) Attorney, Agent, or Firm—Robert Steve Thomas

(57) ABSTRACT

The present invention relates to novel antidiabetic, hypolipidemic, antiobesity and hypocholesterolemic compounds of formula (I),

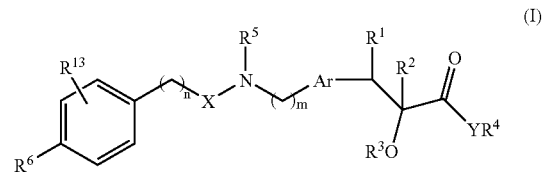

their derivatives, their analogs, their tautomeric forms, their stereoisomers, their polymorphs, their pharmaceutically acceptable salts, their pharmaceutically acceptable solvates and pharmaceutically acceptable compositions containing them.

14 Claims, No Drawings

COMPOUNDS AND THEIR USE IN MEDICINE, PROCESS FOR THEIR PREPARATION AND PHARMACEUTICAL COMPOSITIONS CONTAINING THEM

FIELD OF THE INVENTION

The present invention relates to novel antidiabetic, hypolipidemic, antiobesity and hypocholesterolemic compounds of formula (I), their derivatives, their analogs, their tautomeric forms, their stereoisomers, their polymorphs, their pharmaceutically acceptable salts, their pharmaceutically acceptable solvates and pharmaceutically acceptable compositions containing them.

More particularly, the present invention relates to compounds of the general formula (I) which are predominantly PPAR α agonists, their derivatives, their analogs, their tautomeric forms, their stereoisomers, their polymorphs, their pharmaceutically acceptable salts, their pharmaceutically acceptable solvates and pharmaceutically acceptable compositions containing them

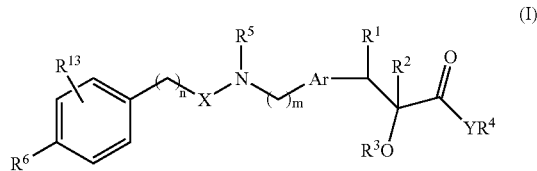

wherein $R^1$ represents hydrogen, hydroxy, halogen, linear or branched $(C_1$-$C_{12})$ alkyl, linear or branched $(C_1$-$C_{12})$ alkoxy, substituted or unsubstituted arylalkyl group or forms a bond together with the adjacent group $R^2$;

$R^2$ represents hydrogen; halogen, linear or branched $(C_1$-$C_{12})$ alkyl, linear or branched $(C_1$-$C_{12})$ alkoxy, $(C_1$-$C_{12})$ alkanoyl, aroyl, arylalkanoyl, substituted or unsubstituted arylalkyl or $R^2$ forms a bond together with $R^1$;

$R^3$ represents hydrogen atom or substituted or unsubstituted groups selected from linear or branched $(C_1$-$C_{12})$alkyl, cycloalkyl, cycloalkylalkyl, cycloalkenyl, aryl, $(C_1$-$C_{12})$alkanoyl, aroyl, arylalkyl, arylalkanoyl, heterocyclyl, heteroaryl, heteroarylalkyl, alkoxyalkyl, alkoxycarbonyl, aryloxycarbonyl, alkylaminocarbonyl, or arylaminocarbonyl groups;

$R^4$ represents hydrogen or substituted or unsubstituted groups selected from linear or branched $(C_1$-$C_{12})$ alkyl, cycloalkyl, aryl, arylalkyl, heterocyclyl, heteroaryl or heteroarylalkyl groups;

Y represents oxygen or $NR^7$ or $N(R^7)O$, where $R^7$ represents hydrogen or substituted or unsubstituted groups selected from linear or branched $(C_1$-$C_{12})$ alkyl, aryl, arylalkyl, hydroxyalkyl, alkanoyl, aroyl, arylalkanoyl, heterocyclyl, heteroaryl, heteroarylalkyl, alkoxycarbonyl or arylalkoxycarbonyl groups; $R^4$ and $R^7$ together may form a substituted or unsubstituted 5 or 6 membered cyclic structure containing carbon atoms, a nitrogen atom, which may optionally contain one or more additional heteroatoms selected from oxygen, sulfur or nitrogen;

$R^5$ represents hydrogen or substituted or unsubstituted groups selected from alkyl, alkenyl, cycloalkyl, cycloalkylalkyl, aryl, aroyl, aralkanoyl or arylalkyl group;

Ar represents substituted or unsubstituted groups selected from divalent phenylene, naphthylene, pyridyl, quinolinyl, benzofuryl, dihydrobenzofuryl, benzopyranyl, dihydrobenzopyranyl, indolyl, indolinyl, azaindolyl, azaindolinyl, pyrazolyl, benzothiazolyl, benzoxazolyl and the like.

X represents —C(=O)—, —C(=S)—, —C(=S)—O, —C(=O)—O—, —C(=O)—S—, —O—$(CH_2)_d$—, —NH—$(CH_2)_d$—, —O—C(=O)—, —C(O)$CH_2$—, —$CR^a$=$CR^b$—$CH_2$—; —$CR^a$=$CR^b$—CO— where $R^a$ and $R^b$ may be same or different and represent hydrogen or $(C_1$-$C_6)$alkyl, d is an integer of 1 to 4 or X represents a bond;

$R^6$ represents substituted or unsubstituted group selected from aryloxycarbonyl, arylalkoxycarbonyl, alkylcarbonyloxy, alkoxycarbonylamino, aryloxycarbonylamino, arylalkoxycarbonylamino, fluorenylmethoxycarbonyl (Fmoc), fluorenylmethoxycarbonylamino (N-Fmoc), —$OSO_2R^8$, —$OCONR^8R^9$, $NR^8COOR^9$, —$NR^8COR^9$, —$NR^8SO_2R^9$, $NR^8CONR^9R^{10}$, —$NR^8CSNR^8R^9$, —$SO_2R^8$, —$SOR^8$, —$SR^8$, —$SO_2NR^8R^9$, —$SO_2OR^8$, —$COOR^9$, —$COR^9$, or —$CONR^8R^9$, wherein $R^8$, $R^9$ and $R^{10}$ may be the same or different and independently represent hydrogen, or substituted or unsubstituted alkyl, aryl, arylalkyl, alkoxycarbonyl or arylalkoxycarbonyl; $R^8$ and $R^9$ when present on nitrogen atom together may form a 5 or 6 membered cyclic structure containing carbon atoms, a nitrogen atom and optionally one or more heteroatoms selected from oxygen, sulfur or nitrogen. $R^6$ is hydrogen, when $R^{13}$ is at the third position of the phenyl ring and does not represent hydrogen.

$R^{13}$ represents hydrogen, halogen, nitro, cyano, amino, haloalkyl, hydroxy or substituted or unsubstituted group selected from linear or branched $(C_1$-$C_{12})$ alkyl, aryl, arylalkyl, heteroaryl, heteroarylalkyl, heterocyclyl, alkoxy, monoalkylamino, dialkylamino, alkoxycarbonyl, aryloxycarbonyl, arylalkoxycarbonyl, aryloxy, arylalkoxy, alkylcarbonyloxy, alkoxycarbonylamino, aryloxycarbonylamino, arylalkoxycarbonylamino, fluorenylmethoxycarbonyl (Fmoc), fluorenylmethoxycarbonylamino (N-Fmoc), —$OSO_2R^8$, —$OCONR^8R^9$, $NR^8COOR^9$, —$NR^8COR^9$, —$NR^8R^9$, —$NR^8SO_2R^9$, $NR^8CONR^9R^{10}$, —$NR^8CSNR^8R^9$, —$SO_2R^8$, —$SOR^8$, —$SR^8$, —$SO_2NR^8R^9$, —$SO_2OR^8$, —$COOR^9$, —$COR^9$, —$CONR^8R^9$, wherein $R^8$, $R^9$ and $R^{10}$ may be same or different and independently represent hydrogen, or substituted or unsubstituted alkyl, aryl, arylalkyl, alkoxycarbonyl or arylalkoxycarbonyl; $R^8$ and $R^9$ when present on nitrogen atom together may form a 5 or 6 membered cyclic structure containing carbon atoms, a nitrogen atom and optionally one or more heteroatoms selected from oxygen, sulfur or nitrogen.

m is an integer from 0 to 6 and n is an integer from 0 to 6.

The present invention also relates to a process for the preparation of the above said compounds, their analogs, their derivatives, their tautomeric forms, their stereoisomers, their polymorphs, their pharmaceutically acceptable salts, their pharmaceutically acceptable solvates and pharmaceutical compositions containing them.

The present invention also relates to novel intermediates, processes for their preparation, their use in the preparation of compounds of formula (I) and their use as antidiabetic, hypolipidemic, antiobesity and hypocholesterolemic compounds.

The compounds of the present invention lower plasma glucose, triglycerides, insulin, lower total cholesterol (TC) and increase high density lipoprotein (HDL) and decrease low density lipoprotein (LDL) and very low density lipoprotein (VLDL), and $HBA_{1c}$, which have a beneficial effect on coronary artery disease and atherosclerosis.

The compounds of general formula (I) are useful in reducing body weight and for the treatment and/or prophylaxis of diseases such as atherosclerosis, stroke, peripheral vascular diseases and related disorders. These compounds are useful for the treatment of hyperlipidemia, hyperglycemia, hypercholesterolemia, lowering of atherogenic lipoproteins, VLDL (very low density lipoprotein) and LDL. The compounds of the present invention can be used for the treatment of renal diseases including glomerulonephritis, glomerulosclerosis, nephrotic syndrome, hypertensive, nephrosclerosis and nephropathy. The compounds of general formula (I) are also useful for the treatment and/or prophylaxis of leptin resistance, impaired glucose tolerance, disorders related to syndrome X such as hypertension, obesity, insulin resistance, atherosclerosis, coronary artery disease and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthoma, eating disorders, inflammation and for the treatment of cancer. The compounds of the present invention are also useful in the treatment and/or prophylaxis of the above said diseases in combination/concomittant with one or more of HMG CoA reductase inhibitor; cholesterol absorption inhibitor; anti-obesity drug; lipoprotein disorder treatment drug; hypoglycemic agent; insulin; biguamide; sulfonylurea; thiazolidinedione; dual PPARα and γ agonist or a mixture thereof.

BACKGROUND OF THE INVENTION

Atherosclerosis and other peripheral vascular diseases affect the quality of life of millions of people. Therefore, considerable attention has been directed towards understanding the etiology of hypercholesterolemia and hyperlipidemia and development of effective therapeutic strategies.

Hypercholesterolemia has been defined as plasma cholesterol level that exceeds arbitrarily defined value called "normal" level. Recently, it has been accepted that "ideal" plasma levels of cholesterol are much below the "normal" level of cholesterol in the general population and the risk of coronary artery disease (CAD) increases as cholesterol level rises above the "optimum" (or "ideal") value. There is clearly a definite cause and effect-relationship between hypercholesterolemia and CAD, particularly for individuals with multiple risk factors. Most of the cholesterol is present in the esterified forms with various lipoproteins such as Low density lipoprotein (LDL), Intermediate density lipoprotein (IDL), High density lipoprotein (HDL) and partially as Very low density lipoprotein (VLDL). Studies clearly indicate that there is an inverse correlationship between CAD and atherosclerosis with serum HDL-cholesterol concentrations (Stampfer et al., N. Engl. J. Med., 325 (1991), 373-381). The risk of CAD increases with increasing levels of LDL and VLDL.

In CAD, generally "fatty streaks" in carotid, coronary and cerebral arteries, are found which are primarily free and esterified cholesterol. Miller et al., (Br. Med. J., 282 (1981), 1741-1744) have shown that increase in HDL-particles may decrease the number of sites of stenosis in coronary arteries of human, and high level of HDL-cholesterol may protect against the progression of atherosclerosis. Picardo et al., Arteriosclerosis 6 (1986) 434-441 have shown by in vitro experiment that HDL is capable of removing cholesterol from cells. They suggest that HDL may deplete tissues of excess free cholesterol and transfer it to liver, which is known as reverse cholesterol transport, (Macikinnon et al., J. Biol. chem. 261 (1986), 2548-2552). Therefore, agents that increase HDL cholesterol would have therapeutic significance for the treatment of hypercholesterolemia and coronary heart diseases (CHD).

Obesity is a disease highly prevalent in affluent societies and in the developing world and is a major cause of morbidity and mortality. It is a state of excess body fat accumulation. The causes of obesity are unclear. It is believed to be of genetic origin or promoted by an interaction between the genotype and environment.

Irrespective of the cause, the result is fat deposition due to imbalance between the energy intake versus energy expenditure. Dieting, exercise and appetite suppression have been a part of obesity treatment. There is a need for efficient therapy to fight this disease since it may lead to coronary heart disease, diabetes, stroke, hyperlipidemia, gout, osteoarthritis, reduced fertility and many other psychological and social problems.

Diabetes and/or insulin resistance is yet another disease which severely effects the quality of large population in the world. Insulin resistance is the diminished ability of insulin to exert its biological action across a broad range of concentrations. In insulin resistance, the body secretes abnormally high amounts of insulin to compensate for this defect; failing which, the plasma glucose concentration inevitably raises and develops into diabetes. Among the developed countries, diabetes mellitus is a common problem and is associated with a variety of abnormalities including obesity, hypertension, hyperlipidemia (J. Clin. Invest., 75 (1985) 809-817; N. Engl. J. Med 317 (1987) 350-357; J. Clin. Endocrinol. Metab., 66 (1988) 580-583; J. Clin. Invest., 68 (1975) 957-969) and other renal complications (patent publication No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X.

Hyperlipidemia is the primary cause for cardiovascular (CVD) and other peripheral vascular diseases. High risk of CVD is related to the higher LDL (Low Density Lipoprotein) and VLDL (Very Low Density Lipoprotein) seen in hyperlipidemia. Patients having glucose intolerance/insulin resistance in addition to hyperlipidemia have higher risk of CVD. Numerous studies in the past have shown that lowering of plasma triglycerides and total cholesterol, in particular LDL and VLDL and increasing HDL cholesterol help in preventing cardiovascular diseases.

Peroxisome Proliferator Activated Receptors (PPARs) are orphan receptors belonging to the steroid/retinoid receptor super family of ligand activated transcription factors. (Wilson T. M. and Wahli W., Curr. Opin. Chem. Biol., 1997, Vol. 1, 235-241). Three mammalian Peroxisome Proliferator Activated Receptors (PPARs) have been isolated and termed PPAR-α, PPAR-γ and PPAR-δ. These PPARs regulate expression of target genes by binding to DNA sequence elements.

Certain compounds that activate or otherwise interact with one or more of the PPARs have been implicated in the regulation of triglyceride and cholesterol levels in animal models. (U.S. Pat. Nos. 5,847,008; 5,859,051 and PCT publications WO 97/28149; WO 99/04815.

A wealth of information exists on the influence of PPAR α agonists on the cardiovascular risk profile for example fibrate class of compounds which are weak PPAR-α agonists correct atherogenic dyslipoproteinemia. Several angiographic intervention trials have demonstrated a beneficial action of these drugs on atherosclerotic lesion progression and results from primary and secondary prevention trials show a decreased incidence of cardiovascular events. (Ricote M. and Glass C. K.; Trends in Pharmacological Sciences; 2001; 22(9); 441-443.

Despite the fact that fibrates, which are weak PPAR-α activators, reduce the plasma triglyceride levels and elevate the levels of HDL-C simultaneously, they are not the drugs of choice, because of: low efficacy requiring high doses, incidence of Myositis and contra-indicated in patients with impaired renal and hepatic function and in pregnant and nursing women.

However there has been rapid progress in the understanding of the role of PPAR-α in different pathophysiological conditions in addition to the well-documented favourable effects on lipid profile. The inflammatory activation of aortic smooth muscle cells, which is the hallmark of atherosclerosis, seems to be inhibited by the enhanced PPAR-α activity. (Vamecq J. and Latruffe N; Lancet; 1999; 354; 141-148).

Recent evidence suggests the role of PPAR-α receptors in improving insulin sensitivity. It has been demonsrated that by lowering circulatory and muscle lipids in insulin-resistant rodent models such as obese Zucker rats, high fat-fed mice and sucrose-lard fed rats, PPAR-α ligands improve insulin sensitivity and obesity. Further the lipid lowering activity of the statins has been linked to a cross talk with PPAR-α receptor in addition to limited cholesterol availability. Some clinical trials have shown improvement in insulin sensitivity indices, wherein fibrates were employed. (Guerre-Millo M, Rounalt C. and Poulain P; Diabetes; 2001; 50; 2809-2814, Muoio D. M., Way J. M. and Tanner C. J.; Diabetes; 2002; 51; 901-909, Ye J, Doyle P. J. and Iglesias M. A.; Diabetes; 2001; 50; 411-417, and Roglans N, Sanguino E. and Peris C; JPET; 2002; 302; 232-239).

Thus there is an interesting evidence for PPAR-(α agonists to be used for lipid control and as per recent evidence even for insulin resistance. Limitations of the currently available medications coupled with the fact that lipid abnormalities are on the rise worldover necessitate the discovery of more potent and safer PPAR-α agonists. In continuation of our research work on PPAR agonists (U.S. Pat. Nos. 5,885,997; 6,054,453; 6,265,401: PCT application PCT/IB02/04275) to address this unmet need, a series of compounds have been synthesized which has been disclosed in the present invention.

PRIOR ART

A few alkyl carboxylic acids, their derivatives and their analogs have been reported to be useful in the treatment of hyperglycemia and hypercholesterolemia. Some of such compounds described in the prior art are outlined below:

i) U.S. Pat. No. 5,306,726, WO 91/19702 discloses several 3-aryl-2-hydroxypropionic acid derivatives of general formulas (IIa) and (IIb) as hypolipidemic and hypoglycemic agents.

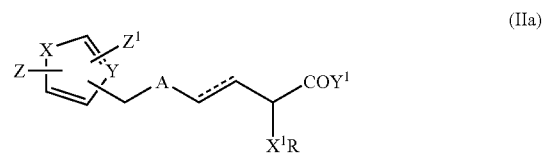

(IIa)

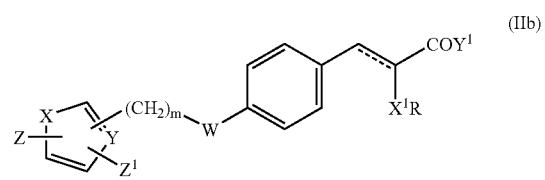

(IIb)

Examples of these compounds are shown in formulae (IIc) and (IId)

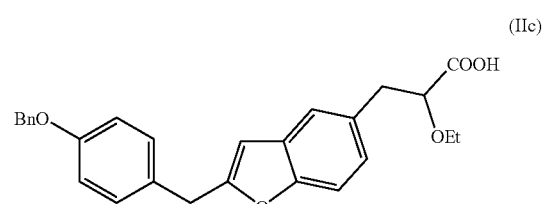

(IIc)

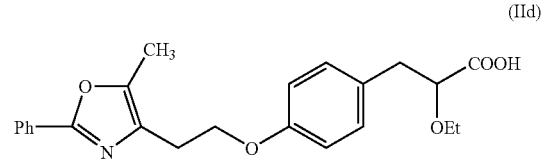

(IId)

ii) International publication Nos. WO 95/03038 and WO 96/04260 discloses compounds of formula (II e)

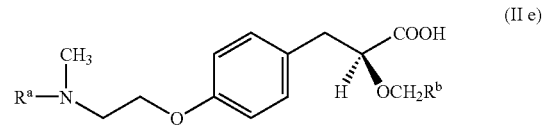

(II e)

An example of these compounds is shown in formula (II f)

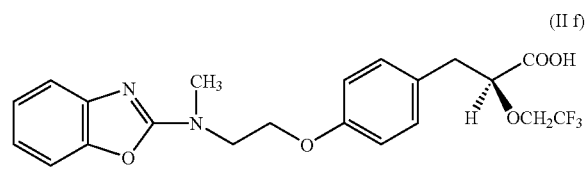

(II f)

iii) International publication Nos. WO 94/13650, WO 94/01420 and WO 95/17394 discloses the compounds of general formula (II g)

$A^1-X-(CH_2)_n-O-A^2-A3-Y.R^2$ (II g)

An example of these compounds is shown in formula (II h)

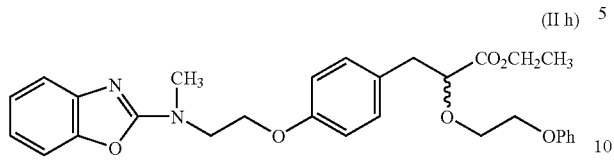

iv) International publication No. WO 00/49005 discloses the compounds of general formula (II i)

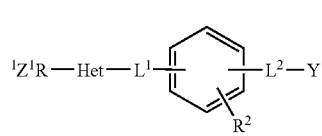

An example of these compounds is shown in formula (II j)

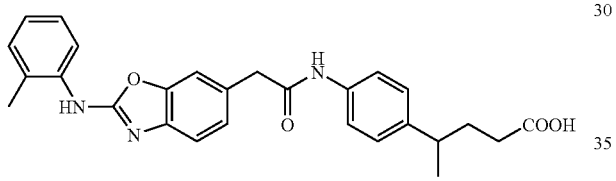

v) International publication No. WO 94/12181 discloses the compounds of general formula (II k)

X—Y-Z-Aryl-A-B (II k)

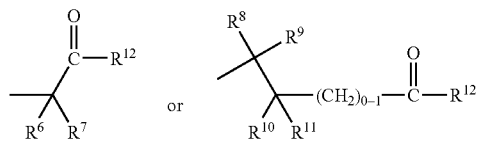

An example of these compounds is shown in formula (II l)

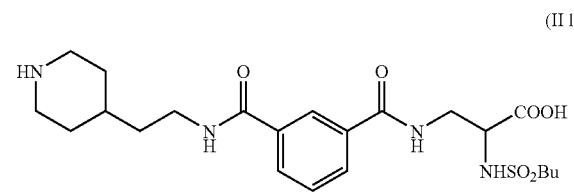

vi) International publication No. WO 93/16697 and U.S. Pat. No. 5,227,490 discloses the compounds of general formula (II m)

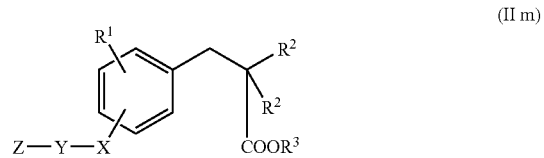

An example of these compounds is shown in formula (II n)

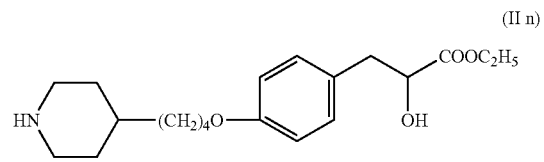

vii) International publication No. WO 99/62871 discloses the compounds of general formula (II o)

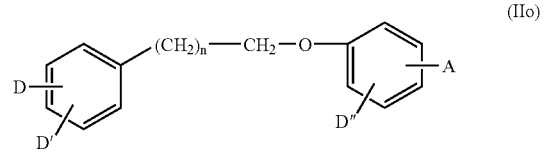

wherein A is situated in the ortho, meta or para position and represents

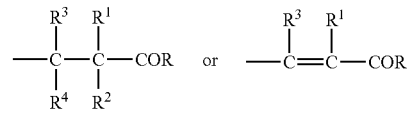

An example of these compounds is shown in formula (II p)

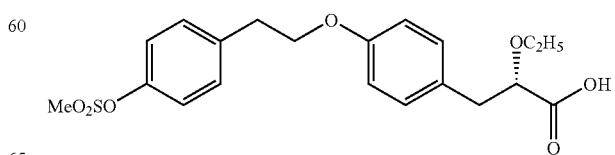

viii) International publication No. WO 00/64888 discloses the compounds of general formula (IIq)

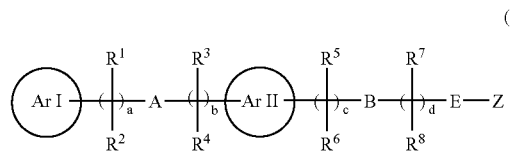
(IIq)

An example of these compounds is shown in formula (IIr)

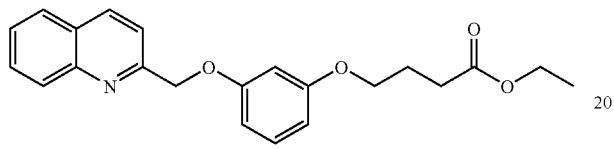
(IIr)

ix) International publication No. WO 99/62872 disclose the compounds of formula (IIs)

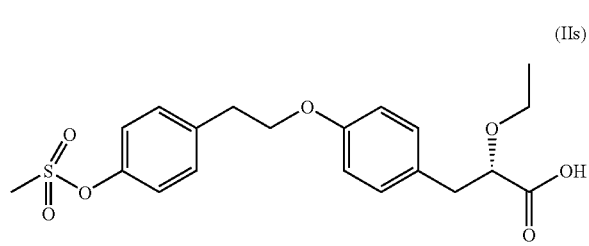
(IIs)

x) International publication No. WO 00/63153 discloses the compounds of formula (IIt)

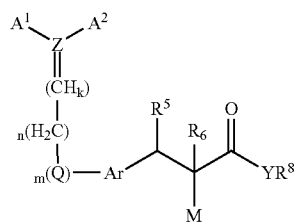
(IIt)

An example of these compounds is shown in formula (IIu)

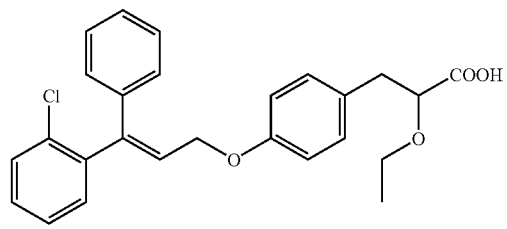
(IIu)

xi) International publication No. WO 01/55085 discloses the compounds of formula (IIv)

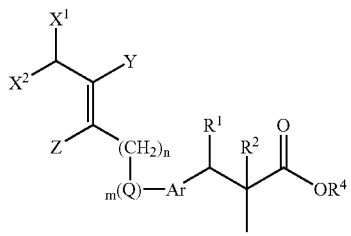
(IIv)

An example of these compounds is shown in formula (IIw)

(IIw)

Few β-phenyl α-hydroxysubstituted propionic acid derivatives have been reported which have been used as intermediates for the synthesis of target molecules.

Some of such compounds described in the prior art are outlined below:

i) European Patent Application EP0816316 discloses compound of formula (va)

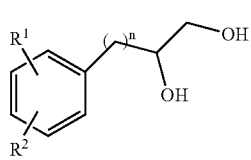
(va)

The compound of formula (va) was further converted to 1,2-ethanediaol derivative of the formula (vb)

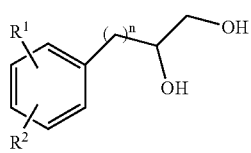
(vb)

These 1,2-ethanediaol derivatives are useful intermediates for the pharmaceuticals and agricultural chemicals.

ii) Japanese Patent Application JP 10017540 discloses compound of formula (vc)

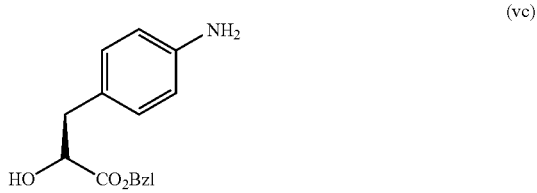

The compound of formula (vc) was further converted to a compound of formula (vd)

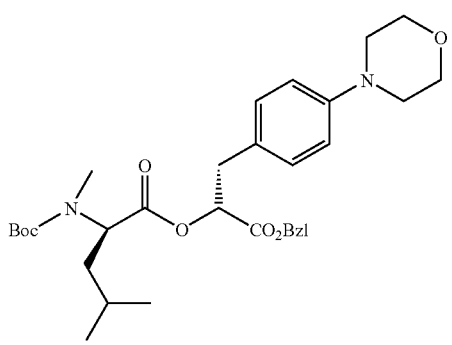

SUMMARY OF THE INVENTION

The objective of the present invention is to provide novel compounds of the general formula (I) having predominantly PPAR α agonistic activity with markedly reduced toxicities associated with PPAR γ activation for reducing blood glucose, lipid levels, lowering cholesterol and reducing body weight with beneficial effects in the treatment and/or prophylaxis of diseases related to increased levels of lipids, atherosclerosis, coronary artery diseases, Syndrome-X, impaired glucose tolerance, insulin resistance, insulin resistance leading to type 2 diabetes and diabetic complications thereof, for the treatment of diseases wherein insulin resistance is the pathophysiological mechanism and for the treatment of hypertension, with better efficacy, potency and lower toxicity, we focused our research to develop new compounds effective in the treatment of the above mentioned diseases. Effort in this direction has led to compounds having general formula (I).

The main aspect of the present invention is therefore, to provide novel alkyl carboxylic acids of the general formula (I), their derivatives, their analogs, their tautomeric forms, their stereoisomers, their polymorphs, their pharmaceutically acceptable salts, their pharmaceutically acceptable solvates and pharmaceutical compositions containing them, or their mixtures.

Another aspect of the present invention is to provide novel alkyl carboxylic acids, their derivatives, their analogs, their tautomeric forms, their stereoisomers, their polymorphs, their pharmaceutically acceptable salts, their pharmaceutically acceptable solvates and pharmaceutical compositions containing them or their mixtures which may have agonist activity against PPARα and/or PPARγ, and optionally inhibit HMG CoA reductase, in addition to having agonist activity against PPARα and/or PPARγ.

Yet another aspect of the present invention is to provide a process for the preparation of alkyl carboxylic acids of formula (I), their derivatives, their analogs, their tautomeric forms, their stereoisomers, their polymorphs, their pharmaceutically acceptable salts and their pharmaceutically acceptable solvates.

Still another aspect of the present invention is to provide pharmaceutical compositions containing compounds of the general formula (I), their analogs, their derivatives, their tautomers, their stereoisomers, their polymorphs, their salts, solvates or their mixtures in combination with suitable carriers, solvents, diluents and other media normally employed in preparing such compositions.

Another aspect of the present invention is to provide novel intermediates, a process for their preparation and use of the intermediates in processes for preparation of alkyl carboxylic acids of formula (I), their derivatives, their analogs, their tautomers, their stereoisomers and their use as antidiabetic, hypolipidemic, antiobesity and hypocholesterolemic compounds.

DETAILED DESCRIPTION OF THE INVENTION

Novel β-aryl α-oxysubstituted propanoic acids having the general formula (I)

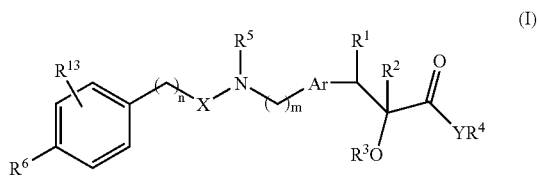

their derivatives, their analogs, their tautomeric forms, their stereoisomers, their polymorphs, their pharmaceutically acceptable salts, their pharmaceutically acceptable solvates wherein:

$R^1$ represents hydrogen, hydroxy, halogen, linear or branched ($C_1$-$C_{12}$) alkyl, linear or branched ($C_1$-$C_{12}$) alkoxy, substituted or unsubstituted arylalkyl group or forms a bond together with the adjacent group $R^2$;

$R^2$ represents hydrogen, halogen, linear or branched ($C_1$-$C_{12}$) alkyl, linear or branched ($C_1$-$C_{12}$) alkoxy, ($C_1$-$C_{12}$) alkanoyl, aroyl, arylalkanoyl, substituted or unsubstituted arylalkyl or $R^2$ forms a bond together with $R^1$;

$R^3$ represents hydrogen atom or substituted or unsubstituted groups selected from linear or branched ($C_1$-$C_{12}$)alkyl, cycloalkyl, cycloalkylalkyl, cycloalkenyl, aryl, ($C_1$-$C_{12}$)alkanoyl, aroyl, arylalkyl, arylalkanoyl, heterocyclyl, heteroaryl, heteroarylalkyl, alkoxyalkyl, alkoxycarbonyl, aryloxycarbonyl, alkylaminocarbonyl, or arylaminocarbonyl groups;

$R^4$ represents hydrogen or substituted or unsubstituted groups selected from linear or branched ($C_1$-$C_{12}$) alkyl, cycloalkyl, aryl, arylalkyl, heterocyclyl, heteroaryl or heteroarylalkyl groups;

Y represents oxygen, $NR^7$ or $N(R^7)O$, where $R^7$ represents hydrogen or substituted or unsubstituted groups selected from linear or branched ($C_1$-$C_{12}$) alkyl, aryl, arylalkyl, hydroxyalkyl, alkanoyl, aroyl, arylalkanoyl, heterocyclyl, heteroaryl, heteroarylalkyl, alkoxycarbonyl or arylalkoxycarbonyl groups; $R^4$ and $R^7$ together may form a substituted or unsubstituted 5 or 6 membered cyclic structure containing carbon atoms, a nitrogen atom, which may optionally contain one or more additional heteroatoms selected from oxygen, sulfur or nitrogen;

$R^5$ represents hydrogen or substituted or unsubstituted groups selected from alkyl, alkenyl, cycloalkyl, cycloalkylalkyl, aryl, aroyl, aralkanoyl or arylalkyl group;

n and m are integers ranging from 0-6;

Ar represents substituted or unsubstituted groups selected from divalent phenylene, naphthylene, pyridyl, quinolinyl, benzofuryl, dihydrobenzofuryl, benzopyranyl, dihydrobenzopyranyl, indolyl, indolinyl, azaindolyl, azaindolinyl, pyrazolyl, benzothiazolyl, benzoxazolyl and the like. The substituents on the group represented by Ar may be selected from linear or branched optionally halogenated $(C_1-C_6)$ alkyl, optionally halogenated $(C_1-C_3)$alkoxy, halogen, acyl such as acetyl, $COC_2H_5$, butanoyl, pentanoyl, propionyl, benzoyl and the like amino, acylamino, such as $NHCOCH_3$, $NHCOC_2H_5$, $NHCOC_3H_7$ and $NHCOC_6H_5$ and the like; thio or carboxylic or sulfonic acids and their derivatives. Derivatives of carboxylic acid and sulfonic acid include amides, chlorides, esters and anhydrides of carboxylic acid and sulfonic acid. X represents —C(=O)—, —C(=S)—, —C(=S)—O, —C(=O)—O—, —C(=O)—S—, —O—$(CH_2)_d$—, —NH—$(CH_2)_d$—, —O—C(=O)—, —C(O)$CH_2$—, —$CR^a$=$CR^b$—$CH_2$—; —$CR^a$=$CR^b$—CO— where $R^a$ and $R^b$ may be same or different and represent hydrogen or $(C_1-C_6)$alkyl; d is 1 to 4; or X represents a bond;

$R^{\neq}$ represents substituted or unsubstituted group selected from aryloxycarbonyl, arylalkoxycarbonyl, alkylcarbonyloxy, alkoxycarbonylamino, aryloxycarbonylamino, arylalkoxycarbonylamino, fluorenylmethoxycarbonyl (Fmoc), fluorenylmethoxycarbonylamino (N-Fmoc), —$OSO_2R^8$, —$OCONR^8R^9$, $NR^8COOR^9$, —$NR^8COR^9$, —$NR^8SO_2R^9$, $NR^8CONR^9R^{10}$, —$NR^8CSNR^8R^9$, —$SO_2R^8$, —$SOR^8$, —$SR^8$, —$SO_2NR^8R^9$, —$SO_2OR^8$, —$COOR^9$, —$COR^9$, —$CONR^8R^9$, wherein $R^8$, $R^9$ and $R^{10}$ may be same or different and independently represent hydrogen, or substituted or unsubstituted alkyl, aryl, arylalkyl, alkoxycarbonyl or arylalkoxycarbonyl; $R^8$ and $R^9$ when present on nitrogen atom together may form a 5 or 6 membered cyclic structure containing carbon atoms, nitrogen atom and optionally one or more heteroatoms selected from oxygen, sulfur or nitrogen. $R^6$ is hydrogen when $R^{13}$ is at the third position of the phenyl ring and does not represent hydrogen.

$R^{13}$ represents hydrogen, halogen, nitro, cyano, amino, haloalkyl, hydroxy or substituted or unsubstituted group selected from linear or branched $(C_1-C_{12})$ alkyl, aryl, arylalkyl, heteroaryl, heteroarylalkyl, heterocyclyl, alkoxy, monoalkylamino, dialkylamino, alkoxycarbonyl, aryloxycarbonyl, arylalkoxycarbonyl, aryloxy, arylalkoxy, alkylcarbonyloxy, alkoxycarbonylamino, aryloxycarbonylamino, arylalkoxycarbonylamino, fluorenylmethoxycarbonyl (Fmoc), fluorenylmethoxycarbonylamino (N-Fmoc), —$OSO_2R^8$, —$OCONR^8R^9$, $NR^8COOR^9$, —$NR^8COR^9$, —$NR^8R^9$, —$NR^8SO_2R^9$, $NR^8CONR^9R^{10}$, —$NR^8CSNR^8R^9$, —$SO_2R^8$, —$SOR^8$, —$SR^8$, —$SO_2NR^8R^9$, —$SO_2OR^8$, —$COOR^9$, —$COR^9$, —$CONR^8R^9$, wherein $R^8$, $R^9$ and $R^{10}$ may be same or different and independently represent hydrogen, or substituted or unsubstituted alkyl, aryl, arylalkyl, alkoxycarbonyl or arylalkoxycarbonyl; $R^8$ and $R^9$ when present on nitrogen atom together may form a 5 or 6 membered cyclic structure containing carbon atoms, nitrogen atom and optionally one or more heteroatoms selected from oxygen, sulfur or nitrogen.

Suitable groups represented by $R^1$ may be selected from hydrogen, hydroxy, halogen, linear or branched linear or branched $(C_1-C_{12})$ alkyl group, preferably, $(C_1-C_6)$alkyl groups such as methyl, ethyl, propyl, isopropyl or t-butyl; linear or branched $(C_1-C_{12})$ alkoxy, preferably linear or branched $(C_1-C_6)$alkoxy such as methoxy, ethoxy, propoxy, isopropoxy and the like; substituted or unsubstituted arylalkyl such as benzyl, phenethyl and the like or $R^1$ together with $R^2$ may form a bond. The arylalkyl may be substituted by $(C_1-C_6)$ alkyl, $(C_1-C_6)$ alkoxy or hydroxyl group.

Suitable groups represented by $R^2$ may be selected from hydrogen, halogen, linear or branched $(C_1-C_{12})$ alkyl, preferably linear or branched, $(C_1-C_6)$ alkyl groups such as methyl, ethyl, propyl, isopropyl or t-butyl; linear or branched $(C_1-C_{12})$ alkoxy, preferably linear or branched, $(C_1-C_6)$ alkoxy such as methoxy, ethoxy, propoxy, isopropoxy and the like; $(C_1-C_{12})$ alkanoyl such as acetyl, propanoyl, butanoyl, pentanoyl and the like; aroyl such as benzoyl and the like; arylalkanoyl such as phenyl acetyl, phenyl propanoyl and the like or substituted or unsubstituted arylalkyl such as benzyl, phenethyl and the like or $R^2$ together with $R^1$ may form a bond. The arylalkyl may be substituted by $(C_1-C_6)$ alkyl, $(C_1-C_6)$ alkoxy or hydroxyl group.

Suitable groups represented by $R^3$ may be selected from hydrogen, substituted or unsubstituted, linear or branched $(C_1-C_{12})$ alkyl group such as methyl, ethyl, n-propyl, isopropyl, n-butyl, isobutyl, t-butyl, pentyl, hexyl, heptyl, octyl and the like; substituted or unsubstituted $(C_1-C_{12})$alkanoyl group preferably a $(C_2-C_8)$ alkanoyl group such as acetyl, propanoyl, butanoyl, pentanoyl and the like; aroyl group such as benzoyl and the like, which may be substituted; arylalkanoyl group such as phenyl acetyl, phenyl propanoyl and the like, which may be substituted; $(C_3-C_7)$cycloalkyl group such as cyclopropyl, cyclobutyl, cyclopentyl, cyclohexyl, and the like, the cycloalkyl group may be substituted; $(C_3-C_7)$cycloalkylalkyl group such as cyclohexylmethyl, cyclohexylethyl, cyclohexylpropyl, cyclohexylbutyl and the like, which may be substituted; $(C_3-C_7)$ cycloalkenyl group such as cyclopropenyl, cyclobutenyl, cyclopentenyl, cyclohexenyl, and the like, the cycloalkenyl group may be substituted; aryl group such as phenyl, naphthyl and the like, the aryl group may be substituted; arylalkyl such as benzyl, phenethyl, $C_6H_5CH_2CH_2CH_2$, naphthylmethyl and the like, the arylalkyl group may be substituted; heterocyclyl group such as aziridinyl, pyrrolidinyl, piperidinyl and the like, the heterocyclyl group may be substituted; heteroaryl group such as pyridyl, thienyl, furyl and the like, the heteroaryl group may be substituted; heteroarylalkyl group such as furanmethyl, pyridinemethyl, oxazolemethyl, oxazoleethyl and the like, the heteroarylalkyl group may be substituted; $(C_1-C_6)$ alkoxy$(C_1-C_6)$alkyl group such as methoxymethyl, ethoxymethyl, methoxyethyl, ethoxypropyl and the like, the alkoxyalkyl group may be substituted; $(C_1-C_6)$ alkoxycarbonyl such as methoxycarbonyl, ethoxycarbonyl, propoxycarbonyl and the like, which may be substituted; aryloxycarbonyl such as phenoxycarbonyl, naphthyloxycarbonyl and the like, which may be substituted; $(C_1-C_6)$ alkylaminocarbonyl, such as methylaminocarbonyl, ethylaminocarbonyl, propylaminocarbonyl and the like, which may be substituted; and arylaminocarbonyl such as PhNHCO, naphthylaminocarbonyl and the like, which may be substituted. The substituents on the group represented by $R^3$ may be selected from halogen, hydroxy, cyano or nitro or substituted or unsubstituted groups selected from alkyl, cycloalkyl, alkoxy, cycloalkoxy such as cyclopropyloxy, cyclobutyloxy, cyclopentyloxy, cyclohexyloxy and like; arylalkoxyalkyl such as benzyloxy-$CH_2$—, benzyloxy-$CH_2$—$CH_2$, naphthyloxy-$CH_2$—, 2-phenethyloxy-$CH_2$— and the like; aryl, arylalkyl, heterocyclyl, heteroaryl, heteroarylalkyl, acyl, acyloxy such as OCOMe, OCOEt, OCOPh and the like; hydroxyalkyl, amino, acylamino such as $NHCOCH_3$, $NHCOC_2H_5$ and the like; arylamino such as $HNC_6H_5$, $NCH_3(C_6H_5)$, $NHC_6H_4CH_3$, $NHC_6H_4$-Hal and the like; aminoalkyl, aryloxy, alkoxycarbonyl, alkylamino, such as $NHCH_3$, $NHC_2H_5$, $NHC_3H_7$, $N(CH_3)_2$, $NCH_3(C_2H_5)$, $N(C_2H_5)_2$ and the like; alkoxyalkyl, alkylthio such as methylthio, ethylthio, propylthio, isopropylthio and the like; thioalkyl such as thiomethyl, thioethyl, thiopropyl and the like carboxylic acid or its derivatives, or sulfonic acid or its derivatives. Derivatives of carboxylic acid and sulfonic acid include amides, chlorides, esters and anydrides of carboxylic acid and sulfonic acid.

Suitable groups represented by $R^4$ may be selected from hydrogen, substituted or unsubstituted, linear or branched ($C_1$-$C_{12}$)alkyl group such as methyl, ethyl, n-propyl, isopropyl, n-butyl, iso-butyl, pentyl, hexyl, heptyl, octyl and the like; ($C_3$-$C_7$)cycloalkyl such as cyclopropyl, cyclopentyl, cyclohexyl and the like, the cycloalkyl group may be substituted; aryl group such as phenyl, naphthyl and the like, the aryl group may be substituted; arylalkyl group such as benzyl and phenethyl, the arylalkyl group may be substituted; heterocyclyl group such as aziridinyl, pyrrolidinyl, piperidinyl and the like, the heterocyclyl group may be substituted; heteroaryl group such as pyridyl, thienyl, furyl and the like, the heteroaryl group may be substituted; heteroarylalkyl group such as furanmethyl, pyridinemethyl, oxazolemethyl, oxazoleethyl and the like, the heteroarylalkyl group may be substituted. The substituents on the group represented by $R^4$ may be selected from halogen, hydroxy, cyano or nitro or substituted or unsubstituted groups selected from alkyl, cycloalkyl, alkoxy, cycloalkoxy such as cyclopropyloxy, cyclobutyloxy, cyclopentyloxy, cyclohexyloxy and like; arylalkoxyalkyl such as benzyloxy-$CH_2$—, benzyloxy-$CH_2$—$CH_2$, naphthyloxy-$CH_2$—, 2-phenethyloxy-$CH_2$— and the like; aryl, arylalkyl, heterocyclyl, heteroaryl, heteroarylalkyl, acyl, acyloxy such as OCOMe, OCOEt, OCOPh and the like; hydroxyalkyl, amino, acylamino such as $NHCOCH_3$, $NHCOC_2H_5$ and the like; arylamino such as $HNC_6H_5$, $NCH_3(C_6H_5)$, $NHC_6H_4CH_3$, $NHC_6H_4$-Hal and the like; aminoalkyl, aryloxy, alkoxycarbonyl, alkylamino, such as $NHCH_3$, $NHC_2H_5$, $NHC_3H_7$, $N(CH_3)_2$, $NCH_3(C_2H_5)$, $N(C_2H_5)_2$ and the like; alkoxyalkyl, alkylthio such as methylthio, ethylthio, propylthio, isopropylthio and the like; thioalkyl such as thiomethyl, thioethyl, thiopropyl and the like carboxylic acid or its derivatives, or sulfonic acid or its derivatives. Derivatives of carboxylic acid and sulfonic acid include amides, chlorides, esters and anydrides of carboxylic acid and sulfonic acid.

Suitable groups represented by $R^5$ may be selected from hydrogen, substituted or unsubstituted, linear or branched ($C_1$-$C_{16}$)alkyl, preferably ($C_1$-$C_{12}$)alkyl group such as methyl, ethyl, n-propyl, iso-propyl, n-butyl, iso-butyl, pentyl, hexyl, heptyl, octyl and the like; substituted or unsubstituted, linear or branched ($C_2$-$C_8$)alkenyl such as ethenyl, n-propenyl, n-butenyl, iso-butenyl, n-pentenyl, hexenyl, heptenyl and the like; ($C_3$-$C_7$)cycloalkyl group such as cyclopropyl, cyclobutyl, cyclopentyl, cyclohexyl, and the like, the cycloalkyl group may be substituted; ($C_3$-$C_7$)cycloalkyl ($C_1$-$C_{10}$)alkyl group such as cyclohexylmethyl, cyclohexylethyl, cyclohexylpropyl, cyclohexylbutyl and the like, which may be substituted; aryl group such as phenyl, naphthyl and the like, the aryl group may be substituted; aroyl group such as benzoyl and the like, the aroyl group may be substituted, arylalkanoyl such as phenyl acetyl, phenyl propanoyl and the like, which may be substituted; arylalkyl such as benzyl, phenethyl, $C_6H_5CH_2CH_2CH_2$, naphthylmethyl and the like, the arylalkyl group may be substituted. The substituents on the group represented by $R^5$ may be selected from halogen, hydroxy, nitro, alkyl, cycloalkyl, alkoxy, aryl, arylalkyl, arylalkoxyalkyl, such as $C_6H_5CH_2OCH_2$—, $C_6H_5CH_2OCH_2CH_2$—, $C_6H_5CH_2CH_2OCH_2CH_2$—, $C_6H_5CH_2CH_2OCH_2$— and the like; heterocyclyl, heteroaryl and amino.

Suitable groups represented by $R^6$ may be selected from unsubstituted or substituted aryloxycarbonyl group such as phenoxycarbonyl, naphthyloxycarbonyl and the like; arylalkoxycarbonyl group such as benzyloxycarbonyl, phenethyloxycarbonyl, naphthylmethoxycarbonyl and the like, which may be substituted; alkylcarbonyloxy group such as methylcarbonyloxy, ethylcarbonyloxy, propylcarbonyloxy and the like, which may be substituted; alkoxycarbonylamino group such as methoxycarbonylamino, ethoxycarbonylamino, propoxycarbonylamino, butoxycarbonylamino, t-butoxycarbonylamino and the like, which may be substituted; aryloxycarbonylamino group such as $NHCOOC_6H_5$, $N(CH_3)COOC_6H_5$, $N(C_2H_5)COOC_6H_5$, $NHCOOC_6H_4CH_3$, $NHCOOC_6H_4OCH_3$ and the like, which may be substituted; arylalkoxycarbonylamino group such as $NHCOOCH_2C_6H_5$, $NHCOOCH_2CH_2C_6H_5$, $N(CH_3)COOCH_2C_6H_5$, $N(C_2H_5)COOCH_2C_6H_5$, $NHCOOCH_2C_6H_4CH_3$, $NHCOOCH_2C_6H_4OCH_3$ and the like, which may be substituted; fluorenylmethoxycarbonyl (Fmoc), fluorenylmethoxycarbonylamino (N-Fmoc), —$OSO_2R^8$, —$OCONR^8R^9$, $NR^8COOR^9$, —$NR^8COR^9$, —$NR^8SO_2R^9$, $NR^8CONR^9R^{10}$, —$NR^8CSNR^8R^9$, —$SO_2R^8$, —$SOR^8$, —$SR^8$, —$SO_2NR^8R^9$, —$SO_2OR^8$, —$COOR^9$, —$COR^9$ or —$CONR^8R^9$. $R^6$ is hydrogen when $R^{13}$ is at the third position of the phenyl ring and does not represent hydrogen.

When the groups represented by $R^6$ are substituted, the substituents may be selected from halogen, hydroxy, nitro, alkyl, cycloalkyl, alkoxy, aryl, arylalkyl or amino.

Suitable groups represented by $R^{13}$ may be selected from hydrogen, halogen atom such as fluorine, chlorine, bromine or iodine; hydroxy, amino, nitro, cyano, or unsubstituted or substituted, linear or branched ($C_1$-$C_{12}$)alkyl group such as methyl, ethyl, n-propyl, isopropyl, n-butyl, isobutyl, t-butyl, pentyl, hexyl, heptyl, octyl and the like; haloalkyl like trifluoromethyl and the like; ($C_1$-$C_6$)alkoxy such as methoxy, ethoxy, propoxy and the like, which may be substituted; aryl group such as phenyl, naphthyl and the like, the aryl group may be substituted; arylalkyl such as benzyl, phenethyl, $C_6H_5CH_2CH_2CH_2$, naphthylmethyl and the like, the arylalkyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuranyl and the like, the heteroaryl group may be substituted; heteroarylalkyl groups such as furanmethyl, pyridinemethyl, oxazolemethyl, oxazoleethyl and the like, the heteroarylalky group may be substituted; heterocyclyl groups such as aziridinyl, pyrrolidinyl, morpholinyl, piperidinyl, piperazinyl and the like, the heterocyclyl group may be substituted; monoalkylamino group such as $NHCH_3$, $NHC_2H_5$, $NHC_3H_7$, $NHC_6H_{13}$ and the like, which may be substituted; dialkylamino group such as $N(CH_3)_2$, $NCH_3(C_2H_5)$, $N(C_2H_5)_2$ and the like, which may be substituted; alkoxycarbonyl such as methoxycarbonyl, ethoxycarbonyl, propoxycarbonyl, butoxycarbonyl, t-butoxycarbonyl and the like, which may be substituted; aryloxycarbonyl group such as phenoxycarbonyl, naphthyloxycarbonyl and the like, which may be substituted; arylalkoxycarbonyl group such as benzyloxycarbonyl, phenethyloxycarbonyl, naphthylmethoxycarbonyl and the like, which may be substituted; aryloxy group such as phenoxy, naphthyloxy and the like, the aryloxy group may be substituted; arylalkoxy group such as benzyloxy, phenethyloxy, naphthylmethyloxy, phenylpropyloxy and the like, the arylalkoxy group may be substituted; alkylcarbonyloxy group such as methylcarbonyloxy, ethylcarbonyloxy, propylcarbonyloxy and the like, which may be substituted; alkoxycarbonylamino group such as methoxycarbonylamino, ethoxycarbonylamino, propoxycarbonylamino, butoxycarbonylamino, t-butoxycarbonylamino and the like, which may be substituted; aryloxycarbonylamino group such as $NHCOOC_6H_5$, $N(CH_3)COOC_6H_5$, $N(C_2H_5)COOC_6H_5$, $NHCOOC_6H_4CH_3$, $NHCOOC_6H_4OCH_3$ and the like, which may be substituted; arylalkoxycarbonylamino group such as $NHCOOCH_2C_6H_5$, $NHCOOCH_2CH_2C_6H_5$, $N(CH_3)COOCH_2C_6H_5$, $N(C_2H_5)COOCH_2C_6H_5$, $NHCOOCH_2C_6H_4CH_3$, $NHCOOCH_2C_6H_4OCH_3$ and the like, which may be substituted; fluorenylmethoxycarbonyl (Fmoc), fluorenylmethoxycarbonylamino (N-Fmoc), $—OSO_2R^8$, $—OCONR^8R^9$, $NR^8COOR^9$, $—NR^8COR^9$, $—NR^8R^9$, $—NR^8SO_2R^9$, $NR^8CONR^9R^{10}$, $—NR^8CSNR^8R^9$, $—SO_2R^8$, $—SOR^8$, $—SR^8$, $—SO_2NR^8R^9$, $—SO_2OR^8$, $—COOR^9$, $—COR^9$, $—CONR^8R^9$.

When the groups represented by $R^{13}$ are substituted, the substituents may be selected from halogen, hydroxy, nitro, alkyl, cycloalkyl, alkoxy, aryl, arylalkyl or amino.

Suitable groups represented by $R^8$, $R^9$, $R^{10}$ may be selected from hydrogen, unsubstituted, linear or branched $(C_1-C_{12})$alkyl group such as methyl, ethyl, n-propyl, isopropyl, n-butyl, isobutyl, t-butyl, pentyl, hexyl, octyl and the like; aryl group such as phenyl, naphthyl and the like, the aryl group may be substituted; arylalkyl such as benzyl, phenethyl, $C_6H_5CH_2CH_2CH_2$, naphthylmethyl and the like, the arylalkyl group may be substituted; alkoxycarbonyl group such as t-butyloxycarbonyl (BOC) and the like; arylalkoxycarbonyl groups such as benzyloxycarbonyl (CBZ) and the like. $R^8$ and $R^9$ when present on nitrogen atom together may form 5 or 6 membered cyclic ring system containing carbon atoms, at least one nitrogen and optionally one or more hetero atoms selected from oxygen, sulfur or nitrogen, the cyclic ring system may contain one or two double bonds or it may be aromatic. The substituents on the groups represented by $R^8$, $R^9$ and $R^{10}$ may be selected from halogen, hydroxy, alkoxy, cyano, nitro, alkyl, cycloalkyl, aryl, arylalkyl, acyl, acyloxy, hydroxyalkyl, amino, aryloxy, alkylthio or thioalkyl groups.

Suitable groups represented by $R^7$ may be selected from hydrogen or substituted or unsubstituted, linear or branched $(C_1-C_2)$alkyl; aryl group such as phenyl, naphthyl and the like, the aryl group may be substituted; hydroxy$(C_1-C_6)$ alkyl, which may be substituted; arylalkyl group such as benzyl and phenethyl and the like, which may be substituted; heterocyclyl group such as aziridinyl, pyrrolidinyl, piperidinyl, and the like, which may be substituted; heteroaryl group such as pyridyl, thienyl, furyl and the like, which may be substituted; heteroarylalkyl group such as furamnethyl, pyridinemethyl, oxazolemethyl, oxazoleethyl and the like, which may be substituted; linear or branched $(C_2-C_8)$alkanoyl group such as acetyl, propanoyl, butanoyl, pentanoyl and the like, which may be substituted; aroyl group such as benzoyl and the like, which may be substituted; arylalkanoyl group such as phenyl acetyl, phenyl propanoyl and the like, which may be substituted; alkoxycarbonyl group such as t-butyloxycarbonyl and the like; arylalkoxycarbonyl groups such as benzyloxycarbonyl and the like. The substituents of the group represented by $R^7$ may be selected from halogen, hydroxy, alkoxy, cyano, nitro, alkyl, cycloalkyl, aryl, arylalkyl, acyl, acyloxy, hydroxyalkyl, amino, aryloxy, alkylthio or thioalkyl groups.

The substituents on the groups represented by $R^3$, $R^4$, $R^5$, $R^6$, $R^7$, $R^8$, $R^9$, $R^{10}$ and $R^{13}$ are as defined above.

Suitable ring structures formed by $R^4$ and $R^7$ together may be selected from pyrrolidinyl, piperidinyl, morpholinyl, piperazinyl, oxazolinyl and the like.

Suitable substituents on the cyclic structure formed by $R^4$ and $R^7$ taken together may be selected from hydroxy, alkyl, oxo, arylalkyl and the like.

Suitable groups represented by Ar may be selected from substituted or unsubstituted divalent phenylene, naphthylene, benzofuryl, indolyl, indolinyl, quinolinyl, azaindolyl, azaindolinyl, benzothiazolyl or benzoxazolyl groups, which may be unsubstituted or substituted by alkyl, haloalkyl, methoxy or haloalkoxy groups.

Suitable n and m are integers ranging from 0-6.

Suitable X represents $—C(=O)—$, $—O(CH_2)_d$, (where d is an integer from 1 to 4) $—C(=S)—$, $O—C(=O)—$, $—C(O)CH_2—$, $—CH=CH—CH_2—$; $—CH=CH—CO—$ or X represents a bond.

Preferred compounds of the present invention are those of formula (I) wherein:

$R^1$ is hydrogen, linear or branched $(C_1-C_6)$alkyl group or forms a bond with $R_2$.

$R^2$ is hydrogen, linear or branched $(C_1-C_6)$alkyl group or forms a bond with $R_1$.

$R^3$ is hydrogen, linear or branched $(C_1-C_{12})$alkyl, $(C_3-C_7)$ cycloalkyl group, aryl group such as phenyl, naphthyl or aryl alkyl group.

$R^4$ is hydrogen, linear or branched $(C_1-C_{12})$alkyl, $(C_3-C_7)$ cycloalkyl group, aryl group such as phenyl, naphthyl or aryl alkyl group.

$R^5$ is hydrogen, $(C_1-C_{12})$alkyl or $(C_3-C_7)$cycloalkyl group.

$R^6$ is fluorenylmethoxycarbonyl (Fmoc), fluorenylmethoxycarbonylamino (N-Fmoc), $—OSO_2R^8$, $—OCONR^8R^9$, $NR^8COOR^9$, $—NR^8COR^9$ or $—NR^8SO_2R^9$.

$R^8$ is hydrogen, linear or branched $(C_1-C_6)$alkyl or aryl group which may be substituted.

$R^9$ is hydrogen, linear or branched $(C_1-C_6)$alkyl, t-butyloxycarbonyl or benzyloxycarbonyl group.

$R^{13}$ is hydrogen.

X is $—C(=O)—$, $O—C(=O)—$, $—O(CH_2)_d$, (where d is an integer from 1 to 4) $—C(=S)—$, $—CH=CH—CH_2—$; $—CH=CH—CO—$ or X represents a bond.

Y is oxygen or $NR^7$.

$R^7$ is hydrogen, substituted or unsubstituted, linear or branched $(C_1-C_{12})$alkyl or; aryl group, the aryl group may be substituted;

d is an integer from 1-4.

m is an integer from 0 to 1.

n is an integer from 0 to 2.

Still more preferred compounds of the present invention are those of formula (I) wherein:

$R^1$ is hydrogen or forms a bond with $R_2$.

$R^2$ is hydrogen or forms a bond with $R_1$.

$R^3$ is hydrogen, linear or branched $(C_1-C_{12})$alkyl group.

$R^4$ is hydrogen, linear or branched $(C_1-C_{12})$alkyl group.

$R^5$ is hydrogen or $(C_1-C_{12})$alkyl group.

$R^6$ is $—OSO_2R^8$ or $—NR^8SO_2R^9$.

$R^8$ is or linear or branched $(C_1\text{-}C_6)$alkyl, or substituted aryl group wherein the substituent is linear or branched $(C_1\text{-}C_6)$alkyl group.

$R^9$ is linear or branched $(C_1\text{-}C_6)$alkyl, t-butyloxycarbonyl or benzyloxycarbonyl group.

$R^{13}$ is hydrogen.

X is —C(=O)—, O—C(=O)—, —O(CH$_2$)$_d$ (d is 1 to 4), —CH=CH—CH$_2$—; —CH=CH—CO— or X represents a bond.

Y is oxygen.

Pharmaceutically acceptable salts forming part of this invention include salts derived from inorganic bases such as Li, Na, K, Ca, Mg, Fe, Cu, Zn, Al, Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, theobromine, glycinol, valinol, diethylamine, triethylamine, trimethylamine, tripropylamine, tromethamine, adamentyl amine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, thiamine, aminopyrimidine, aminopyridine, purine, pyrimidine, spernidine, and the like; chiral bases like alkylphenylamine, phenyl glycinol and the like, salts of natural amino acids such as histidine, ornithine, lysine, arginine; unnatural amino acids such as D-isomers or substituted amino acids; salts of acidic amino acids such as aspartic acid, glutamic acid; guanidine, substituted guanidine wherein the substituents are selected from nitro, amino, alkyl, alkenyl, alkynyl, ammonium or substituted ammonium salts. Salts may include acid addition salts where appropriate which are sulphates, nitrates, phosphates, perchlorates, borates, hydrohalides (HCl, HBr, HI), acetates, tartrates, maleates, citrates, succinates, palmoates, methanesulfonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

According to a feature of the present invention, the compound of general formula (I) where $R^1$, $R^2$, $R^3$, $R^4$, $R^5$, $R^6$, $R^{13}$, X, Y, n, m and Ar are as defined earlier, can be prepared by any of the following routes shown in Scheme-I below.

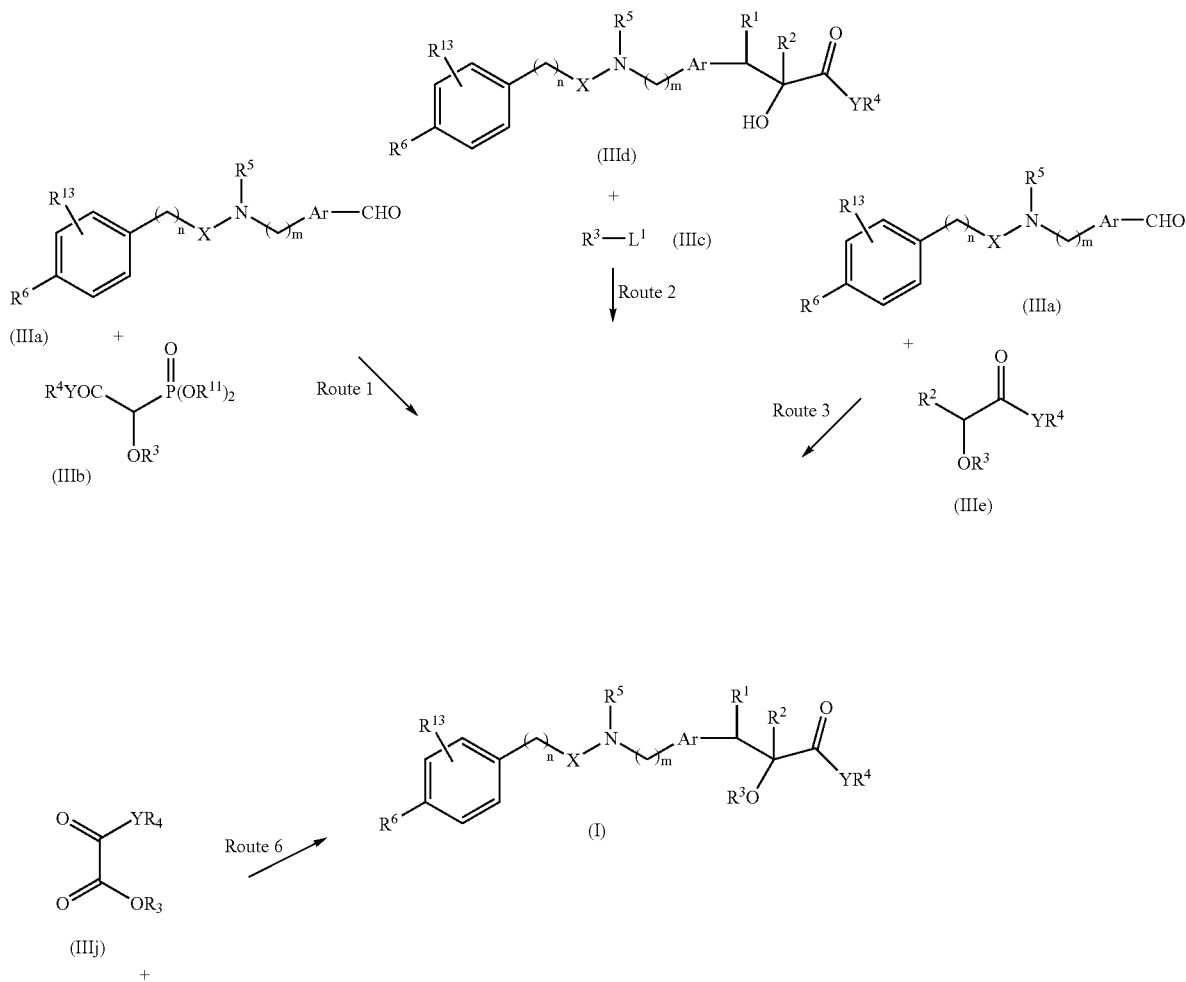

-continued

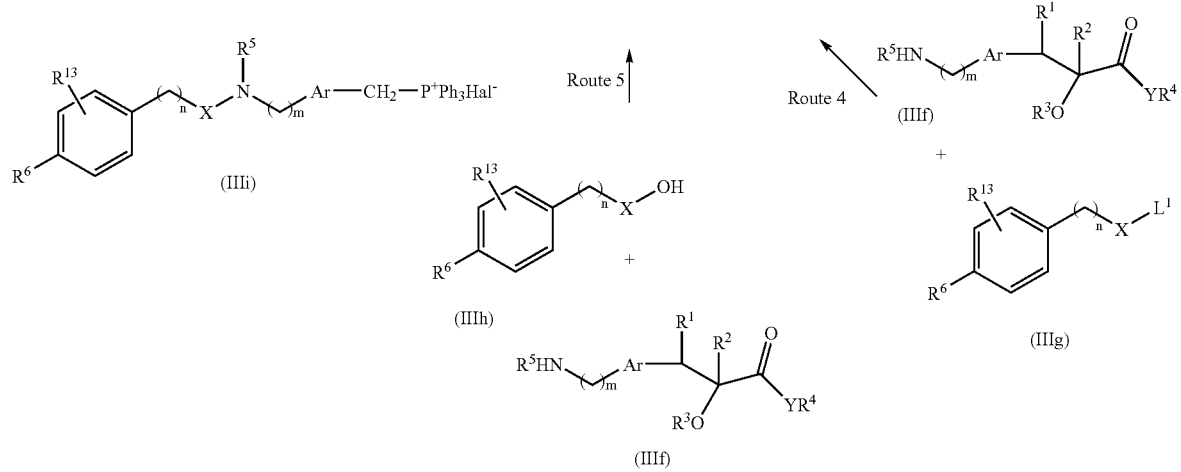

(IIIi)

(IIIh)

(IIIf)

(IIIg)

Route 1

The reaction of a compound of the general formula (IIIa) where all symbols are as defined earlier with a compound of formula (IIIb) where Y is as defined above excluding NH, $R^{11}$ represents linear or branched ($C_1$-$C_6$)alkyl and all other symbols are as defined earlier to yield compound of general formula (I) where Y is as defined above excluding NH and all other symbols are as defined above may be carried out in the presence of a base such as alkali metal hydrides like NaH or KH; organolithiums such as $CH_3Li$, BuLi, LDA, TMEDA and the like; alkoxides such as NaOMe, NaOEt, $K^+BuO^-$ and the like or mixtures thereof. The reaction may be carried out in the presence of solvents such as diethyl ether, THF, dioxane, DMF, DMSO, DME, toluene, benzene and the like or mixtures thereof. HMPA may be used as cosolvent. The reaction temperature may range from −78° to 50° C., preferably at a temperature in the range of −10° C. to 30° C. The reaction is more effective under anhydrous conditions. The compound of general formula (IIIb) may be prepared by Arbuzov reaction (*Annalen. Chemie*, 1996, 53, 699).

Alternatively, the compound of formula (I) may be prepared by reacting the compound of formula (IIIa) where all symbols are as defined earlier with Wittig reagents such as $Hal^-Ph_3P^+CH$—$(OR^3)CO_2R^4$ under similar reaction conditions as described above, where $R^3$ and $R^4$ are as defined above.

Route 2

The reaction of compound of formula (IIId) where $R^6$ is as defined earlier, $NR^8R^9$, Y is as defined above excluding NH and all other symbols are as defined above with a compound of formula (IIIc) where $R^3$ is as defined earlier excluding hydrogen and $L^1$ is a leaving group such as halogen atom, p-toluenesulfonate, methanesulfonate, trifluoromethanesulfonate and the like to yield compound of formula (I) may be carried out in the presence of solvents such as diethyl ether, THF, DMF, DMSO, DME, toluene, benzene and the like. The inert atmosphere may be maintained by using inert gases such as $N_2$, Ar, He and the like. The reaction may be effected in the presence of a base such as KOH, NaOH, NaOMe, t-BuO$^-$K$^+$, NaH, KH, LDA, NaHMDS, $K^2CO_3$, $Na_2CO_3$ and the like. Phase transfer catalyst such as tetraalkylammonium halides or hydroxides or bisulphates may be employed. The reaction temperature may range from −20° C. to 200° C., preferably at a temperature in the range of 0° to 150°. The duration of the reaction may range from 1 to 72 hours, preferably from 1 to 12 hours. The reaction may also be carried out using alkylating agents such as dialkylsulphates like diethyl sulphate or dimethyl sulphate; alkyl halides like methyl iodide, methyl bromide ethyl iodide, ethyl bromide and the like.

Route 3

The reaction of a compound of the general formula (IIIa) where all symbols are as defined earlier, with a compound of formula (IIIe) where $R^2$ represents hydrogen atom, Y is as defined above excluding NH and all other symbols are as defined earlier may be carried out in the presence of a base. The nature of the base is not critical. Any base normally employed for aldol condensation reaction may be employed; bases like metal hydride such as NaH, KH, metal alkoxides such as NaOMe, t-BuO$^-$K$^+$, NaOEt, metal amides such as $LiNH_2$, $LiN(ipr)_2$ may be used. Aprotic solvents such as THF, ether, dioxane may be used. The reaction may be carried out in an inert atmosphere, which may be maintained by using inert gases such as $N_2$, Ar, or He and the reaction is more effective under anhydrous conditions. Temperature in the range of −80° C. to 35° C. may be used. The β-hydroxy product initially produced may be dehydrated under conventional dehydration conditions such as treating with p-TSA in solvents such as benzene or toluene. The nature of solvent and dehydrating agent are not critical. Temperature in the range of 20° C. to reflux temperature of the solvent used may be employed, preferably at reflux temperature of the solvent by continuous removal of water using a Dean Stark water separator.

Route 4

The reaction of compound of formula (IIIg) where $R^6$, $R^{13}$, X, and n are as defined earlier and $L^1$ represents a leaving group such as halogen atom like chlorine or bromine or iodine, p-toluenesulfonate, methanesulfonate, trifluoromethanesulfonate and the like, preferably a halogen atom with compound of formula (IIIf) where $R^1$ and $R^2$ together represent a bond and all other symbols are as defined earlier to produce a compound of the formula (I) defined above may be carried out in the presence of aprotic solvents such as diethyl ether, THF, DMF, DMSO, DME, toluene, benzene, acetone, acetonitrile and the like or mixtures thereof. The reaction may be carried out in an inert atmosphere, which may be maintained by using inert gases such as $N_2$, Ar, He and the like. The reaction may be effected in the presence of a base such as $K_2CO_3$, $Na_2CO_3$ or NaH or mixtures thereof. The reaction temperature may range from −20° C.-120° C., preferably at a temperature in the range of 0° C.-120° C. The duration of the reaction may range from 1 to 48 hours. Phase transfer catalyst such as tetraalkylammonium halides or hydroxides or bisulphates may be employed.

Route 5

The reaction of compound of general formula (IIIh) where $R^6$, $R^{13}$, X, n are as defined earlier with a compound of general formula (IIIf) where $R^1$ and $R^2$ together represent a bond, $R^5$ is hydrogen and all other symbols are as defined earlier may be carried out using suitable coupling agents such as isobutyl chloroformate or ethyl chloroformate/$Et_3N$, pivaloyl chloride/$Et_3N$, dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbon tetrachloride and the like. The inert atmosphere may be maintained by using inert gases such as $N_2$, Ar, He and the like. The reaction may be effected in the presence of DMAP, HOBt and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 48 hours, preferably from 0.5 to 24 hours.

Route 6

The reaction of a compound of formula (IIIi) where all symbols are as defined earlier with a compound of formula (IIIj) where Y represents oxygen, $R^3=R^4$ and are as defined earlier excluding hydrogen, to produce a compound of the formula (I) where $R^1$ and $R^2$ together represent a bond, Y represents oxygen atom may be carried out neat in the presence of a base such as alkali metal hydrides like NaH, KR or organolithiums like $CH_3Li$, BuLi and the like or alkoxides such as NaOMe, NaOEt, t-BuO$^-$K$^+$ and the like or mixtures thereof. The reaction may be carried out in the presence of aprotic solvents such as THF, dioxane, DMF, DMSO, DME and the like or mixtures thereof. HMPA may be used as co-solvent. The reaction temperature may range from −78° to 100° C., preferably at a temperature in the range of −10° C. to 50° C. The duration of the reaction may range from 1 to 48 hours.

In yet another embodiment of the present invention, the compound of the general formula (I) where $R^1$ represents hydrogen atom, hydroxy, alkoxy, halogen, lower alkyl, substituted or unsubstituted arylalkyl group; $R^2$ represents hydrogen, halogen, lower alkyl, alkanoyl, aroyl, arylalkanoyl, substituted or unsubstituted arylalkyl; $R^3$, $R^4$, $R^5$, $R^6$, $R^{13}$, X, Y, Ar, m and n are as defined earlier can be prepared by one or more of the processes shown in Scheme-II below.

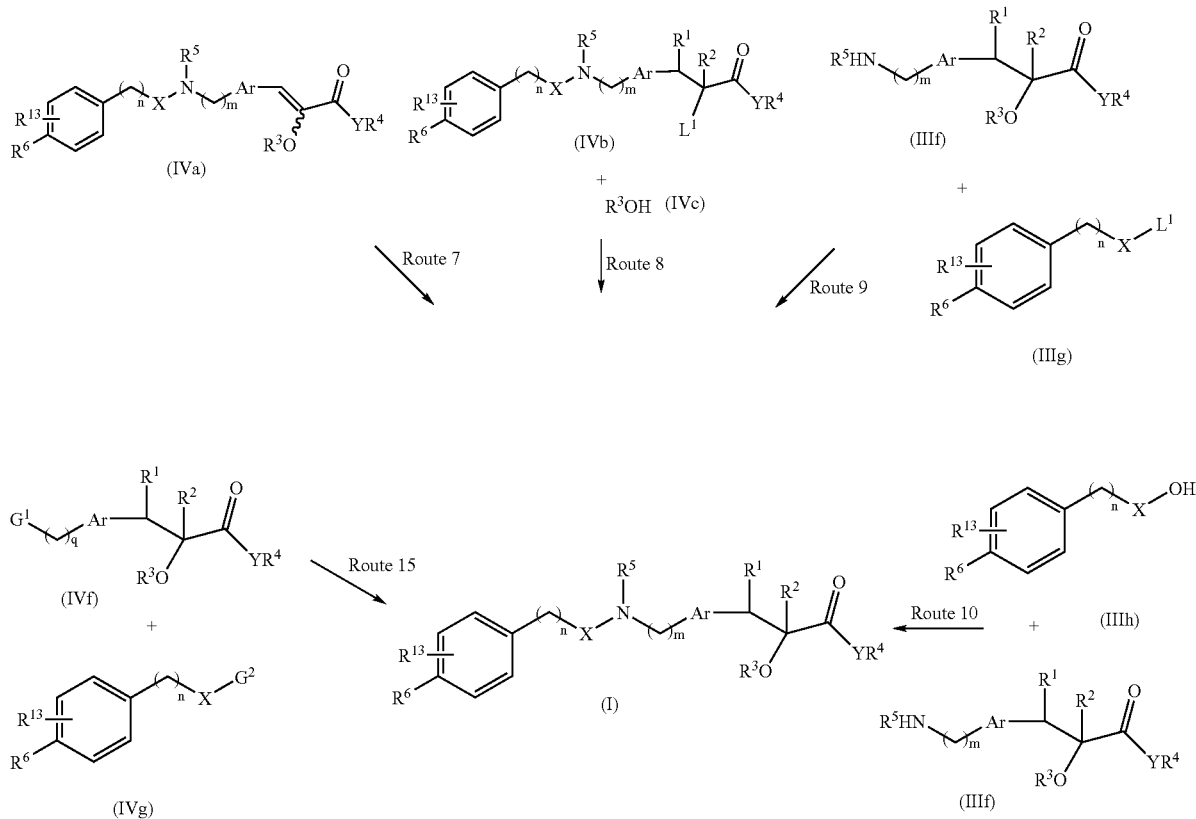

Scheme-II

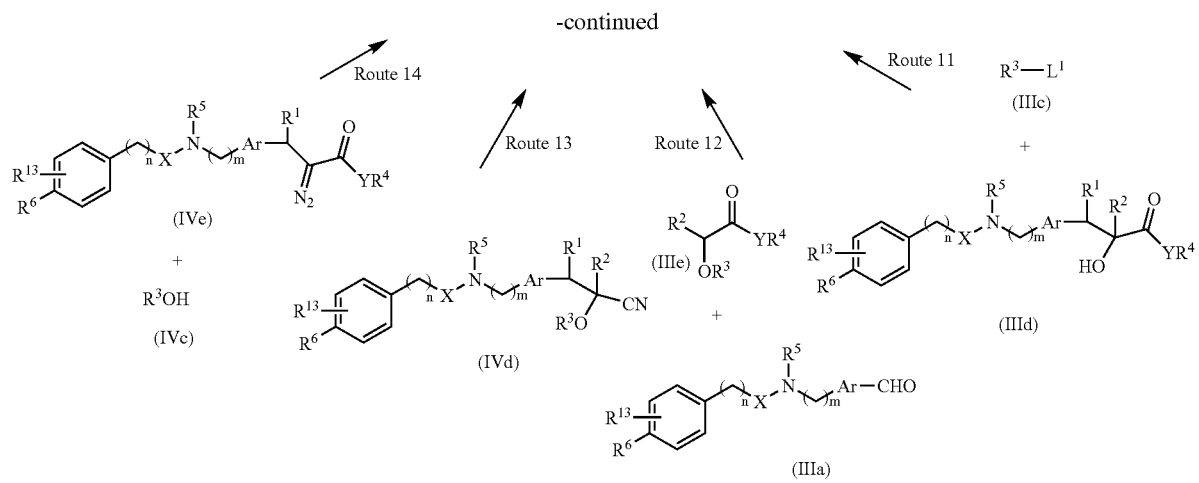

Route 7

The reduction of compound of the formula (IVa) which represents a compound of formula (I) where $R^1$ and $R^2$ together represent a bond and Y represent oxygen atom and all other symbols are as defined earlier, obtained as described earlier (Scheme-I), to yield a compound of the general formula (I) where $R^1$ and $R^2$ each represent hydrogen atom and all symbols are as defined earlier, may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate, alcohol such as methanol, ethanol and the like. A pressure between atmospheric pressure and 40 to 80 psi may be employed. The catalyst may be preferably 5-10% Pd/C and the amount of catalyst used may range from 5-100% w/w. The reaction may also be carried out by employing metal solvent reduction such as magnesium or samarium in alcohol or sodium amalgam in alcohol, preferably methanol. The hydrogenation may be carried out in the presence of metal catalysts containing chiral ligands to obtain a compound of formula (I) in optically active form. The metal catalyst may contain Rhodium, Ruthenium, Indium and the like. The chiral ligands may preferably be chiral phosphines such as optically pure enantiomers of 2,3-bis(diphenylphosphino)butane, 2,3-isopropylidene-2,3-dihydroxy-1,4-bis (diphenylphosphino)butane and the like. Any suitable chiral catalyst may be employed which would give required optical purity of the product (I) (Ref: Principles of Asymmetric Synthesis, Tetrahedron Series Vol 14, pp311-316, Ed. Baldwin J. E.).

Route 8

The reaction of compound of formula (IVb) where $R^6$ is as defined earlier; $R^4$ is as defined earlier excluding hydrogen and all other symbols are as defined earlier and $L^1$ is a leaving group such as halogen atom like chlorine, bromine or iodine; methane sulfonate, p-toluene sulfonate, trifluoromethane sulfonate with an alcohol of general formula (IVc), where $R^3$ is as defined earlier excluding hydrogen to produce a compound of the formula (I) defined earlier may be carried out in the presence of solvents such as diethyl ether, THF, DMF, DMSO, DME, diethyl ether, toluene, benzene and the like or mixtures thereof. The reaction may be carried out in an inert atmosphere, which may be maintained by using inert gases such as $N_2$, Ar, He and the like. The reaction may be effected in the presence of a base such as KOH, NaOH, NaOMe, NaOEt, t-BuO$^-$K$^+$, NaH, KH or mixtures thereof. Phase transfer catalysts such as tetraalkylammonium halides, bisulfates or hydroxides may be employed. The reaction temperature may range from $-20°$ C. to $120°$ C., preferably at a temperature in the range of $0°$ C. to $100°$ C. The duration of the reaction may range from 1 to 48 hours, preferably from 1 to 24 hours.

Route 9

The reaction of compound of formula (IIIg) defined earlier with compound of formula (IIIf) where all symbols are as defined earlier to produce a compound of the formula (I) defined above, may be carried out in the presence of solvents such as diethyl ether, THF, DMF, DMSO, DME, toluene, benzene, acetone, acetonitrile and the like or mixtures thereof. The reaction may be carried out in an inert atmosphere, which is maintained by using inert gases such as $N_2$, Ar, He and the like. The reaction may be effected in the presence of a base such as $K_2CO_3$, $Na_2CO_3$, NaH and the like or mixtures thereof. The reaction temperature may range from $-20°$ C. to $120°$ C., preferably at a temperature in the range of $0°$ C.-$120°$ C. The duration of the reaction may range from 1 to 48 hours, preferably from 1 to 24 hours. Phase transfer catalyst such as tetraalkylammonium halides or hydroxides may be employed.

Route 10

The reaction of compound of general formula (IIIh) defined earlier with a compound of general formula (IIIf) where all symbols are as defined above may be carried out using suitable coupling agents such as isobutyl chloroformate, ethyl chloroformate/Et$_3$N or pivaloyl chloride/Et$_3$N, dicyclohexyl urea, triarylphosphine/dialkylazadicarboxylate such as PPh$_3$/DEAD and the like. The reaction may be carried out in the presence of solvents such as THF, DME, CH$_2$Cl$_2$, CHCl$_3$, toluene, acetonitrile, carbon tetrachloride and the like. The inert atmosphere may be maintained by using inert gases such as $N_2$, Ar, He and the like. The reaction may be effected in the presence of DMAP, HOBt and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 48 hours, preferably from 6 to 24 hours.

Route 11

The reaction of compound of formula (IIId), which represents a compound of formula (I) where all symbols are as defined above, with a compound of formula (IIIc) where $R^3$ is as defined earlier excluding hydrogen and $L^1$ is a leaving group such as halogen atom like chlorine, bromine or iodine; methane sulfonate, p-toluene sulfonate, trifluoromethane sulfonate and like may be carried out in the presence of solvents such as diethyl ether, THF, DMF, DMSO, DME, toluene, benzene, acetone, acetonitrile and the like. The inert atmosphere may be maintained by using inert gases such as $N_2$, Ar, He and the like. The reaction may be effected in the presence of a base such as KOH, NaOH, NaOMe, t-BuO$^-$K$^+$, NaH, KH, LDA, NaHMDS, $K_2CO_3$, $Na_2CO_3$ and the like. Phase transfer catalyst such as tetraalkylammonium halides or hydroxides or bisulphates may be employed. The reaction temperature may range from −20° C. to 200° C., preferably at a temperature in the range of 0° to 150°. The duration of the reaction may range from 1 to 72 hours, preferably from 1 to 12 hours. The reaction may also be carried out using alkylating agents such as dialkylsulphates like diethyl sulphate or dimethyl sulphate; alkyl halides like methyl iodide, methyl bromide ethyl iodide, ethyl bromide and the like.

Route 12

The reaction of a compound of the general formula (IIIa) defined earlier with a compound of formula (IIIe) where $R^2$ represents hydrogen atom, Y is as defined above excluding NH and all other symbols are as defined earlier may be carried out under conventional conditions. Any base normally employed for aldol condensation reaction may be employed, metal hydride such as NaH or KH; metal alkoxides such as NaOMe, t-BuO$^-$K$^+$ or NaOEt; metal amides such as LiNH$_2$, LiN(iPr)$_2$. Aprotic solvent such as THF, DMF or diethyl ether may be used. Inert atmosphere may be employed such as argon and the reaction is more effective under anhydrous conditions. Temperature in the range of −80° C. to 25° C. may be used. The β-hydroxy aldol product may be dehydroxylated using conventional methods, conveniently by ionic hydrogenation technique such as by treating with a trialkylsilane in the presence of an acid such as trifluoroacetic acid. Solvent such as CH$_2$Cl$_2$ may be used. Favorably, reaction proceeds at 25° C. Higher temperature may be employed if the reaction is slow. Dehydroxylation may also be carried out using Barton's deoxygenation procedure (Ref. D. H. R. Barton et al *J. Chem. Soc., Perkin Trans I*, 1975, 1574; F. S. Martin et al *Tetrahedron Lett.*, 1992, 33, 1839).

Route 13

The conversion of compound of formula (IVd) where all symbols are as defined earlier to a compound of formula (I) where Y represents oxygen atom and all other symbols are as defined earlier may be carried out either in the presence of base or acid and the selection of base or acid is not critical. Any base normally used for hydrolysis of nitrile to acid may be employed, metal hydroxides such as NaOH or KOH in an aqueous solvent or any acid normally used for hydrolysis of nitrile to ester may be employed such as HCl in an excess of alcohol such as methanol, ethanol, propanol etc. The reaction may be carried out at a temperature in the range of 0° C. to reflux temperature of the solvent used, preferably at a temperature in the range of 25° C. to reflux temperature of the solvent used. The duration of the reaction may range from 0.25 to 48 hrs.

Route 14

The reaction of a compound of formula (IVe) where $R^4$ is as defined earlier excluding hydrogen and all symbols are as defined earlier with a compound of formula (IVc) where $R^3$ is as defined earlier excluding hydrogen to produce a compound of formula (I) (by a rhodium carbenoid mediated insertion reaction) may be carried out in the presence of rhodium (II) salts such as rhodium (II) acetate. The reaction may be carried out in the presence of solvents such as benzene, toluene, dioxane, ether, THF and the like or a combination thereof or when practicable in the presence of $R^3OH$ as solvent at any temperature providing a convenient rate of formation of the required product, generally at an elevated temperature, such as reflux temperature of the solvent. The inert atmosphere may be maintained by using inert gases such as $N_2$, Ar, He and the like. The duration of the reaction may range from 0.5 to 24 h, preferably from 0.5 to 6 h.

Route 15

The reaction of compound of formula (IVg) with compound of formula (IVf) where $G^1$ and $G^2$ are different and independently represent NH$_2$ or CHO, q is an integer ranging from 0-6 and all other symbols are as defined earlier to give a compound of formula (I) where $R^5$ represents hydrogen and all other symbols are as defined above may be carried out in two steps the first step being the imine formation, followed by reduction. Formation of imine may be carried out in solvents such as MeOH, EtOH, i-PrOH and the like. The reaction may be effected in the presence of a base such as NaOAc, KOAc and the like or the mixtures thereof. The temperature of reaction may range from room temperature to the reflux temperature of the solvent used. The reaction time may be 2 h to 24 h, preferably in the range 2 h to 12 h.

The imine can also be obtained by the reaction of a compound of general formula (IVg) with a compound of formula (IVf) where $G^1$ and $G^2$ are different and independently represent NH$_2$ or CHO, q is an integer ranging from 0-6 and all other symbols are as defined earlier using solvents such as CH$_2$Cl$_2$, CHCl$_3$, chlorobenzene, benzene, THF, in the presence of catalyst such as p-toluenesulfonic acid, methanesulfonic acid, TFA, TfOH, BF$_3$—OEt$_2$ and the like. The reaction may also be carried out in presence of activated molecular sieves. The temperature of the reaction may range from 10° C. to 100° C., preferably at a temperature in the range from 10° C. to 60° C. The reaction time may range from 1 h to 48 h.

The imine product thus obtained above may be reduced by using Na(CN)BH$_3$—HCl (ref: Hutchins, R. O. et al. *J. Org. Chem.* 1983, 48, 3433), NaBH$_4$, H$_2$—Pd]/C, H$_2$—Pt/C, H$_2$—Rh/C and the like in solvents such as methanol, ethanol and the like.

The compound of formula (I) where $R^5$ represents hydrogen, may also be prepared using single step procedure, using compound of formula (IVg) and (IVf) where all symbols are as defined earlier, by reductive amination using hydrogen as the reducing agent. The compounds of formulae (IVg) and (IVf) on condensation under pressure in the presence of hydrogen may give rise to the compound of formula (I). The pressure may vary from 10 to 90 psi, preferably between 20 and 60 psi. Solvents may be selected one from MeOH, EtOH, EtOAc, dioxane, toluene and the like. The temperature may range from RT to 50° C., preferably a range of RT to 40° C. The catalyst may be used such as Pd/C, Rh/C, Pt/C and the like.

The compound of general formula (I) where $R^4$ represents hydrogen atom may be prepared by hydrolysis using conventional methods, a compound of formula (I) where $R^4$ represents all groups defined earlier except hydrogen. The hydrolysis may be carried out in the presence of a base such as $Na_2CO_3$, $K_2CO_3$, NaOH, KOH, LiOH and the like and a suitable solvent such as methanol, ethanol, water and the like or mixtures thereof. The reaction may be carried out at a temperature in the range of 20-120° C. The reaction time may range from 2 to 48 h, preferably from 2 to 12 h.

The compound of general formula (I) where Y represents oxygen and $R^4$ represents hydrogen or lower alkyl group may be converted to compound of formula (I), where Y represents $NR^7$ by reaction with appropriate amines of the formula $NHR^4R^7$, where $R^4$ and $R^7$ are as defined earlier to yield a compound of formula (I) where Y represents $NR^7$ and all other symbols are as defined earlier. Alternatively, the compound of formula (I) where $YR^4$ represents OH may be converted to acid halide, preferably $YR^4$=Cl, by reacting with appropriate reagents such as oxalyl chloride, thionyl chloride and the like, followed by treatment with amines of the formula $NHR^4R^7$ where $R^4$ and $R^7$ are as defined earlier. Alternatively, mixed anhydrides may be prepared from compound of formula (I) where $YR^4$ represents OH and all other symbols are as defined earlier by treating with acid halides such acetyl chloride, acetyl bromide, pivaloyl chloride, dichlorobenzoyl chloride and the like. The reaction may be carried out in the presence of pyridine, triethylamine, diisopropyl ethylamine and the like. Coupling reagents such as DCC/DMAP DCC/HOBt, EDCI/HOBT, ethylchloroformate, isobutylchloroformate can also be used to activate the acid. Solvents such as halogenated hydrocarbons like $CHCl_3$ or $CH_2Cl_2$; hydrocarbons such as benzene, toluene, xylene and the like may be used. The reaction may be carried out at a temperature in the range of –40° C. to 40° C., preferably at a temperature in the range of 0° C. to 20°. The acid halide or mixed anhydride or activated acid obtained by coupling reagents described above thus prepared may further be treated with appropriate amines of the formula $NHR^4R^7$ where $R^4$ and $R^7$ are as defined earlier to yield a compound of formula (I) where Y represents $NR^7$ and all other symbols are as defined earlier.

Another embodiment of the present invention includes the novel intermediate of formula (IIIa)

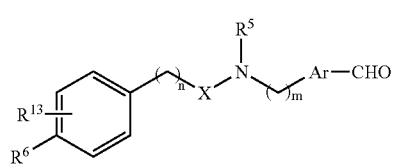

(IIIa)

its derivatives, its analogs, its tautomeric forms, its stereoisomers, its polymorphs, its pharmaceutically acceptable salts and its pharmaceutically acceptable solvates; wherein $R^5$ represents hydrogen or substituted unsubstituted group selected from alkyl, alkenyl, cycloalkyl, cycloalkylalkyl, aryl or arylalkyl group; n and m are integers ranging from 0-6; Ar represents substituted or unsubstituted groups selected from divalent phenylene, naphthylene, pyiidyl, quinolinyl, benzofuryl, dihydrobenzofuryl, benzopyranyl, dihydrobenzopyranyl, indolyl, indolinyl, azaindolyl, azaindolinyl, pyrazolyl, benzothiazolyl, benzoxazolyl and the like; X represents C=O, C=S, —C(O)CH$_2$—, —CH=CH—CH$_2$—; —CH=CH—CO— or X represents a bond; $R^6$ represents substituted or unsubstituted group selected from aryloxycarbonyl, arylalkoxycarbonyl, alkylcarbonyloxy, alkoxycarbonylamino, aryloxycarbonylamino, arylalkoxycarbonylamino, fluorenylmethoxycarbonyl (Fmoc), fluorenylmethoxycarbonylamino (N-Fmoc), —OSO$_2$R$^8$, —OCONR$^8$R$^9$, NR$^8$COOR$^9$, —NR$^8$COR$^9$, —NR$^8$SO$_2$R$^9$, NR$^8$CONR$^9$R$^{10}$, —NR$^8$CSNR$^8$R$^9$, —SO$_2$R$^8$, —SOR$^8$, —SR$^8$, —SO$_2$NR$^8$R$^9$, —SO$_{2O}$R$^8$, —COOR$^9$, —COR$^9$, or —CONR$^8$R$^9$, wherein R$^8$, R$^9$ and R$^{10}$ may be the same or different and independently represent hydrogen, or substituted or unsubstituted alkyl, aryl, arylalkyl, alkoxycarbonyl or arylalkoxycarbonyl; $R^8$ and $R^9$ when present on nitrogen atom together may form a 5 or 6 membered cyclic structure containing carbon atoms and one or more heteroatoms selected from oxygen, sulfur or nitrogen or $R^6$ is hydrogen; when $R^{13}$ is at the third position of the phenyl ring and does not represent hydrogen.

$R^{13}$ represents hydrogen, halogen, nitro, cyano, amino, haloalkyl, hydroxy or substituted or unsubstituted group selected from linear or branched (C$_1$-C$_{12}$)alkyl, aryl, arylalkyl, heteroaryl, heteroarylalkyl, heterocyclyl, alkoxy, monoalkylamino, dialkylamino, alkoxycarbonyl, aryloxycarbonyl, arylalkoxycarbonyl, aryloxy, arylalkoxy, alkylcarbonyloxy, alkoxycarbonylamino, aryloxycarbonylamino, arylalkoxycarbonylamino, fluorenylmethoxycarbonyl (Fmoc), fluorenylmethoxycarbonylamino (N-Fmoc), —OSO$_2$R$^8$, —OCONR$^8$R$^9$, NR$^8$COOR$^9$, —NR$^8$COR$^9$, —NR$^8$R$^9$, —NR$^8$SO$_2$R$^9$, NR$^8$CONR$^9$R$^{10}$, —NR$^8$CSNR$^8$R$^9$, —SO$_2$R$^8$, —SOR$^8$, —SR$^8$, —SO$_2$NR$^8$R$^9$, —SO$_2$OR$^8$, —COOR$^9$, —COR$^9$, —CONR$^8$R$^9$, wherein R$^8$, R$^9$ and R$^{10}$ may be same or different and independently represent hydrogen, or substituted or unsubstituted alkyl, aryl, arylalkyl, alkoxycarbonyl or arylalkoxycarbonyl; $R^8$ and $R^9$ when present on nitrogen atom together may form a 5 or 6 membered cyclic structure containing carbon atoms and one or more heteroatoms selected from oxygen, sulfur or nitrogen.

The substituents of the groups represented by Ar, $R^5$, $R^6$, $R^8$, $R^9$, $R^{10}$, and $R^{13}$ are as defined for the compound of formula (I).

m is an integer from 0 to 6 and n is an integer from 0 to 6.

In yet another embodiment of the present invention, the compound of formula (IIIa) where $R^5$ represents hydrogen; X represents C(O)CH$_2$—, —CH=CH—CH$_2$—; or X represents a bond; m is 0, Ar represents phenyl and all other symbols are as defined above may be prepared by following the process described in scheme-III below:

Scheme-III

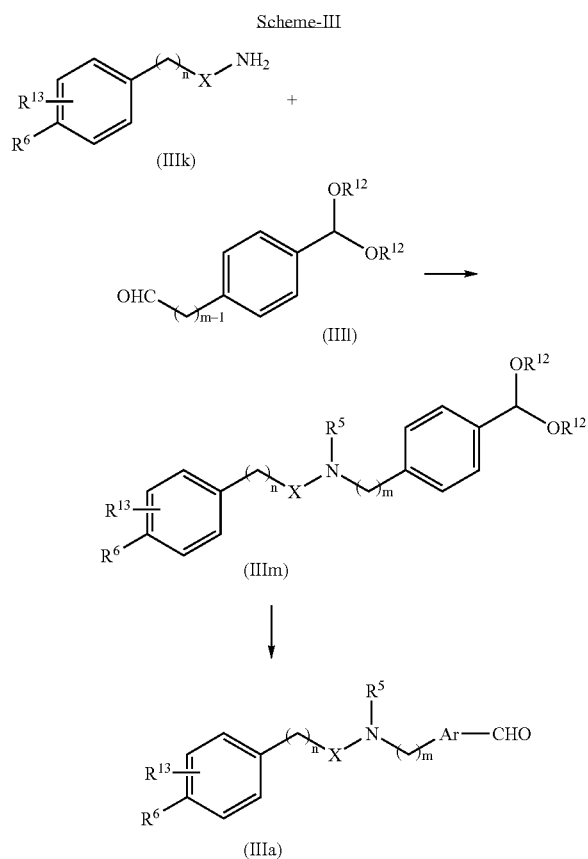

The reaction of compound of formula (IIIk) where all symbols are defined above with compound of formula (IIIl) where $R^{12}$ represents hydrogen or $(C_1$-$C_6)$alkyl group to give a compound of formula (IIIm) where all symbols are as defined earlier may be carried out in two steps the first step being the imine formation, followed by reduction. Formation of imine may be carried out in solvents such as MeOH, EtOH, i-PrOH and the like. The reaction may be effected in the presence of a promoter such as NaOAc, KOAc and the like or the mixtures thereof. The temperature of reaction may range from room temperature to the reflux temperature of the solvent used. The reaction time may be 2 h to 24 h, preferably in the range 2 h to 12 h.

The imine can also be obtained by the reaction of a compound of general formula (IIIk) with a compound of formula (IIIl) using solvents such as $CH_2Cl_2$, $CHCl_3$, chlorobenzene, benzene, THF, in the presence of catalyst such as p-toluenesulfonic acid, methanesulfonic acid, TFA, TfOH, $BF_3$—$OEt_2$ and the like. The reaction may also be carried out in presence of activated molecular sieves. The temperature of the reaction may range from 10° C. to 100° C., preferably at a temperature in the range from 10° C. to 60° C. The reaction time may be 1 h to 48 h.

The imine product thus obtained above may be reduced by using Na(CN)BH$_3$—HCl (ref: Hutchins, R. O. et al. *J. Org. Chem.* 1983, 48, 3433), NaBH$_4$, H$_2$—Pd]/C, H$_2$—Pt/C, H$_2$-Rh/C and the like in solvents such as methanol, ethanol and the like. The hydrolysis of compound of formula (IIIm) where all symbols are as defined earlier to produce compound of formula (IIIa) may be carried out either in the presence of base or acid and the selection of base or acid is not critical. Bases such as metal hydroxides like NaOH or KOH in an aqueous solvent or acids such as aqueous HCl or TFA in solvents such as $CH_2Cl_2$, THF, acetone, methanol, ethanol, propanol, water etc may be used. The reaction may be carried out at a temperature in the range of 0° C. to reflux temperature of the solvent used, preferably at a temperature in the range of 0° C. to reflux temperature of the solvent used. The duration of the reaction may range from 0.25 to 48 hrs.

In yet another embodiment of the present invention, the compound of formula (IIIa) where $R^5$ represents hydrogen or alkyl group; m is 0, and all other symbols are as defined above may be prepared by a process which comprises, reacting the compound of formula (IIIg)

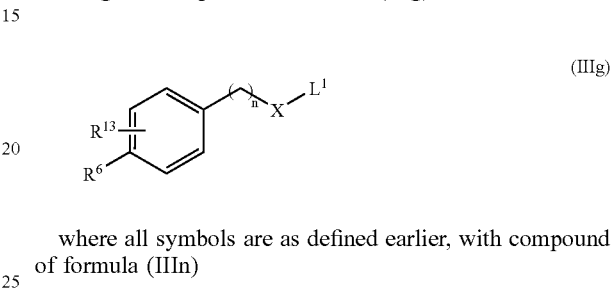

where all symbols are as defined earlier, with compound of formula (IIIn)

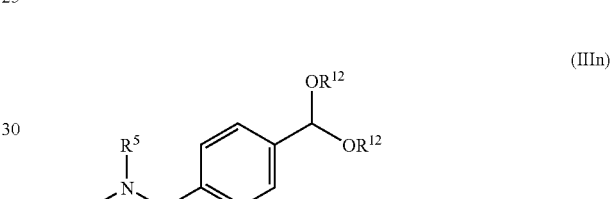

where $R^{12}$ represents hydrogen or alkyl group and $R^5$ is as defined above, m is an integer ranging form 0-6.

The reaction of compound of formula (IIIg) with compound of formula (IIIn) may be carried out in the presence of solvents such as THF, DMF, DMSO, DME, toluene, benzene, acetone, acetonitrile and the like or mixtures thereof. The reaction may be carried out in an inert atmosphere, which is maintained by using inert gases such as $N_2$, Ar, He and the like. The reaction may be effected in the presence of a base such as $K_2CO_3$, $Na_2CO_3$, NaH and the like or mixtures thereof. The reaction temperature may range from 20° C. to 120° C., preferably at a temperature in the range of 30° C.-80° C. The duration of the reaction may range from 1 to 24 hours, preferably from 1 to 12 hours.

Intermediate (IIIf) of the present invention and its process in our PCT application no. PCT/IB02/04275.

It is appreciated that in any of the above mentioned reactions, any reactive group in the substrate molecule may be protected according to conventional chemical practice. Suitable protecting groups in any of the above mentioned reactions are tertiarybutyldimethylsilyl, methoxymethyl, triphenyl methyl, benzyloxycarbonyl, THP etc, to protect hydroxyl or phenolic hydroxy group; N-Boc, N-Cbz, N-Fmoc, benzophenoneimine etc, for protection of amino or anilino group, acetal protection for aldehyde, ketal protection for ketone and the like. The methods of formation and removal of such protecting groups are those conventional methods appropriate to the molecule being protected.

The pharmaceutically acceptable salts are prepared by reacting the compound of formula (I) with 1 to 4 equivalents of a base such as sodium hydroxide, sodium methoxide, sodium hydride, potassium hydroxide, potassium t-butoxide, calcium hydroxide, magnesium hydroxide and the like, in solvents like ether, THF, methanol, t-butanol, dioxane, isopropanol, ethanol etc. Mixtures of solvents may be used. Organic bases like lysine, arginine, diethanolamine, choline, guanidine, tromethamine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, fumaric acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixtures of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) where $YR^{10}$ represents OH may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

Various polymorphs of a compound of general formula (I) forming part of this invention may be prepared by crystallization of compound of formula (I) under different conditions. For example, making use of commonly used solvents or their mixtures for recrystallization; crystallization at different temperatures; various modes of cooling, ranging from very fast to very slow cooling during crystallization. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The present invention provides a pharmaceutical composition, containing the compounds of the general formula (I) as defined above, their derivatives, their analogs, their tautomeric forms, their stereoisomers, their polymorphs, their pharmaceutically acceptable salts or their pharmaceutically acceptable solvates in combination with the usual pharmaceutically employed carriers, diluents and the like, useful for the treatment and/or prophylaxis of diseases such as hypertension, coronary artery disease, atherosclerosis, stroke, peripheral vascular diseases and related disorders.

These compounds are useful for the treatment of familial hypercholesterolemia, hypertriglyceridemia, lowering of atherogenic lipoproteins, VLDL and LDL, for reducing total cholesterol, body weight, blood plasma glucose, insulin, $HbA_{1C}$, triglycerides, or free fatty acids or increasing HDL in the plasma.

The compounds of this invention are useful in the prevention and/or treatment of diabetes caused by insulin resistance or impaired glucose tolerance. The compounds of the invention can be used to treat complications of diabetes. The complications include dyslipidemia, stroke, hyperlipidemia, hypercholesteremia, hyperglycemia, osteoporosis, obesity, atherosclerosis, leptin resistance, hypertension, obesity, insulin resistance, atherosclerosis, coronary artery disease, cardiovascular disorders; renal disease, glomerulonephritis, glomerulosclerosis, nephrotic syndrome, hypertensive nephrosclerosis, nephropathy; retinopathy, disorders to related endothelial cell activation, psoriasis, polycystic ovarian syndrome (PCOS), dementia, inflammatory bowel diseases, myotonic dystrophy, pancreatitis, arteriosclerosis, xanthoma, eating disorders, cancer or osteoporosis.

The compounds of the present invention can be used for the treatment of certain renal diseases including glomerulonephritis, glomerulosclerosis, nephrotic syndrome, hypertensive nephrosclerosis, nephropathy. The compounds of general formula (I) are also useful for the treatment/prophylaxis of insulin resistance (type II diabetes), leptin resistance, impaired glucose tolerance, dyslipidemia, disorders related to syndrome X such as hypertension, obesity, insulin resistance, coronary heart disease, and other cardiovascular disorders.

The compounds of the present invention may also be useful as aldose reductase inhibitors, for improving cognitive functions in dementia, as inflammatory agents, treating diabetic complications, disorders related to endothelial cell activation, psoriasis, polycystic ovarian syndrome (PCOS), inflammatory bowel diseases, osteoporosis, myotonic dystrophy, pancreatitis, retinopathy, arteriosclerosis, xanthoma and for the treatment of cancer.

The compounds of this invention can be used to for the treatment and/or prophylaxis of disorders related to Syndrome X such as hypertension, obesity, insulin resistance, atherosclerosis, coronary artery disease or cardiovascular disorder.

The compounds of the present invention are useful in the treatment and/or prophylaxis of the above said diseases in combination/concomittant with one or more HMG CoA reductase inhibitor; cholesterol absorption inhibitor; antiobesity drug; lipoprotein disorder treatment drug; hypoglycemic agents: insulin; biguamide; sulfonylurea; thiazolidinedione; dual PPARα and γ agonist or a mixture thereof. The compounds of the present invention in combination with HMG CoA reductase inhibitor, cholesterol absorption inhibitor, antiobesity drug, hypoglycemic agent can be administered together or within such a period to act synergistically.

The present invention also provides a pharmaceutical composition, containing the compounds of the general formula (I) as defined above, their derivatives, their analogs, their tautomeric forms, their stereoisomers, their polymorphs, their pharmaceutically acceptable salts or their pharmaceutically acceptable solvates and one or more HMG CoA reductase inhibitor; cholesterol absorption inhibitor; antiobesity drug; lipoprotein disorder treatment drug; hypoglycemic agents: insulin; biguamide; sulfonylurea; thiazolidinedione; dual PPARα and γ agonist or a mixture thereof in combination with the usual pharmaceutically employed carriers, diluents and the like.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active ingredient will be present in such pharmaceutical compositions in the amounts sufficient to provide the desired dosage in the range as described above. Thus, for oral administration, the compounds can be combined with a suitable solid, liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaeeutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

For nasal administration, the preparation may contain the compounds of the present invention dissolved or suspended in a liquid carrier, in particular an aqueous carrier, for aerosol application. The carrier may contain additives such as solubilizing agents, such as propylene glycol, surfactants, absorption enhancers such as lecithin (phosphatidylcholine) or cyclodextrin or preservatives such as parabenes.

Tablets, dragees or capsules having talc and/or a carbohydrate carried binder or the like are particularly suitable for any oral application. Preferably, carriers for tablets, dragees or capsules include lactose, corn starch and/or potato starch. A syrup or elixir can be used in cases where a sweetened vehicle can be employed. The compound(s) of the formula (I) as defined above is clinically administered to mammals, including man, via either oral or parenteral routes. Administration by the oral route is preferred being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 50 mg/kg body weight per day administered singly or as a divided dose. However, the optimum dosage for the individual subject being treated will be determined by the person responsible for treatment, generally smaller doses being administered initially and thereafter increments made to determine the most suitable dosage.

The compounds of the present invention lower random blood sugar level, triglyceride, total cholesterol, LDL, VLDL and increase HDL by agonistic mechanism. This may be demonstrated by in vitro as well as in vivo animal experiments.

The invention is explained in detail in the examples given below which are provided by way of illustration only and therefore should not be construed to limit the scope of the invention.

Preparation 1

4-(3-methanesulfonyloxypropyl)phenylmethanesulfonate

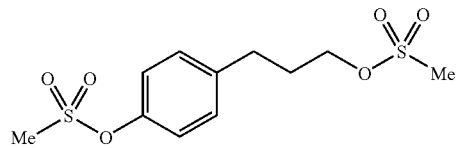

Step (i)

To a suspension of LAH (22.1 g, 2.5 eq, 583 mmol) in dry THF (1.0 L), was added dropwise a THF (50 mL) solution of methyl 3-(4-hydroxyphenyl)propionate (21 g, 1.0 eq, 116 mmol) at RT. The reaction mixture was refluxed for 4-5 h. It was worked up by quenching with excess ethyl acetate followed by addition of water (23 mL), 15% aq. NaOH (23 mL) and water (70 mL) under controlled stirring and maintaining RT. To the workup mixture conc. HCl was added to adjust the pH at 7.0. It was then filtered through celite and washed with ethyl acetate. Combined filtrate was dried ($Na_2SO_4$) and condensed. Obtained residue was chromatographed (ethyl acetate/hexanes) to obtain 3-(4-hydroxyphenyl)propanol (17 g, 100%) as white solid.

Mp: 52-54° C.

$^1$H NMR (CDCl$_3$, 200 MHz δ: 1.78-1.86 (m, 2H); 2.63 (t, J=7.9 Hz, 2H); 3.67 (t, J=6.3 Hz, 2H); 6.74 (d, J=8.8 Hz, 2H); 7.05 (d, J=8.8 Hz, 2H).

IR (neat) cm$^{-1}$: 3485, 3029, 2940, 1505.

Mass m/z (CI): 152 [M+1].

Step (ii)

To a DCM (550 mL) solution of 3-(4-hydroxyphenyl)propanol (17 g, 1.0 eq, 111.8 mmol), obtained in the step (i) and triethylamine (93.3 mL, 6.0 eq, 670.8 mmol) was added methanesulfonyl chloride (26 mL, 3.0 eq, 335.4 mmol) dropwise at 0° C. The reaction mixture was stirred at RT for 16 h, after that it was worked up by diluting with excess DCM and washing the organic layer with dil. HCl, water and brine. The organic layer was dried ($Na_2SO_4$) and concentrated. Desired product from the crude mass was purified by recrystallization from diisopropylether. The remaining mother liquor was condensed and was chromatographed (ethyl acetate/hexanes) to obtain further amount desired compound (total yield 20.8 g, 61%) as white solid.

Mp: 60-62° C.

$^1$H NMR (CDCl$_3$, 200 MHz: δ 2.00-2.18 (m, 2H); 2.77 (t, J=7.8 Hz, 2H); 3.00 (s, 3H); 3.13 (s, 3H); 4.23 (t, J=6.3 Hz, 2H); 7.22 (aromatics, 4H).

IR (neat) cm$^{-1}$: 3029, 2935, 1504.

Mass m/z (CI): 309 [M+1].

Preparation 2

3-(3-methanesulfonyloxypropyl)phenylmethanesulfonate

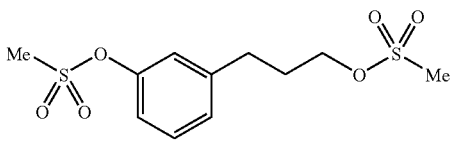

Prepared Following the Typical Procedure of Preparation 1

Step (i)

From methyl 3-hydroxyphenylpropionate; 3-(3-hydroxyphenyl)propanol was obtained as liquid mass (100%).

$^1$H NMR (CDCl$_3$, 200 MHz: δ 1.80-1.88 (m, 2H); 2.64 (t, J=7.9 Hz, 2H); 3.49 (bs, —OH); 3.67 (t, J=6.5 Hz, 2H); 6.65-6.76 (aromatics, 3H); 7.09-7.17 (aromatics, 1H).

IR (neat) cm$^{-1}$: 3353, 2932, 2859, 1590.

Mass m/z (CI): 152 [M+1].

Step (ii)

From 3-(3-hydroxyphenyl)propanol (900 mg, 1.0 eq, 5.92 mmol), obtained in the step (i); 3-(3-methanesulfonyloxypropyl)phenylmethanesulfonate was obtained (52%) as white solid.

Mp: 60-62° C.

$^1$H NMR (CDCl$_3$, 200 MHz: δ 2.00-2.18 (m, 2H); 2.79 (t, J=7.8 Hz, 2H); 3.00 (s, 3H); 3.15 (s, 3H); 4.22 (t, J=6.4 Hz, 2H); 7.10-7.20 (aromatics, 3H); 7.21-7.40 (m, 1H).

IR (neat) cm$^{-1}$: 3030, 2941, 1586.

Mass m/z (CI): 309 [M+1].

Preparation 3

4-(3-(toluene-4-sulfonyloxy)propyl)phenyltoluene-4-sulfonate

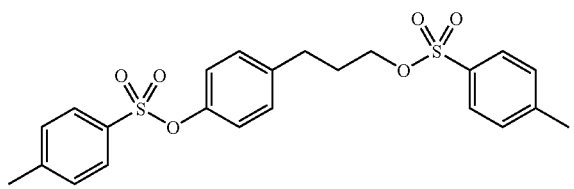

To a solution of 3-(4-hydroxyphenyl)propanol (2.5 g, 1.0 eq, 16.44 mmol), obtained in the step (i) of preparation 1 in DCM (82 mL) and triethylamine (11.4 mL, 5.0 eq, 82.2 mmol), was added toluene-4-sulfonylchloride (9.4 g, 3.0 eq, 49.3 mmol) dropwise at 0° C. The reaction mixture was stirred at RT for 16 h, after that it was worked up by diluting with excess DCM and washing the organic layer with water and brine. The crude residue obtained after drying (Na$_2$SO$_4$) and condensing was chromatographed (ethyl acetate/hexanes) to obtain the desired compound (5.1 g, 67.7%) as thick liquid.

$^1$H NMR (CDCl$_3$, 200 MHz: δ 1.90 (quintet, J=7.9 Hz, 2H); 2.44 (s, 6H); 2.61 (t, J=6.8 Hz, 2H); 3.98 (t, J=6.3 Hz, 2H); 6.83 (d, J=8.8 Hz, 2H); 6.97 (d, J=8.8 Hz, 2H); 7.32 (t, J=7.5 Hz, 2H); 7.67 (d, J=8.3 Hz, 2H); 7.76 (d, J=8.3 Hz, 2H).

IR (neat) cm$^{-1}$: 2926, 1597, 1502, 1364.

Mass m/z (CI): 461 [M+1].

Preparation 4

2-(4-nitrophenoxy)ethlbromide

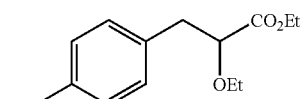

A mixture of 4-nitrophenol (1.0 g, 1.0 eq., 7.19 mmol), 1,2-dibromoethane (3.85 mL, 6.0 eq, 43.1 mmol), and anhydrous K$_2$CO$_3$ (3.0 g, 3 eq, 21.5 mmol) in dry acetone (36 mL) was stirred at RT for 16 h. The reaction mixture was filtered, and the filtrate was condensed. Condensed mass was again dissolved in ethyl acetate and washed with aq. sodium bicarbonate solution. Organic layer was dried (Na$_2$SO$_4$), condensed, and the residue was chromatographed using ethyl acetate and hexanes to obtain the title compound as solid (540 mg, 32%).

Mp: 168° C.

$^1$H NMR (CDCl$_3$, 200 MHz): δ 3.67 (t, J=6.1 Hz, 2H); 4.38 (t, J=6.1 Hz, 2H); 6.97 (d, J=8.7 Hz, 2H); 8.20 (d, J=8.7 Hz, 2H).

IR (neat) cm$^{-1}$: 2925, 1592, 1511, 1330.

Mass m/z (CI): 245[M($^{79}$Br)], 246 [M($^{79}$Br)+1], 247[M($^{81}$Br)], 248 [M($^{81}$Br)+1].

Preparation 5

Ethyl 2-ethoxy-3-(4-aminophenyl)propionate

Step (i)

Wittig salt from triethyl 2-ethoxyphosphonoacetate (26.5 g, 1.5 eq, 99.3 mmol) and NaH (50% in oil) (5.3 g, 2 eq, 132.4 mmol) was prepared in THF (350 mL) at 0° C. To this solid 4-nitrobenzaldehyde (10 g, 1 eq, 66.2 mmol) was added in portions at 0° C. and the resulting solution was stirred at RT for 16 h. The reaction mixture was diluted with ethyl acetate and washed with aqueous NH$_4$Cl. The crude contains ethyl p-nitro-2-ethoxycinnamate in both Z and E stereoisomers (11 g).

Step (ii)

Ethyl p-nitro-2-ethoxycinnamate obtained in step (i) was hydrogenated using 10% Pd—C—H$_2$ (60 psi) (11 g) in ethyl acetate (150 mL) at room temperature and chromatographed using ethyl acetate/hexane to yield the title compound as viscous oil (9.41 g, 60%).

$^1$H NMR (CDCl$_3$, 200 MHz): δ 1.16 (t, J=7.0 Hz, 3H), 1.22 (t, J=7.0 Hz, 3H), 2.90 (d, J=6.3 Hz, 2H), 3.30 (bs, 2H, NH2), 3.35 (m, 11H), 3.55 (m, 1H), 3.94 (t, J=6.3 Hz, 1H), 4.15 (q, J=7.0 Hz, 2H), 6.62 (d, J=8.3 Hz, 2H), 7.03 (d, J=8.0 Hz, 2H).

IR (neat) cm$^{-1}$: 3372, 1738.
Mass m/z (CI): 238 (M+1), 192 (M-OC$_2$H$_5$).

Preparation 6

Methyl 2-ethoxy-3-(4-aminophenyl)propionate

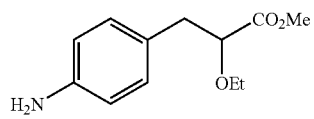

Step (i)

Wittig salt from triethyl 2-ethoxyphosphonoacetate (34.3 ml, 2 eq, 132 mmol) and NaH (50% in oil) (6.28 g, 2 eq, 132 mmol) was prepared in THF (350 mL) at 0° C. To this solid p-nitrobenzaldehyde (10 g, 1 eq, 66 mmol) was added in portions at 0° C. The resulting solution was stirred at RT for 16 h. The reaction mixture was diluted with ethyl acetate and washed with aqueous NH$_4$Cl. The crude contains ethyl p-nitro-2-ethoxycinnamate in both Z and E stereoisomers (15 g, 86%).

Step (ii)

The crude compound (15 g, 1 eq, 56.6 mmol) obtained in step (i) was dissolved in methanol (250 mL). To this ammonium formate (35.6 g, 10 eq, 566 mmol) and 10% Pd-C (40 g) was added and the reaction mixture was stirred at RT for 16 h. The catalyst was filtered off and the filterate was condensed on rotavapour. The residue was diluted with ethyl acetate and washed with water and brine. The crude mass was chromatographed to yield ethyl 2-ethoxyp-amino cinnamate as (E) and (Z) isomers (10 g, 75%).

Step (iii)

Ethyl 2-ethoxy p-amino cinnamate (10 g, 1 eq, 42.5 mmol) obtained in step (ii) was treated with magnesium (20.4 g, 20 eq, 850 mmol) and dry methanol (500 mL). The reaction mixture was refluxed for 2-3 h, and allowed to stir at room temperature for 16 h. The reaction mixture was diluted with ethyl acetate and quenched with cold aqueous ammonium chloride. The organic layer was washed with water and brine. The residue was chromatographed using ethyl acetate and hexane to afford the title compound as viscous liquid (8.06 g, 80%).

$^1$H NMR (200 MHz, CDCl$_3$): δ 1.64 (t, J=6.8 Hz, 3H), 2.90 (d, J=6.3 Hz, 2H), 3.22-3.42 (m, 1H), 3.42-3.65 (m, 2H), 3.70 (s, 3H), 3.96 (t, J=6.8 Hz, 1H), 6.61 (d, J=8.3 Hz, 2H); 7.00 (d, J=8.3 Hz, 2H);

IR (neat) cm$^{-1}$: 3350 (br), 1735.
Mass m/z (CI): 224 [M+1].

Preparation 7

Ethyl 2-ethoxy-3-(4-aminophenyl)propionate

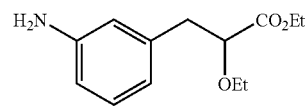

Starting from 3-nitro benzaldehyde and following the typical procedure for preparation of 5 the title compound was obtained as thick oil (60% two step).

$^1$NMR (200 MHz, CDCl$_3$): δ 1.17 (t, J=7 Hz, 3H); 1.22 (t, J=7 Hz, 3H); 2.91 (d, J=6.7 Hz, 2H); 3.30-3.48 (m, 1H); 3.48-3.62 (m, 1H); 4.00 (t, J=6.7 Hz, 1H); 4.17 (q, J=7 Hz, 2H); 6.50-6.70 (aromatics, 3H); 7.06 (t, J=7.5 Hz, 1H).

IR (neat) cm$^{-1}$: 3374, 2978, 1738, 1606.
Mass m/z (CI): 238 [M+1]

Preparation 8

Ethyl 2-isopropoxy-3-(4-nitrophenyl)propionate

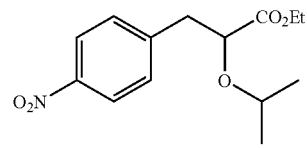

Step (i)

4-nitrophenylalanine (5 g, 1 eq, mmol) was added in portions to a solution of dry ethanol (50 mL) and thionyl-chloride (5 mL) at −5° C. It was stirred at that temperature for another one hour, followed by stirring at RT for 16 h. The reaction mixture was condensed on rotavapour, azeotroped with toluene, and then dried over high vaccum pump to obtain 4-nitrophenylalanine ethyl ester hydrochloride as white solid (quantitative yield).

Step (ii)

4-nitrophenylalanine ethyl ester hydrochloride (2 g, 1.0 eq, 7.28 mmol) obtained in step(i) was dissolved in ethyl acetate (150 mL). To that Na$_2$CO$_3$ (386 mg, 0.5 eq, 3.64 mmol) was added and was stirred for 15 min. The reaction mixture was washed with aq. NaHCO$_3$. The organic layer was dried (Na$_2$SO$_4$), and condensed to obtain 4-nitrophenylalanine ethyl ester as thick oil (1.55 g, 89%).

Step (iii)

4-nitrophenylalanine ethyl ester (1.55 g, 1.0 eq, 6.51 mmol), obtained in step(ii) above was dissolved in chloroform (33 mL). To that glacial acetic acid (20 µL, 0.05 eq, 0.33 mmol), and isoamylnitrite (958 µL, 1.1 eq, 7.16 mmol) were added and the reaction mixture was heated at reflux for 30 min. The reaction mixture was diluted with chloroform, and was washed with aq. NaHCO$_3$. The organic layer was dried (Na$_2$SO$_4$) and condensed (caution!) to a yellowish liquid.

Step (iv)

The liquid (1.54 g, 1.0 eq, 6.18 mmol) thus obtained in step (iii), was dissolved in dry isopropanol (31 mL), and to that catalytic amount of Rh$_2$(OAc)$_4$.2H$_2$O (38 mg, 0.02 eq, 0.12 mmol) was added and the reaction mixture was stirred at room temperature for 16 h. Isopropanol was condensed, and the reaction mixture was diluted with ethyl acetate. The organic layer was washed with water and brine, dried (Na$_2$SO$_4$), and concentrated. Column chromatography, using ethyl acetate and hexanes, provided the desired compound ethyl 2-isopropoxy-3-(4-nitrophenyl)propionate (1.25 g, 61% overall).

$^1$H NMR (200 MHz, CDCl$_3$) δ: 0.92 (d, J=5.8 Hz, 3H), 1.16 (d, J=5.8 Hz, 3H), 1.27 (t, J=7.4 Hz, 3H), 3.00-3.10 (m, 2H), 3.52 (quintet, 1H); 4.08 (dd, J=8.7 and 4.8 Hz, 1H), 4.21 (q, J=7.4 Hz, 2H), 7.43 (d, J=8.7 Hz, 2H), 8.16 (d, J=8.7 Hz, 2H).

IR (neat) cm$^{-1}$: 2975, 1747, 1602, 1522, 1347.

Mass m/z (CI): 282 [M+1]

Preparation 9

Ethyl 2-isopropoxy-3-(4-nitrophenyl)propionate

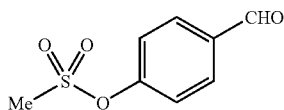

Ethyl 2-isopropoxy-3-(4-nitrophenyl)propionate (1.52 g, 5.4 mmol) obtained in preparation 8 was hydrogenated under 10 psi pressure of molecular hydrogen using 10% Pd/C (700 mg) as catalyst in ethyl acetate (200 mL) at room temperature for 3-4 h. The desired product was isolated after filtering the reaction mixture and concentrating the filtrate under reduced pressure. Column chromatography of the crude mass using ethyl acetate and hexanes provided the desired compound ethyl 2-isopropoxy-3-(4-aminophenyl) propionate (1.16 g, 86% overall ).

$^1$H NMR (200 MHz, CDCl$_3$) δ: 0.97 (d, J=5.8 Hz, 3H), 1.15 (d, J=5.8 Hz, 3H), 1.23 (t, J=7.0 Hz, 3H), 2.80-2.95 (m, 2H), 3.49 (quintet, 1H); 3.98 (dd, J=8.1 and 5.7 Hz, 1H), 4.16 (q, J=7.0 Hz, 2H), 6.61 (d, J=8.3 Hz, 2H), 7.03 (d, J=8.3 Hz, 2H).

IR (neat) cm$^{-1}$: 3455, 3371, 2975, 2929, 1737, 1626, 1519.

Mass m/z (CI): 252 [M+1]

Preparation 10

4-methanesulfonyloxybenzaldehyde

A mixture of 4-hydroxybenzaldehyde (5.0 gm, 1.0 eq, 40.98 mmol), anhydrous K$_2$CO$_3$ (17 g, 3 eq, 123 mmol), and methanesulfonylchloride (4.76 mL, 1.5 eq, 61.37 mmol) in dry DMF (200 mL) was stirred at RT for 16 h. The reaction mixture was diluted with ethyl acetate (200 mL) and washed with water and brine. Organic layer was dried (Na$_2$SO$_4$), condensed, and the residue obtained was chromatographed using ethyl acetate and hexanes to obtain the title compound as white solid (2.0 g, 25%).

Mp: 60-62° C.

$^1$H NMR (CDCl$_3$, 200 MHz) δ: 3.21 (s, 3H); 7.45 (d, J=8.8 Hz, 2H); 7.95 (d, J=8.8 Hz, 2H); 10.01 (s, 1H).

IR (neat) cm$^{-1}$: 3024, 2932, 1701, 1591, 1502.

Mass m/z (CI): 201 [M+1].

Preparation 11

2-(4-Hydroxyphenyl)-1-ethanol

A solution of methyl 2-(4-hydroxyphenyl)acetate (3.0 g, 18.07 mmol), in THF (20 mL) was added to a stirred suspension of LAH (0.89 g, 23.49 mmol) in THF (20 mL) at 0° C. The stirring was continued at RT for 4 h. Excess of LAH was quenched with saturated Na$_2$SO$_4$ solution and the precipitate formed was filtered off. The filtrated was extracted with ethyl acetate and the organic extract was washed with brine, dried (Na$_2$SO$_4$) and evaporated to dryness. Column purification with 50% ethyl acetate-pet ether yielded the title compound (1.1 g, 44%) as a white solid.

Mp: 88-92° C.

$^1$H NMR (200 MHz, CDCl$_3$+DMSO-d$_6$): δ 2.75 (t, J=7.1 Hz, 2H); 3.75 (t, J=6.3 Hz, 2H); 6.75 (d, J=8.3 Hz, 2H); 7.03 (d, J=8.3 Hz, 2H).

Mass m/z (CI): 138 [M].

Preparation 12

4-(2-Methlsulfonyloxyethyl)phenyl methanesulfonate

The title compound (2 g, 94%) was obtained from 2-(4-hydroxyphenyl)-1-ethanol (1.0 g, 7.25 mmol), obtained from preparation 11, in DCM (20 mL) using triethyl amine (2.52 mL, 16.1 mmol) and methanesulfonyl chloride (0.83 mL, 15.9 mmol) at room temperature for 2 h following a similar procedure as described in preparation 1, step (ii).

$^1$H NMR (200 MHz, CDCl$_3$): δ 2.91 (s, 3H); 3.08 (t, J=6.8 Hz, 2H); 3.15 (s, 3H); 4.42 (t, J=6.8 Hz, 2H); 7.20-7.34 (m, 4H).

Mass m/z (CI): 199 [M-OSO$_2$Me].

Preparation 13

Methyl 2-(4-methylsulfonyloxyphenyl)acetate

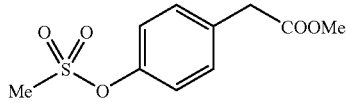

The title compound (1.7 g, 77%) was obtained from methyl 2-(4-hydroxyphenyl) acetate (1.5 g, 9.04 mmol), in DCM (20 mL) using triethyl amine (3.14 mL, 22.59 mmol) and methanesulfonyl chloride (0.84 mL, 10.84 mmol) at room temperature for 2 h following a similar procedure as described in preparation 1, step (ii).

$^1$H NMR (200 MHz, CDCl$_3$): δ 3.14 (s, 3H); 3.64 (s, 2H); 3.71 (s, 3H); 7.24 (d, J=8.8 Hz, 2H); 7.34 (d, J=8.8 Hz, 2H).

Mass m/z: 244 [M].

Preparation 14

2-(4-Methylsulfonyloxyphenyl)acetic acid

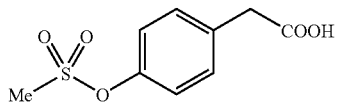

To a solution of methyl 2-(4-methylsulfonyloxyphenyl) acetate (0.95 g, 3.89 mmol), obtained in preparation 13, in methanol (10 mL), Na$_2$CO$_3$ (2.06 g, 19.48 mmol) in water (5 mL) was added and the reaction mixture was stirred at RT for 24 h. Methanol was evaporated and the residue was taken in water and washed with ethyl acetate to free it from impurity, if any. The water layer was acidified to pH ~2 when the title compound separated (0.55 g, 61.4%) as a white solid.

Mp: 158-162° C.

$^1$H NMR (200 MHz, DMSO-d$_6$): δ 3.32 (s, 3H); 3.62 (s, 2H); 7.28 (d, J=8.9 Hz, 2H); 7.37 (d, J=8.6 Hz, 2H).

Mass m/z (CI): 231 [M+1]; 230 [M].

Preparation 15

Methyl 4-nitro cinnamate

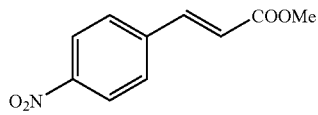

A solution of 4-nitro cinnamic acid (3 g, 15.54 mmol) in methanol (50 mL) was cooled to 10° C. and conc. H$_2$SO$_4$ (1 mL) was slowly added and then refluxed for 30 h. Methanol was evaporated under reduced pressure. Ethyl acetate (150 mL) was added to the residue and the solution was washed with water, satd. NaHCO$_3$ solution, water and brine respectively. The organic layer was dried (Na$_2$SO$_4$) and evaporated to obtain the title compound (3 g, 93%) as off white solid.

Mp: 158-160° C.

$^1$H NMR (200 MHz, CDCl$_3$): δ 3.84 (s, 3H); 6.56 (d, J=15.9 Hz, 1H); 7.64-7.78 (m, 3H); 8.25 (d, J=8.9 Hz, 2H).

Mass m/z (CI): 208 [M+1]; 194 [M-CH$_3$].

Preparation 16

Methyl 3-(4-aminophenyl)propionate

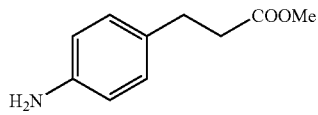

To a solution of methyl 4-nitrocinnamate obtained in preparation 15 (1.5 g, 7.25 mmol) in dioxane (25 mL) 10% Pd—C (0.6 g) was added and hydrogenated at room temperature at 60 psi for 20 h. The reaction mixture was filtered through celite and concentrated under reduced pressure. The crude residue was purified by column chromatography using 50% EtOAc-pet ether to give pure title compound (1.07 g, 82.5%) as off white solid.

Mp: 142-144° C.

$^1$H NMR (200 MHz, CDCl$_3$): δ 2.57 (t, J=7.5 Hz, 2H); 2.85 (t, J=7.8 Hz, 2H); 3.66 (s, 3H); 6.64 (d, J=8.3 Hz, 2H); 7.00 (d, J=8.3 Hz, 2H).

Mass m/z (CI): 180 [M+1].

Preparation 17

3-(4-Aminophenyl)-1-propanol

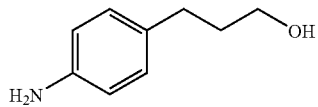

A cold solution of Methyl 3-(4-aminophenyl)propionate obtained in preparation 16 (0.48 g, 2.7 mmol) in THF (10 mL) was slowly added drop wise to a suspension of LAH (132 mg, 3.49 mmol) in THF (10 mL) at 0° C. and stirred for overnight at room temperature. Unreacted LAH was quenched with satd. Na$_2$SO$_4$ solution and filtered through celite and the bed was thoroughly washed with ethyl acetate. The filtrate and the washings were combined and the organic layer was dried (Na$_2$SO$_4$) and evaporated. The residue on purification yielded the title compound (0.27 g, 66.7%) as yellow solid.

Mp: 54-56° C.

$^1$H NMR (200 MHz, CDCl$_3$): δ 1.88-1.92 (m, 2H); 2.60 (t, J=7.5 Hz, 2H); 3.66 (t, J=6.3 Hz, 2H); 6.63 (d, J=8.1 Hz, 2H); 6.99 (d, J=8.1 Hz, 2H).

Mass m/z (CI): 152 [M+1].

Preparation 18

3-(4-Amino-4-tert-butoxyphenyl)-1-propanol

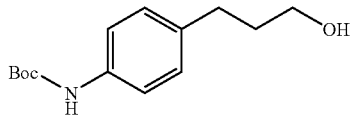

To a cooled (0° C.) solution of 3-(4-aminophenyl)-1-propanol obtained in preparation 17 (0.5 g, 3.3 mmol) in dichloromethane (15 mL) Et$_3$N (1.4 mL) was added followed by the addition of Boc-anhydride (0.84 mL, 3.64 mmol) and the mixture was stirred for 72 h at room temperature. The reaction mixture was diluted with DCM (50 mL) and the organic layer was washed with water and brine, dried (Na2SO$_4$) and evaporated to dryness. Column chromatography of the residue yielded the title compound (0.4 g, 48%) as colorless oil.

$^1$H NMR (200 MHz, CDCl$_3$): δ 1.44-1.53 (m, 9H); 1.78-1.93 (m, 2H); 2.64 (t, J=7.6 Hz, 2H); 3.64 (t, J=6.6 Hz, 2H); 6.41 (bs, 1H, D$_2$O exchangeable); 7.10 (d, J=8.3 Hz, 2H); 7.25 (d, J=8.3 Hz, 2H).

Mass m/z (CI): 252 [M+1]; 152 [M-Boc].

Preparation 19

3-(4-tert-Butoxy-4-methylsulfonamidophenyl)propyl methanesulfonate

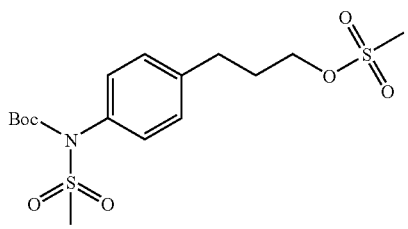

To a cooled (0° C.) solution of 3-(4-Amino-4-tert-butoxyphenyl)-1-propanol obtained in preparation 18 (0.5 g, 3.3 mmol) in dichloromethane (10 mL) Et$_3$N (1.4 mL) was added followed by the addition of mesylchloride (0.27 mL, 3.5 mmol) and the mixture was stirred for 4 h at room temperature. The reaction mixture was diluted with DCM (50 mL) and the organic layer was washed with water and brine, dried (Na$_2$SO$_4$) and evaporated to dryness to yield the title compound (0.61 g, 94%).

$^1$H NMR (200 MHz, CDCl$_3$): δ 1.50 (s, 9H); 1.95-2.10 (m, 2H); 2.68 (t, J=7.5 Hz, 2H); 2.97 (s, 3H); 3.13 (s, 1H); 3.66 (s, 2H); 4.19 (t, J=6.3 Hz, 2H); 7.08 (d, J=8.3 Hz, 2H); 7.27 (d, J=8.3 Hz, 2H).

Mass m/z (CI): 329 [M-SO$_2$Me].

Preparation 20

Methyl 4-hydroxy cinnamate

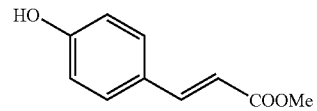

The title compound was obtained as brown colored solid from 4-hydroxy cinnamic acid (2 g, 12.18 mmol) using methanol (25 mL) and conc. H$_2$SO$_4$ (0.8 mL) in 20 h following the same procedure as described in preparation 15.

Mp: 144-146° C.

$^1$H NMR (200 MHz, CDCl$_3$): δ 3.80 (s, 3H); 5.69 (bs, D$_2$O exchangeable); 6.30 (d, J=15.8 Hz, 1H); 6.85 (d, J=8.6 Hz, 2H); 7.43 (d, J=8.6 Hz, 2H); 7.64 (d, J=16.1 Hz, 1H).

Mass m/z (CI): 179 [M+1].

Preparation 21

(E)-3-(4-Hydroxyphenyl)-2-propen-1-ol

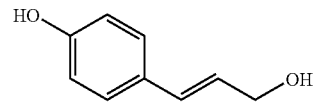

A solution of methyl 4-hydroxy cinnamate obtained in preparation 20(1.5 g, 8.43 mmol) in THF (15 mL) was added drop wise to a suspension of LAH (416 mg) in dry THF (10 mL) at 0° C. and the reaction mixture was stirred at room temperature for 2 h. The excess LAH was quenched with satd. Na$_2$SO$_4$ solution. It was filtered through celite bed and the filtrate was dried (Na$_2$SO$_4$) and evaporated to dryness. The residue was purified by column chromatography using 20% EtOAc in pet ether to afford the title compound (0.4 g, 31.6%) as off white solid.

Mp: 116-118° C.

$^1$H NMR (200 MHz, CD$_3$OD) δ: 4.17 (d, J=5.9 Hz, 2H); 6.15 (td, J=5.9 and 15.8 Hz, 1H); 6.50 (d, J=5.9 Hz, 1H); 6.71 (d, J=8.3 Hz, 2H); 7.23 (d, J=8.6 Hz, 2H)

Mass m/z (CI): 151 [M+1]

Preparation 22

4-[(E)-3-chloro-1-propenyl]phenylmethanesulfonate

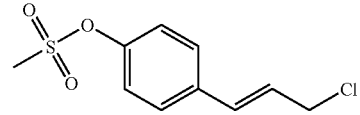

The title compound was obtained (0.47 g, 64%) from (E)-3-(4-Hydroxyphenyl)-2-propen-1-ol (0.36 g, 2.4 mmol) obtained in preparation 21, DCM (10 mL), Et₃N (0.83 mL) and methanesulfonyl chloride (0.41 mL) the same way as described in the preparation 19.

¹H NMR (200 MHz, CDCl₃): δ 3.14 (s, 3H); 4.24 (d, J=7.0 Hz, 2H); 6.21-6.4 (m, 1H); 6.65 (d, J=15.8 Hz, 1H); 7.25 (d, J=8.6 Hz, 2H); 7.43 (d, J=8.8 Hz, 2H).

Mass m/z (CI): 247 [M+1].

Preparation 23

(E)-3-(4-Methylsulfonyloxyphenyl)-2-propenoic acid

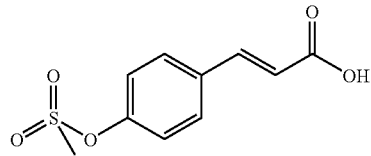

The title compound was obtained (0.53 g, 36%) from (E)-4-hydroxycinnamic acid (1.0 g, 6.1 mmol), DCM (20 mL), Et₃N (2.12 mL, 15.24 mmol) and methanesulfonyl chloride (0.57 mL, 7.32 mmol) the same way as described in the preparation 19.

¹H NMR (200 MHz, CDCl₃): δ 3.20 (s, 3H); 6.51 (d, J=15.8 Hz, 1H); 7.36 (d, J=8.6 2H); 7.64 (d, J=8.3 Hz, 2H); 7.81 (d, J=15.8 Hz, 1H).

Mass m/z (CI): 243 [M+1].

Preparation 24

3-(4-Methylsulfonyloxyphenyl)propenoic Acid

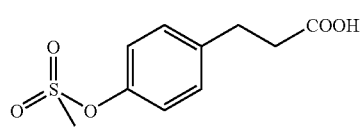

The title compound was obtained (1.02 g, 69.4%) from 3-(4-hydroxyphenyl)propionic acid (1.0 g, 6.02 mmol), DCM (15 mL), Et₃N (2.1 mL, 15.06 mmol) and methanesulfonyl chloride (0.56 mL, 7.23 mmol) the same way as described in the preparation 19.

¹H NMR (200 MHz, CDCl₃): δ 2.74 (t, J=7.4 Hz, 2H); 3.00-3.09 (m, 2H); 3.14 (s, 3H); 7.14-7.37 (m, 4H).

Mass m/z (CI): 245 [M+1].

Preparation 25

Ethyl (2S)-3-(4-aminophenyl)-2-ethoxypropanoate and Ethyl (2R)-3-(4-aminophenyl)-2-ethoxypropanoate

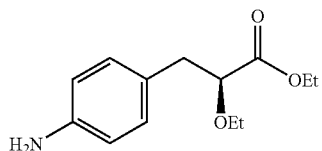

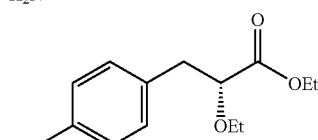

Step (i)

Ethyl 3-(4-dibenzylaminophenyl)-2-ethoxy propanoate

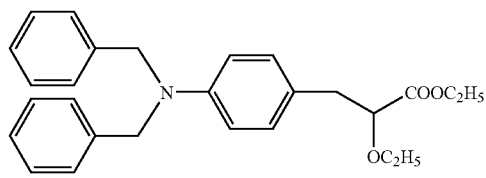

To a cooled solution of ethyl 2-ethoxy-3-(4-aminophenyl)propanoate (2.0 g, 8.44 mmol), obtained in preparation 5, in dry DMF (30 mL) Na₂CO₃ (2.68 g, 25.3 mmol) was added and stirred for 15 min. Benzyl bromide (2.0 mL, 16.88 mmol) was then added to the solution drop wise and the reaction mixture was stirred for 16 h at rt. The reaction mixture was diluted with water (50 mL) and extracted with ethyl acetate (3×50 mL). The combined organic layers were washed with brine, dried (Na₂SO₄) and evaporated to dryness to get the title compound as yellow oil (3.42 g, 97%), which was used for the next step without purification.

¹H NMR (200 MHz, CDCl₃): δ 1.06-1.32 (m, 6H); 2.89 (d, J=6.4 Hz, 2H); 3.28-3.48 (m, 1H); 3.52-3.70 (m, 1H); 3.95 (t, J=6.6 Hz, 1H); 4.12 (q, J=7.0 Hz, 2H); 4.63 (s, 4H); 6.67 (d, J=7.0 Hz, 2H); 7.03 (d, J=8.3 Hz, 2H); 7.15-7.43 (m, 10H).

Mass m/z (CI): 418 [M+1].

Step (ii)

3-(4-Dibenzylaminophenyl)-2-ethoxypropionic Acid

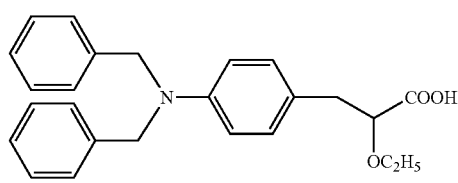

To a solution of the compound obtained in step (i) (0.5 g, 1.2 mmol) in methanol (10 mL) $Na_2CO_3$ (380 mg, 3.6 mmol) in water (2 mL) was added and the reaction mixture was stirred for 3 days at RT. Methanol was then removed and the reaction mixture was diluted with water (10 mL). The aqueous layer was extracted with ethyl acetate to remove any unwanted non-polar impurities. Then the aqueous layer was acidified with 2N HCl solution to pH ~4 and extracted with ethyl acetate. The combined ethyl acetate layers were washed with brine (3×10 mL), dried ($Na_2SO_4$) and concentrated to yield the title compound (0.340 g, 74%).

$^1$H NMR (200 MHz, $CDCl_3$): δ 1.17 (t, J=7.1 Hz, 3H); 2.82-3.05 (m, 2H); 3.29-3.67 (m, 2H); 3.97-4.09 (m, 1H); 4.63 (s, 4H); 6.67 (d, J=8.8 Hz, 2H); 7.03 (d, J=8.3 Hz, 2H); 7.13-7.42 (m, 10H).

Mass m/z (CI): 390 [M+1].

Step (iii)

N1-[(1S)-1-phenylpropyl]-(2S)-3-(4-dibenzylaminophenyl)-2-ethoxypropan-amide (iiia)

and

N1-[(1S)-1-phenylpropyl]-(2R)-3-(4-dibenzylaminophenyl)-2-ethoxypropan-amide (iiib)

iiia

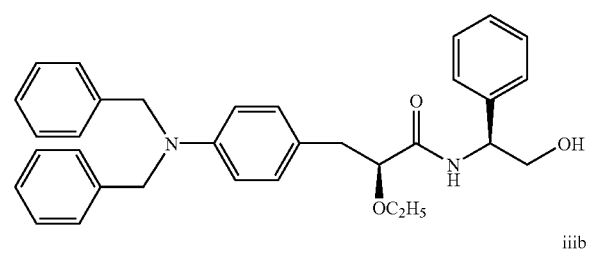

iiib

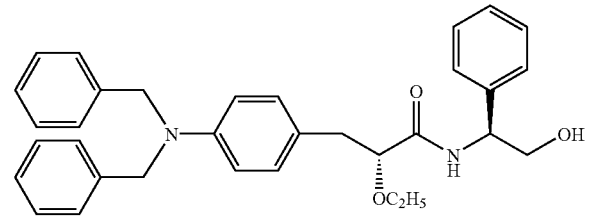

To a cooled solution of compound obtained in step (ii) (1.0 g, 2.57 mmol) in dry DCM 5-hydroxybenzotriazole (172 mg, 1.286 mmol) and EDCI (592 mg, 3.08 mmol) were added and the reaction mixture was stirred at 0° C. for 30 min (until it became a clear solution). 2-L-Phenyl glycinol (0.37 g, 2.69 mmol) was added to the solution and stirred at RT for 16 h. The reaction mixture was diluted with DCM (25 mL), washed with water (3×25 mL), dried ($Na_2SO_4$) and concentrated. The diastereomers were separated on silica gel column using 10-45% ethyl acetate in pet ether.

Yield of iiia: 420 mg (32%); white solid, mp: 110-112° C.
Yield of iiib: 380 mg (29%).

iiia: $^1$H NMR (200 MHz, $CDCl_3$): δ 1.18 (t, J=7.1 Hz, 3H); 2.74-3.12 (m, 2H); 3.46-3.64 (m, 2H); 3.87 (d, J=5.4 Hz, 2H); 3.98 (dd, J=6.9 and 3.7 Hz, 1H); 4.64 (s, 4H); 4.93-5.05 (m, 1H); 6.64 (d, J=8.4 Hz, 2H); 7.02 (d, J=8.3 Hz, 2H); 7.12-7.46 ($m_3$, 15H).

Mass m/z (CI): 509 [M+1].

iiib: $^1$H NMR (200 MHz, $CDCl_3$): δ 1.13 (t, J=7.6 Hz, 3H); 2.80-3.16 (m, 2H); 3.39-3.68 (m, 4H); 3.96 (dd, J=3.9 and 5.5 Hz, 1H); 4.64 (s, 4H); 4.85-5.00 (m, 1H); 6.67 (d, J=6.8 Hz, 2H); 6.97 (d, J=6.8 Hz, 2H); 7.06 (d, I=8.3 Hz, 2H); 7.12-7.42 (m, 13H).

Mass m/z (CI): 509 [M+1].

Step (iv)

(2S)-3-(4-Dibenzylaminophenyl)-2-ethoxypropanoic Acid (iva)

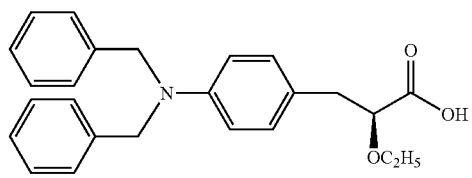

To a solution of compound iiia (410 mg, 0.8 mmol) in dioxane (6 mL) was added 1M $H_2SO_4$ (4 mL) and the reaction mixture was refluxed for 24 h. Dioxane was removed under reduced pressure and the residue was diluted with water (10 mL). The aqueous layer was extracted with ethyl acetate (3×25 mL) and the combined organic layers were washed with brine, dried ($Na_2SO_4$) and evaporated to dryness. The crude mass was purified on silica gel using 40% ethyl acetate in pet ether to yield the title compound (180 mg, 58%).

$[α]_D^{25}$=1.8° (c 0.5, MeOH).

$^1$H NMR (200 MHz, $CDCl_3$): δ 1.16 (t, J=7.6 Hz, 3H); 2.80-3.07 (m, 2H); 3.43-3.68 (m, 2H); 4.16 (dd, J=7.3 and 4.4 Hz, 1H); 4.61 (s, 4H); 6.65 (d, J=8.3 Hz, 2H); 7.04 (d, J=8.8 Hz, 2H); 7.12-7.39 (m, 10H).

Mass m/z (CI): 390 [M+1].

(2S)-3-(4-Dibenzylaminophenyl)-2-ethoxypropanoic Acid (ivb)

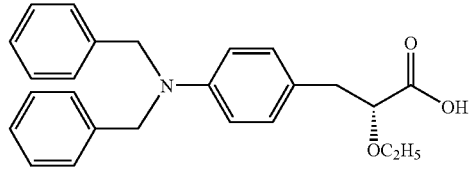

Compound ivb was obtained (152 mg, 60%) from compound iiib (0.5 g, 0.98 mmol) using 1M $H_2SO_4$ (5 mL) in dioxane under reflux for 24 h following the same procedure as described for the preparation of compound iva.

$^1$H NMR (200 MHz, $CDCl_3$): δ 1.18 (t, J=7.0 Hz, 3H); 2.83-3.05 (m, 2H); 3.40-3.67 (m, 2H); 4.03 (dd, J=7.3 and 4.3 Hz, 1H); 4.63 (s, 4H); 6.67 (d, J=8.6 Hz, 2H); 7.03 (d, J=8.6 Hz, 2H); 7.15-7.40 (m, 10H).

Mass m/z (CI): 390 [M+1].

Step v (2S)-3-(4-Dibenzylaminophenyl)-2-ethoxypropanoate (va)

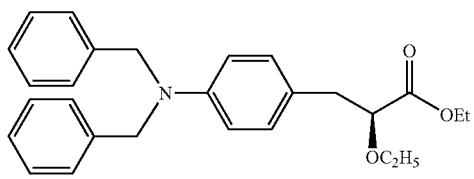

To a cooled solution of compound iva (1.2 g, 3.08 mmol) in dry DMF (30 mL) $K_2CO_3$ (1.277 g, 9.25 mmol) was added and stirred for 15 min at low temperature. Ethyl iodide (0.75 mL, 9.25 mmol) was added and the reaction mixture was allowed to stir for 3 h at rt. Water added and the reaction mixture was extracted with ethyl acetate (3×30 mL). The combined organic layers were washed (brine), dried ($Na_2SO_4$) and concentrated to yield the title compound (1.1 g, 85%).

$^1$H NMR (200 MHz, $CDCl_3$): δ 1.09-1.30 (m, 6H); 2.90 (d, J=6.5 Hz, 2H); 3.27-3.67 (m, 2H); 3.96 (t, J=6.7 Hz, 1H); 4.14 (q, J=7.3 Hz, 2H); 4.63 (s, 4H); 6.65 (d, J=8.6 Hz, 2H); 7.03 (d, J=8.3 Hz, 2H); 7.15-7.42 (m, 10H).

Mass m/z (CI): 418 [M+1].

(2S)-3-(4-Dibenzylaminophenyl)-2-ethoxypropanoate (vb)

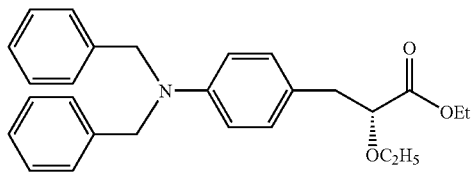

Compound vb (120 mg, 74%) was obtained from compound ivb (150 mg, 0.39 mmol), $K_2CO_3$ (156 mg, 1.17 mmol), ethyl iodide (0.09 mL, 1.17 mmol) in dry DMF following the same procedure as described for the preparation of va.

$^1$H NMR (200 MHz, $CDCl_3$): δ 1.08-1.30 (m, 6H); 2.89 (d, J=6.4 Hz, 2H); 3.28-3.67 (m, 2H); 3.95 (t, J=10 Hz, 1H); 4.13 (q, J=7.0 Hz, 2H); 4.62 (s, 4H); 6.64 (d, J=8.6 Hz, 2H); 7.02 (d, J=8.6 Hz, 2H); 7.19-7.40 (m, 10H).

Mass m/z (CI): 418 [M+1].

Step (vi)

Ethyl (2S)-3-(4-aminophenyl)-2-ethoxypropanoate (via)

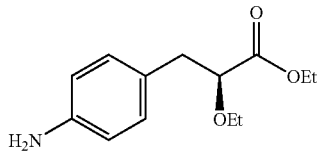

To a solution of va (1.0 g, 2.4 mmol) in methanol (20 mL) 10% Pd—C (0.2 g, 20% w/w) was added and the mixture was hydrogenated on parr hydrogenator at 60 psi for 24 h at RT. The reaction mixture was filtered through celite and washed the bed with methanol. The combined layers were evaporated to dryness and the residue was purified on silica gel using 20% EtOAc in pet ether to give the title compound (300 mg, 53%).

$^1$H NMR (200 MHz, $CDCl_3$): δ 1.17 (t, J=6.8 Hz, 3H); 1.23 (t, J=7.0 Hz, 3H); 2.91 (d, J=6.8 Hz, 2H); 3.25-3.79 (m, 2H); 3.95 (t, J=6.8 Hz, 1H); 4.13 (q, J=7.6 Hz, 2H); 6.62 (d, J=8.3 Hz, 2H); 7.03 (d, J=8.3 Hz, 2H).

Mass m/z (CI): 238 [M+1].

Ethyl (2S)-3-(4-aminophenyl)-2-ethoxypropanoate (vib)

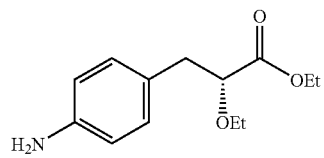

Compound vib was obtained (1.6 g, 84%) from compound vb (1.6 g, 3.89 mmol) using 10% Pd—C (0.32 g, 20% w/w) in methanol (20 mL) for 24 h following the same procedure as described for the preparation of compound via.

$^1$H NMR (200 MHz, $CDCl_3$): δ 1.17 (t, J=7.0 Hz, 3H); 1.23 (t, J=7.0 Hz, 3H); 2.90 (d, J=6.7 Hz, 2H); 3.25-3.80 (m, 2H); 3.94 (t, J=6.7 Hz, 1H); 4.16 (q, J=7.1 Hz, 2H); 6.61 (d, J=8.3 Hz, 2H); 7.03 (d, J=8.1 Hz, 2H).

Mass m/z (CI): 238 [M+1].

Preparation 26

(S)-Ethyl 2-ethoxy-3-(4-aminophenyl)propionate

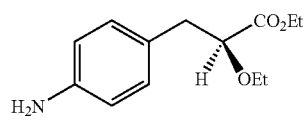

Step (i)

To a solution of (S)-(4-nitrophenyl) glycine (10 g, 47.6 mmol) in a mixture of water (50 mL), $H_2SO_4$ (1M, 60 mL) and acetone (150 mL) at −5° C., was added under stirring, a solution of sodium nitrite (9.85 g, 142.8 mmol) in water (40 mL) drop wise over a period of 30 min. The reaction mixture was stirred at −5 to 0° C. for another 1.5 h, followed by stirring at room temperature for 16 h. Acetone was removed and then the reaction mixture was diluted with 500 mL ethyl acetate. Organic layer was washed with brine, dried over anhydrous Na$_2$SO$_4$, and concentrated. The crude mass was purified by crystallization from isopropyl acetate (9.0 g, 96%).

Mp: 134-136° C.

[α]$_D$: −25° (c 1.0, MeOH)

$^1$H NMR (CDCl$_3$) δ: 3.04 (dd, J=14, 7.8 Hz, 1H), 3.24 (dd, J=14, 4, Hz, 1H), 4.39 (dd, J=7.3, 4.1 Hz, 1H), 7.42 (d, J=8.7 Hz, 2H), 8.16 (d, J=8.7 Hz, 2H).

IR (neat) cm$^{-1}$: 3485, 3180, 2927, 1715, 1515, 1343.

Mass m/z (CI): 212 (M+1).

Step (ii)

(S)-2-Hydroxy-3-(4-nitrophenyl)propionic acid (9.0 g, 42.6 mmol), obtained from step (i) above, was dissolved in dry EtOH (300 mL). To this solution was added conc. H$_2$SO$_4$ (326 μL, 5.9 mmol), and refluxed for 5 to 6 h. The reaction mixture was neutralized with aqueous sodium bicarbonate. Ethanol was condensed on rotavapor, and the residue was dissolved in ethyl acetate. Organic layer was washed with aqueous sodium bicarbonate, water, brine, and then dried over anhydrous Na$_2$SO$_4$, and concentrated. Desired product was obtained from the crude mass by crystallizing from diisopropylether (8.0 g, 78.5%).

Mp: 74-76° C.

[α]$_D$: −13° (c 1.0, MeOH)

$^1$H NMR (CDCl$_3$) δ: 1.30 (t, J=7 Hz, 3H), 3.06 (dd, J=14, 7, Hz, 1H), 3.25 (dd, J=14, 4.3, Hz, 1H), 4.25 (q, J=7 Hz, 2H), 4.25 (dd, J=7, 4.3 Hz, 1H), 7.42 (d, J=8.7 Hz, 2H), 8.16 (d, J=8.7 Hz, 2H).

IR (neat) cm$^{-1}$: 3432, 2924, 1736, 1518, 1347.

Mass m/z (CI): 240 (M+1).

Step (iii)

To a mixture of (S)-Ethyl 2-Hydroxy-3-(4-nitrophenyl)propionate (4.77 g, 19.95 mmol), obtained in step ii above, molecular sieves (4 A) (5.0 g) and powdered Ag$_2$O (13.8 g, 59.8 mmol) in dry acetonitrile (100 mL), was added ethyl iodide (6.4 mL, 79.8 mmol) at room temperature. The reaction mixture was heated at 60° C. for 16 h. The reaction mixture was filtered through celite, and concentrated. The crude mass was chromatographed using ethyl acetate and hexanes to obtain the desired product as viscous liquid (3.5 g, 67% isolated yield). Unreacted starting material was recovered (900 mg) which could be reused.

[α]$_D$: −26° (c 1.0, MeOH).

$^1$H NMR (CDCl$_3$) δ: 1.15 (t, J=7 Hz, 3H); 1.26 (t, J=7.1 Hz, 3H); 3.10 (d, J=3.8 Hz, 1H); 3.13 (s, 1H); 3.16-3.35 (m, 1H); 3.45-3.65 (m, 1H); 4.03 (dd, J=7.5, 5.4 Hz, 1H); 4.21 (q, J=7.2 Hz, 2H); 7.43 (d, J=8.6 Hz, 2H); 8.15 (d, J=8.6 Hz, 2H).

IR (neat) cm$^{-1}$: 2980, 1747, 1604, 1521, 1347.

Mass m/z (CI): 268 (M+1).

Step (iv)

(S)-Ethyl 2-ethoxy-3-(4-nitrophenyl)propionate (6.0, 25.3 mmol), obtained in step (iii) above, was dissolved in dry methanol (100 mL). To this solution was added 10% Pd/C (2.0 g), and was hydrogenated using hydrogen gas (20 psi) for 3-4 h. The reaction mixture was filtered through celite, and the filtrate was concentrated to provide a syrupy mass. The product was obtained in quantitative yield.

[α]$_D$: −14.2° (c 1.0, MeOH).

Chiral HPLC: >98% ee.

$^1$H NMR (CDCl$_3$) δ: 1.16 (t, J=7.0 Hz, 3H), 1.22 (t, J=7.0 Hz, 3H), 2.90 (d, J=6.3 Hz, 2H), 3.30 (bs, 2H, NH2), 3.24-3.42(m, 1H), 3.50-3.70 (m, 1H), 3.94 (t, J=6.3 Hz, 1H), 4.15 (q, J=7.0 Hz, 2H), 6.62 (d, J=8.3 Hz, 2H), 7.03 (d, J=8.0 Hz, 2H).

IR (neat) cm$^{-1}$: 3372, 1738.

Mass m/z (CI): 238 (M+1), 192 (M-OC$_2$H$_5$).

Preparation 27

(S)-Ethyl 2-methoxy-3-(4-aminophenyl)propionate

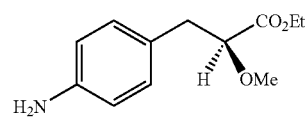

Step (i)

To a mixture of (S)-Ethyl 2-Hydroxy-3-(4-nitrophenyl)propionate (12.5 g, 52.3 mmol), obtained in step (ii) of preparation 26, and powdered Ag$_2$O (36.3 g, 157 mmol) in dry acetonitrile (260 mL) was added methyl iodide (13 mL, 209.2 mmol) at room temperature. Activated molecular sieves (4 A) (12.5 g) were added and then the reaction mixture was stirred at room temperature for 16 h. The reaction mixture was filtered through celite, and concentrated. The crude mass was chromatographed using ethyl acetate and hexanes to obtain the desired product as viscous liquid (10.0 g, 75%).

[α]$_D$: −30.1° (c 1.0, MeOH)

$^1$H NMR (CDCl$_3$) δ: 1.24 (t, J=7.1 Hz, 3H); 3.09 (d, J=5.4 Hz, 1H); 3.12 (d, J=2.7 Hz, 1H); 3.35 (s, 3H); 3.96 (dd, J=7.5, 5.1 Hz, 1H); 4.19 (q, J=7.1 Hz, 2H); 7.39 (d, J=8.6 Hz, 2H); 8.13 (d, J=8.6 Hz, 2H).

IR (neat) cm$^{-1}$: 2995, 1747, 1604, 1521, 1343.

Mass m/z (CI): 254 (M+1).

Step (ii)

(S)-Ethyl 2-methoxy-3-(4-nitrophenyl)propionate (8.0, 31.6 mmol), obtained in step (i) above, was dissolved in dry methanol (200 mL). To this solution was added 10% Pd/C (2.5 g), and hydrogenated using hydrogen gas (20 psi) for 3-4 h. The reaction mixture was filtered through celite, and concentrated to a syrupy mass. After column chromatography using ethyl acetate/hexanes the desired product was isolated as thick liquid (7.0 g, quantitative).

[α]$_D$: −14.1° (c 1.0, MeOH).

Chiral HPLC: >98% ee.

$^1$H NMR (CDCl$_3$) δ: 1.23 (t, J=7.2 Hz, 3H), 2.91 (d, J=6.1 Hz, 2H), 3.30 (bs, 2H, NH$_2$), 3.34 (s, 3H), 3.88 (t, J=6.2 Hz, 1H), 4.17 (q, J=7.2 Hz, 2H), 6.62 (d, J=8.3 Hz, 2H), 7.01 (d, J=8.1 Hz, 2H).

IR (neat) cm$^{-1}$: 3372, 2985, 2932, 1739, 1627, 1519.

Mass m/z (CI): 223 (M), 234 (M+1), 192 (M-OMe).

Preparation 28

(S)-Ethyl 2-ethoxy-3-(4-aminophenyl)propionate

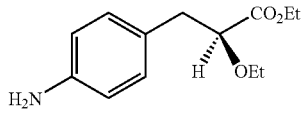

Step (i)

(S)-Ethyl 2-hydroxy-3-(4-nitrophenyl)propionate (9.6 g, 40.1 mmol), obtained in step (ii) preparation 26, was dissolved in ethyl acetate (250 mL). To this solution was added 10% Pd/C (7.0 g) and hydrogenated using hydrogen gas (20 psi) for 3-4 h. The reaction mixture was filtered through celite, and concentrated to obtain a syrupy mass. After column chromatography using ethyl acetate/hexanes the desired product was isolated as thick liquid (6.1 g, 72%).

$[\alpha]_D$: +6.5° (c 1.0, MeOH).

$^1$H NMR (CDCl$_3$) δ: 1.25 (t, J=7.2 Hz, 3H), 2.83 (dd, J=14, 6.5, Hz, 1H), 2.98 (dd, J=14, 4.6, Hz, 1H), 3.35 (bs, 2H, NH$_2$), 4.17 (q, J=7.2 Hz, 2H), 4.33 (dd, J=6.5, 4.6 Hz, 1H), 6.58 (d, J=8.4 Hz, 2H), 6.97 (d, J=8.1 Hz, 2H).

IR (neat) cm$^{-1}$: 3372, 2985, 2932, 1739, 1627, 1519.

Mass m/z (CI): 209 [M], 210 [M+1].

Step (ii)

A mixture of (S)-Ethyl 2-hydroxy-3-(4-aminophenyl)propionate (4.0 g, 19.1 mmol), obtained in step (i) above, benzyl bromide (4.7 mL, 40.19 mmol) and anhydrous Na$_2$CO$_3$ (6.07 g, 57.3 mmol) in dry DMF (100 mL) was stirred at room temperature for 16 h. The reaction mixture was diluted with ethyl acetate (300 mL), washed with 10% aqueous citric acid, dried over anhydrous Na$_2$SO$_4$, and concentrated. After column chromatography using ethyl acetate/hexanes the desired product was isolated as thick liquid (4.5 g, 61%).

$[\alpha]_D$: −12° (c 0.1, MeOH)

$^1$H NMR (CDCl$_3$) δ: 1.25 (t, J=7.2Hz, 3H), 2.16 (s, OH); 2.84 (dd, J=14, 6.5, Hz, 1H), 2.99 (dd, J=14, 4.6, Hz, 1H), 4.19 (q, J=7.2 Hz, 2H), 4.31-4.37 (m, 1H), 4.62 (s, 4H); 6.66 (d, J=8.8Hz, 2H), 7.01 (d, J=8.8Hz, 2H); 7.21-7.35 (aromatics, 10H).

IR (neat) cm$^{-1}$: 3497, 3062, 3028, 1733, 1615, 1521.

Mass m/z (CI): 390 [M+1].

Step (iii)

(S)-Ethyl 2-hydroxy-3-(4-dibenzylaminophenyl)propionate (4.5 g, 1.0 eq, 11.57 mmol), obtained in step (ii) above, was hydrolyzed in MeOH-THF-water using LiOH.H$_2$O (972 mg, 2 eq, 23.1 mmol) at room temperature. The reaction mixture was concentrated and the pH adjusted to 3. The desired acid was precipitated out, which was then filtered (4.0 g, 96% yield).

Mp: 114-116° C.

$^1$H NMR (CDCl$_3$) δ: 2.83 (dd, J=14, 7 Hz, 1H); 3.09 (dd, J=14, 3.5 Hz, 1H), 4.35-4.44 (m, 1H), 4.62 (s, 4H); 6.68 (d, J=8.3 Hz, 2H), 7.03 (d, J=8.3 Hz, 2H); 7.21-7.35 (aromatics, 10H).

IR (neat) cm$^{-1}$: 3450, 3028, 2923, 1725, 1615, 1521.

Mass m/z (CI): 362 [M+1].

Step (iv)

To a solution of (S)-2-hydroxy-3-(4-dibenzylaminophenyl)propionic acid (4.0 g, 11.1 mmol), obtained in step (iii), in dry DMF (56 mL) was added in portions NaH (60% in oil, 886 mg, 22.2 mmol) at room temperature. The resulting mixture was stirred at 50° C. for 2 h. The reaction mixture was again brought back at room temperature, and ethyl iodide (2.67 mL, 33.3 mmol) was added. The resulting mixture was stirred at room temperature for 16 h. The reaction mixture was diluted with ethyl acetate and washed with water and brine. Organic layer was dried over anhydrous Na$_2$SO$_4$, and concentrated. The residue was purified by column chromatography using ethyl acetate/hexanes to obtain the desired product as viscous liquid (2.65 g, 57% yield).

$[\alpha]_D$: −3.5° (c. 1, MeOH).

$^1$H NMR (CDCl$_3$) δ: 1.18 (t, J=7.0 Hz, 3H), 1.20 (t, J=7.3 Hz, 3H), 2.91 (d, J=6.7 Hz, 2H), 3.30-3.48 (m, 1H), 3.52-3.70 (m, 1H), 3.97 (t, J=6.7 Hz, 1H), 4.15 (q, J=7.2 Hz, 2H), 4.62 (s, 4H), 6.67 (d, J=8.3Hz, 2H), 7.04 (d, J=8.0Hz, 2H), 7.23-7.36 (aromatics, 10H).

IR (neat) cm$^{-1}$: 3027, 2978, 1744, 1616, 1521.

Mass m/z (CI): 418 (M+1).

Step (v)

(S)-Ethyl 2-ethoxy-3-(4-dibenzylaminophenyl)propionate, obtained in step (iv) above, was hydrogenolyzed using Pd/C (10%), and hydrogen gas (20-30 psi) in ethyl acetate solvent for 3-4 h. From the reaction mixture the desired product was obtained just after filtering off the catalyst, and concentrating the filtrate.

$[\alpha]_D$: −14.2° (c 1.0, MeOH).

Chiral HPLC: >98% ee.

$^1$H NMR (CDCl$_3$) δ: 1.16 (t, J=7.0 Hz, 3H), 1.22 (t, J=7.0Hz, 3H), 2.90 (d, J=6.3Hz, 2H), 3.30 (bs, 2H, NH2), 3.24-3.42(m, 1H), 3.50-3.70 (m, 1H), 3.94 (t, J=6.3Hz, 1H), 4.15 (q, J=7.0Hz, 2H), 6.62 (d, J=8.3Hz, 2H), 7.03 (d, J=8.0Hz, 2H).

IR (neat) cm$^{-1}$: 3372, 1738.

Mass m/z (CI): 238 (M+1), 192 (M-OC$_2$H$_5$).

EXAMPLE 1

(S)-Ethyl 2-methoxy-3-[4-{3-(4-methanesulfonyloxyphenyl) propylamino}phenyl]propionate

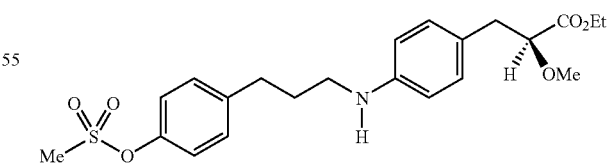

A mixture of 4-(3-methanesulfonyloxypropyl)phenylmethanesulfonate (5.5 g, 1.0 eq, 17.9 mmol), obtained in preparation 1, (S) ethyl 2-methoxy-3-(4-aminophenyl)propionate (4.0 g, 1.0 eq, 17.9 mmol), obtained in preparation 27, tetrabutylammonium bromide (2.8 g, 0.5 eq, 9.0 mmol) and anhydrous K$_2$CO$_3$ (7.4 g, 3.0 eq, 53.7 mmol) in dry toluene (90 mL) was heated with stirring at 90° C. for 7-9 h. The reaction mixture was diluted with ethyl acetate (300 mL) and washed with water and brine. Organic layer was dried ($Na_2SO_4$), condensed, and the residue was chromatographed using ethyl acetate and hexanes to obtain the title compound as viscous liquid (3.4 g, 44%).

[α]25$_D$: −6.5°(c1.0, MeOH).

$^1$H NMR (CDCl$_3$, 200 MHz): δ 1.26 (t, J=7.0 Hz, 3H); 1.98 (quintet, J=7.2 Hz, 2H); 2.75 (t, J=7.6 Hz, 2H); 2.93 (d, J=5.9 Hz, 2H); 3.02-3.22 (m, 5H); 3.37 (s, 3H); 3.91 (t, J=6.4 Hz, 1H); 4.20 (q, J=7.0 Hz, 2H); 6.65 (d, J=8.0 Hz, 2H); 7.08 (d, J=8.3 Hz, 2H); 7.15-7.3 (aromatics, 4H).

IR (neat) cm$^{-1}$: 3405, 2934, 2934, 1739, 1617, 1522, 1367.

Mass m/z (CI): 435 [M], 436 [M+1].

EXAMPLE 2

Ethyl 2-ethoxy-3-[4-{3-(4-methanesulfonyloxyphenyl)propylamino}phenyl]propionate

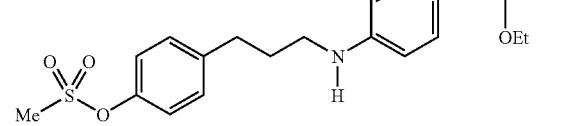

Starting from 4-(3-methanesulfonyloxypropyl)phenylmethanesulfonate obtained in preparation 1 and Ethyl 2-ethoxy-3-(4-aminophenyl)propionate, obtained in preparation 5, the title compound was obtained as a viscous liquid (40% yield) following the procedure of Example 1.

$^1$H NMR (CDCl$_3$, 200 MHz): δ 1.16 (t, J=5.8 Hz, 3H); 1.21 (t, J=5.8 Hz, 3H); 1.91 (quintet, J=7.2 Hz, 2H); 2.72 (t, J=7.3 Hz, 2H); 2.88 (d, J=6.3 Hz, 2H); 3.02-3.18 (m, 5H); 3.22-3.42 (m, 1H); 3.42-3.62 (m, 1H); 3.93 (t, J=6.5 Hz, 1H); 4.15 (q, J=7.3 Hz, 2H); 6.51 (d, J=8.3 Hz, 2H); 7.10 (d, J=8.3 Hz, 2H); 7.15-7.24 (aromatics, 4H).

IR (neat) cm$^{-1}$: 3400, 2978, 2934, 1738, 1616, 1502.

Mass m/z (CI): 449 [M], 450 [M+1].

EXAMPLE 3

(S)-Ethyl 2-ethoxy-3-[4-{3-(4-methanesulfonyloxyphenyl) propylamino}phenyl]propionate

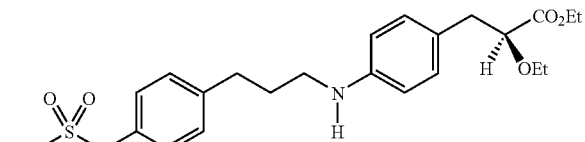

From 4-(3-methanesulfonyloxypropyl)phenylmethanesulfonate obtained in preparation 1 and (S)-ethyl 2-ethoxy-3-(4-aminophenyl)propionate, obtained in preparation 26, the title compound was obtained following the procedure of Example 1.

[α]25$_D$: −6.3°(1.0, MeOH).

$^1$H NMR (CDCl$_3$, 200 MHz): δ 1.16 (t, J=5.8 Hz, 3H); 1.21 (t, J=5.8 Hz, 3H); 1.91 (quintet, 7.2 Hz, 2H); 2.72 (t, J=7.3 Hz, 2H); 2.88 (d, J=6.3 Hz, 2H); 3.02-3.18 (m, 5H); 3.22-3.42 (m, 1H); 3.42-3.62 (m, 1H); 3.93 (t, J=6.5 Hz, 1H); 4.15 (q, J=7.3 Hz, 2H); 6.51 (d, J=8.3 Hz, 2H); 7.10 (d, J=8.3 Hz, 2H); 7.15-7.24 (aromatics, 4H).

IR (neat) cm$^{-1}$: 3400, 2978, 2934, 1738, 1616, 1502.

Mass m/z (CI): 449 [M], 450 [M+1].

EXAMPLE 4

Ethyl 2-ethoxy-3-[4-{3-(4-methanesulfonyloxyphenyl)propyloxycarbonylamino}phenyl]propionate

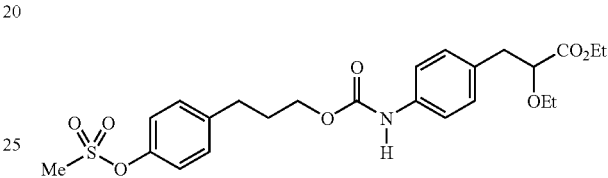

The Title Compound was Obtained as a Side Product During Synthesis of Example 2 (20% Yield)

$^1$H NMR (CDCl$_3$, 200 MHz): δ 1.14 (t, J=7 Hz, 3H); 1.22 (t, J=7 Hz, 3H); 1.98 (quintet, J=7 Hz, 2H); 2.72 (t, J=8 Hz, 2H); 2.95 (d, J=6.1 Hz, 2H); 3.10 (s, 3H); 3.25-3.45 (m, 1H); 3.50-3.70 (m, 1H); 3.97 (t, J=6.4 Hz, 1H); 4.05-4.24 (m, 4H); 6.68 (s, NH); 7.10-7.30 (aromatics, 8H);

IR (neat) cm$^{-1}$: 3357, 2978, 1730, 1530

Mass m/z (CI): 494 [M+1]

EXAMPLE 5

Ethyl 2-ethoxy-3-[4-{3-(3-methanesulfonyloxyphenyl)propylamino}phenyl]propionate

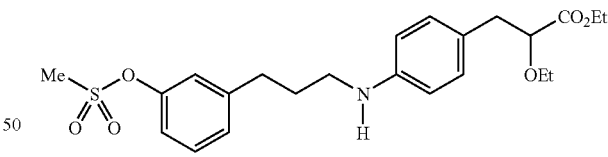

From 3-(3-methanesulfonyloxypropyl)phenylmethanesulfonate obtained in preparation 2 and Ethyl 2-ethoxy-3-(4-aminophenyl)propionate obtained in preparation 5, the title compound was obtained as a viscous liquid (, 44%) following the procedure of Example 1.

$^1$H NMR (CDCl$_3$, 200 MHz): δ 1.19 (t, J=7.0 Hz, 3H); 1.25 (t, J=7.0 Hz, 3H); 1.91 (quintet, J=7.3 Hz, 2H); 2.78 (t, J=7.8 Hz, 2H); 2.92 (d, J=6.7 Hz, 2H); 3.02-3.20 (m, 5H); 3.22-3.42 (m, 1H); 3.42-3.62 (m, 1H); 3.97 (t, J=6.7 Hz, 1H); 4.19 (q, J=7.2 Hz, 2H); 6.58 (d, J=8.4 Hz, 2H); 6.64 (d, J=8.4 Hz, 2H); 7.00-7.20 (aromatics, 3H); 7.22-7.40 (aromatics, 1H).

IR (neat) cm$^{-1}$: 3379, 2978, 2934, 1739, 1616, 1521.

Mass m/z (CI): 449 [M], 450 [M+1].

EXAMPLE 6

Ethyl 2-ethoxy-3-[4-{3-(4-(toluene-4-sulfonyloxy)phenyl) propylamino}phenyl]propionate

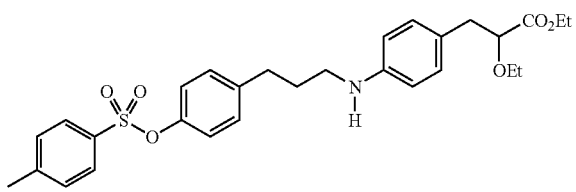

From 4-(3-(toluene-4-sulfonyloxy)propyl)phenyltoluene-4-sulfonate obtained in preparation 3 and ethyl 2-ethoxy-3-(4-aminophenyl)propionate obtained in preparation 5, the title compound was obtained as a viscous liquid (77%) following the procedure of Example 1.

$^1$H NMR (CDCl$_3$, 200 MHz): δ 1.16 (t, J=7.0 Hz, 3H); 1.22 (t, J=7.2 Hz, 3H); 1.88 (quintet, J=7.3 Hz, 2H); 2.43 (s, 3H); 2.67 (t, J=7.4 Hz, 2H); 2.89 (d, J=6.4 Hz, 2H); 3.08 (t, J=7.0 Hz, 2H); 3.25-3.45 (m, 1H); 3.45-3.65 (m, 1H); 3.94 (t, J=6.7 Hz, 1H); 4.15 (t, J=7.2 Hz, 2H); 6.48 (d, J=8.3 Hz, 2H); 6.87 (d, J=8.3 Hz, 2H); 6.95-7.15 (aromatics, 4H); 7.28 (d, J=8.3 Hz, 2H); 7.68 (d, J=8.3 Hz, 2H).

IR (neat) cm$^{-1}$: 3407, 2927, 1741, 1616, 1521, 1502.

Mass m/z (CI): 526 [M+1].

EXAMPLE 7

Ethyl 2-ethoxy-3-[3-{3-(4-methanesulfonyloxyphenyl)propylamino}phenyl]propionate

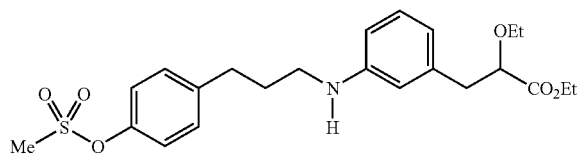

From 4-(3-methanesulfonyloxypropyl)phenylmethanesulfonate obtained in preparation 1 and ethyl 2-ethoxy-3-(3-aminophenyl)propionate obtained in preparation 7, the title compound was obtained as a viscus liquid (35%) following the procedure of Example 1.

$^1$H NMR (CDCl$_3$, 200 MHz): δ 1.16 (t, J=7.0 Hz, 3H); 1.22 (t, J=7.0 Hz, 3H); 1.92 (quintet, J=7.3 Hz, 2H); 2.73 (t, J=7.6 Hz, 2H); 2.92 (d, J=6.5 Hz, 2H); 3.02-3.22 (m, 5H); 3.22-3.42 (m, 1H); 3.42-3.62 (m, 1H); 4.00 (t, J=6.5 Hz, 1H); 4.16 (q, J=7.0 Hz, 2H); 6.40-6.62 (aromatics, 3H); 7.00-7.30 (aromatics, 5H).

IR (neat) cm$^{-1}$: 3406, 2978, 2934, 1740, 1606, 1503.

Mass m/z (CI): 450 [M+1], 449 [M].

EXAMPLE 8

Ethyl 2-isopropoxy-3-[4-{3-(4-methanesulfonyloxyphenyl)propylamino}phenyl]propionate

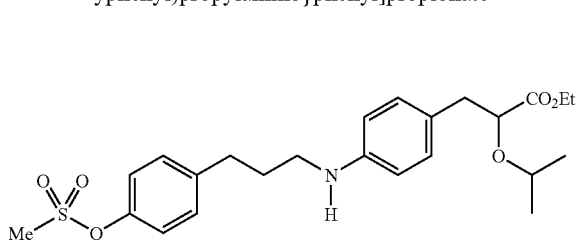

From 4-(3-methanesulfonyloxypropyl)phenylmethanesulfonate obtained in preparation 1 and ethyl 2-isopropoxy-3-(4-aminophenyl)propionate obtained in preparation 9, the title compound was obtained as a viscus liquid (47%) following the procedure of Example 1.

$^1$H NMR (CDCl$_3$, 200 MHz): δ 0.99 (d, J=6.0 Hz, 3H); 1.16 (d, J=6.3 Hz, 3H); 1.24 (t, J=7.3 Hz, 3H); 1.93 (quintet, J=7.3 Hz, 2H); 2.74 (t, J=7.8 Hz, 2H); 2.80-2.90 (m, 2H); 3.02-3.20 (m, 5H); 3.50 (apparent quintet, J=6.0 Hz, 1H); 3.99 (dd, J=7.8 and 5.3 Hz, 1H); 4.17 (q, J=7.3 Hz, 2H); 6.52 (d, J=8.3 Hz, 2H); 7.05 (d, J=8.3 Hz, 2H).

IR (neat) cm$^{-1}$: 3406, 2974, 2939, 1739, 1616, 1522.

Mass m/z (CI): 464 [M+1].

EXAMPLE 9

Ethyl 2-ethoxy-3-[4-(4-methanesulfonyloxyphenyl)phenyl]propionate

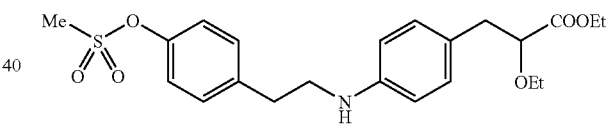

A mixture of ethyl 2-ethoxy-3-(4-aminophenyl)propionate (obtained in preparation 5) (0.3 g, 1.27 mmol) and anhydrous potassium carbonate (0.437 g, 3.16 mmol) were stirred in toluene (10 mL) at RT for 30 min. 4-(2-Methylsulfonyloxyethyl) phenyl methanesulfonate (0.484 g, 1.65 mmol), obtained from preparation 12, in toluene (5 mL) was added to the above reaction mixture drop wise followed by the addition of tetrabutyl ammonium bromide (81 mg, 0.25 mmol). The reaction mixture was stirred at 90° C. for 30 h. The reaction mixture was cooled to RT and was diluted with ethyl acetate (50 mL) and washed with water. The water layer was extracted with ethyl acetate (2×50 mL). The combined organic layers were washed with brine, dried (Na$_2$SO$_4$) and concentrated. The residue was purified on silica gel column using 20% ethyl acetate in pet ether to afford the title compound (0.24 g, 44%) as light yellow oil.

$^1$H NMR (200 MHz, CDCl$_3$): δ 1.17 (t, J=7.1 Hz, 3H); 1.24 (t, J=6.4 Hz, 3H); 2.91 (d, J=6.8 Hz, 2H); 2.93 (t, J=7.1 Hz, 2H); 3.15 (s, 3H); 3.32-3.3.44 (m, 3H); 3.50-3.67 (m, 1H); 3.96 (t, J=6.6 Hz, 1H); 4.18 (q, J=7.3 Hz, 2H); 6.59 (d, J=8.3 Hz, 2H); 7.08 (d, J=8.3 Hz, 2H); 7.19-7.30 (m, 4H).

Mass m/z (CI): 436 [M+1].

EXAMPLE 10

(S) Ethyl 2-ethoxy-3-[4-(4-methanesulfonyloxyphenylamino)phenyl]propanoate

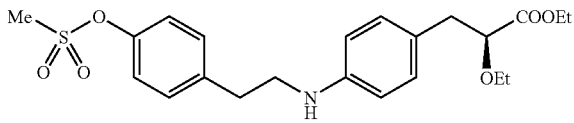

A mixture of (S) ethyl 2-ethoxy-3-(4-aminophenyl)propionate obtained in preparation 26 (2.5 g, 10.55 mmol) and anhydrous potassium carbonate (4.37 g, 31.65 mmol) were stirred in toluene (20 mL) at RT for 30 min. 4-(2-Methylsulfonyloxyethyl) phenyl methanesulfonate (4.03 g, 13.71 mmol), obtained from preparation 12, in toluene (10 mL) was added to the above reaction mixture drop wise followed by the addition of tetrabutyl ammonium bromide (0.34 g, 1.055 mmol). The reaction mixture was stirred at 90-100° C. for 30 h. The reaction mixture was cooled to RT and was diluted with ethyl acetate (100 mL) and washed with water. The water layer was extracted with ethyl acetate (2×50 mL). The combined organic layers were washed with brine, dried (Na2SO4) and concentrated. The residue was purified on silica gel column using 20% ethyl acetate in pet ether to afford the title compound (0.31 g, 6.7%) as yellow oil.

$^1$H NMR (200 MHz, CDCl$_3$): δ 1.17 (t, J=6.8 Hz, 3H); 1.26 (t, J=7.0 Hz, 3H); 2.88-3.02 (m, 4H); 3.15 (s, 3H); 3.28-3.3.45 (m, 3H); 3.50-3.70 (m, 1H); 3.95 (t, J=6.6 Hz, 1H); 4.17 (q, J=7.2 Hz, 2H); 6.67 (d, J=8.3 Hz, 2H); 7.10 (d, J=8.0 Hz, 2H); 7.18-7.30 (m, 4H).

Mass m/z (CI): 436 [M+1].

EXAMPLE 11

Ethyl 2-ethoxy-3-{4-[(E)-3-(4-methanesulfonyloxyphenyl)-2-propenylamino]phenyl}propionate

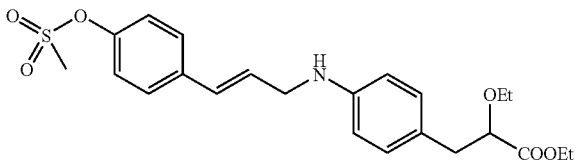

The title compound (150 mg, 28.4%) was obtained by following the same method as described in the example 9, from 4-[(E)-3-chloro-1-propenyl]phenyl methanesulfonate obtained in preparation 22 (0.43 g, 1.41 mmol) and Ethyl 2-ethoxy-3-(4-aminophenyl)propionate obtained in preparation 5 (0.28 g, 1.18 mmol), using potassium carbonate (489 mg, 3.54 mmol), tetrabutyl ammonium bromide (38 mg, 0.118 mmol) and toluene (25 mL) for 30 h.

$^1$H NMR (200 MHz, CDCl$_3$): δ 1.17 (t, J=7.1 Hz, 3H); 1.22 (t, J=7.1 Hz, 3H); 2.91 (d, J=6.3 Hz, 2H); 3.14 (s, 3H); 3.26-3.44 (m, 1H); 3.51-3.68 (m, 1H); 3.93 (d, J=6.3 Hz, 2H); 3.95 (t, J=6.6 Hz, 1H); 4.16 (q, J=7.1 Hz, 2H); 6.23-6.39 (m, 1H); 6.56-6.64 (m, 3H); 7.07 (d, J=8.3 Hz, 2H); 7.22 (d, J=8.3 Hz, 2H); 7.40 (d, J=8.3 Hz, 2H).

Mass m/z (CI): 402 [M+1−OEt].

EXAMPLE 12

(S) Ethyl 2-ethoxy-3-{4-[(E)-3-(4-methanesulfonyloxyphenyl)-2-propenylamino]phenyl}propionate

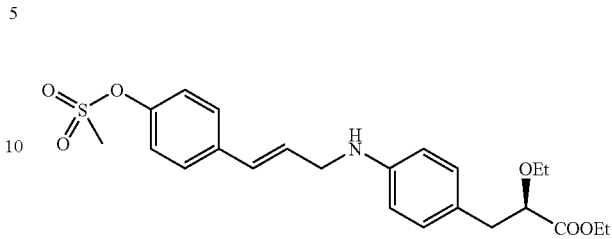

The title compound (5.2 g, 31.8%) was obtained by following the same method as described in the example 10, from from 4-[(E)-3-chloro-1-propenyl]phenyl methanesulfonate obtained in preparation 22 (15.90 g, 52.1 mmol) and (S) ethyl 2-ethoxy-3-(4-aminophenyl)propionate obtained in preparation 26 (9.5 g, 40.1 mmol) using potassium carbonate (16.6 g, 120.25 mmol) and tetrabutyl ammonium bromide (1.29 g, 4.01 mmol) and toluene (150 mL) for 24 h.

$^1$H NMR (200 MHz, CDCl$_3$): δ 1.17 (t, J=7.2 Hz, 3H); 1.22 (t, J=7.3 Hz, 3H); 2.90 (d, J=6.4 Hz, 2H); 3.13 (s, 3H); 3.26-3.44 (m, 1H); 3.51-3.68 (m, 1H); 3.90-4.00 (m, 3H); 4.16 (q, J=7.2 Hz, 2H); 6.28 (td, J =5.4 and 16.1 Hz, 1H); 6.57-6.64(m, 3H); 7.06 (d, J=8.3 Hz, 2H); 7.21 (d, J=8.6 Hz, 2H); 7.39 (d, J=8.6 Hz, 2H).

Mass m/z (CI): 448 [M$^+$+1]; 402 [M+1-OEt].

EXAMPLE 13

Methyl 2-ethoxy-3-[4-(4-methanesulfonyloxybenzylamino)phenyl]propionate

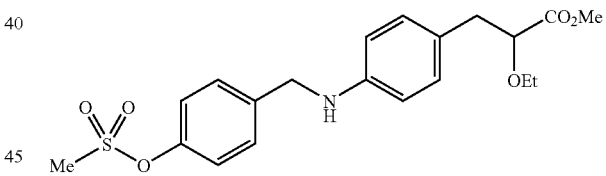

A mixture of 4-methanesulfonyloxybenzaldehyde (500 mg, 1 eq, 2.5 mmol) obtained in preparation 10, methyl 2-ethoxy-3-(4-aminophenyl)propionate (557 mg, 1 eq, 2.5 mmol), obtained in preparation 6, activated molecular sieves (4 A), and p-TsOH (43 mg, 0.1 eq, 0.25 mmol) in dry DCM (15 ml) were stirred at RT for 16 h. The reaction mixture was diluted with ethylacetate (100 ml), washed with aq. sodium bicarbonate, dried (Na$_2$SO$_4$), condensed (rotavapor), and dried under high vac. The crude mass was dissolved in dry methanol (15 ml) and conc HCl (250 μL) was added at 0° C., followed by NaB(CN)H$_3$ (188 mg, 1.2 eq, 3.0 mmol) in portions. The reaction mixture was stirred at 0° C. for 3 h, after that it was diluted with ethyl acetate (100 ml). The organic layer was washed with aq. sodium bicarbonate, dried (Na$_2$SO$_4$), and condensed. The residue was chromatographed using ethyl acetate and hexanes to obtain the title compound as thick oil (950 mg, 37%).

$^1$H NMR (CDCl$_3$, 200 MHz): δ 1.16 (t, J=6.9 Hz, 3H); 2.90 (d, J=6.8 Hz, 2H); 3.14 (s, 3H); 3.22-3.41 (m, 1H); 3.44-3.62 (m, 1H); 3.70 (s, 3H); 3.97 (t, J=6.6 Hz, 1H); 4.33

(s, 2H); 6.54 (d, J=8.3 Hz, 2H); 7.04 (d, J=8.3 Hz, 2H); 7.25 (d, J=8.3 Hz, 2H); 7.41 (d, J=8.3 Hz, 2H).
IR (neat) cm$^{-1}$: 3412, 2932, 1744, 1616, 1522, 1503.
Mass m/z (CI): 408 [M+1], 407[M].

EXAMPLE 14

(S)-2-Methoxy-3-[4-{3-(4-methanesulfonyloxyphenyl)propylamino}phenyl]propionic Acid

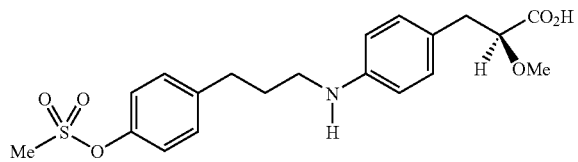

(S) Ethyl 2-methoxy-3-[4-{3-(4-methanesulfonyloxyphenyl) propylamino}phenyl]propionate (3.4 g, 1.0 eq, 7.8 mmol), obtained in Example 1, was hydrolyzed by treating with LiOH.H$_2$O (492 mg, 1.5 eq, 11.7 mmol) in MeOH-THF-water solvent mixture at RT for 3-4h. The reaction mixture was condensed, diluted with water and acidified (pH at 3) with aq. HCl. Desired acid was precipitated out from aqueous layer, which was then filtered out. If the precipitated acid was not pure enough by TLC, it was chromatographed using MeOH and CHCl$_3$ as eluents to obtain the pure acid as white solid (2.5 g, 79%).
Mp: 90-92° C.
[α]d: −16° (c 1.0, MeOH).
$^1$H NMR (CDCl$_3$, 200 MHz): δ 1.25 (s, 1H, N—H); 1.94 (quintet, 7.2 Hz, 2H); 2.72 (t, J=7.8 Hz, 2H); 2.82-3.02 (m, 2H); 3.02-3.18 (m, 5H); 3.38 (s, 3H); 3.97 (t, J=4.8 Hz, 1H); 4.90 (bs, CO$_2$H)); 6.58 (d, J=8.1 Hz, 2H); 7.05 (d, J=8.3 Hz, 2H); 7.15-7.24 (aromatics, 4H).
$^{13}$C NMR (CDCl$_3$, 50 MHz) δ: 29.53, 32.34, 37.15 (2C), 46.48, 57.58, 82.07, 116.31, 121.90, 129.75, 130.39, 140.57, 142.48, 147.33, 175.87.
IR (neat) cm$^{-1}$: 3046, 2932, 1732, 1615, 1520, 1365.
Mass m/z (CI): 408 [M+1], 407 [M].

EXAMPLE 15

2-Ethoxy-3-[4-{3-(4-methanesulfonyloxyphenyl)propylamino}phenyl]propionic Acid

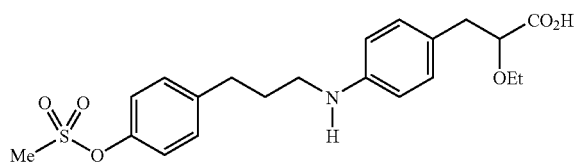

The title compound was obtained by hydrolyzing Ethyl 2-ethoxy-3-[4-{3-(4-methanesulfonyloxyphenyl) propylamino}phenyl]propionate obtained in Example 2 using LiOH.H$_2$O following the procedure described in Example 14.
Mp: 120-122° C.
$^1$H NMR (CDCl$_3$, 200 MHz): δ 1.18 (t, J=7.1 Hz, 3H); 1.25 (s, 1H, N—H); 1.93 (quintet, 6.9 Hz, 2H); 2.74 (t, J=7.5 Hz, 2H); 2.80-3.02 (m, 2H); 3.02-3.18 (m, 5H); 3.40-3.62 (m, 2H); 4.03 (dd, J=6.9, 4.4 Hz, 1H); 4.07 (bs, CO$_2$H)); 7.05 (d, J=8.3 Hz, 2H); 7.22 (d, J=8.3 Hz, 2H); 7.15-7.24 (aromatics, 4H).
IR (neat) cm$^{-1}$: 3389, 2925, 1616, 1502.
Mass m/z (CI): 422 [M+1].

EXAMPLE 16

2-Ethoxy-3-[4-{3-(4-methanesulfonyloxyphenyl)propyloxycarbonylamino}phenyl]propionic Acid

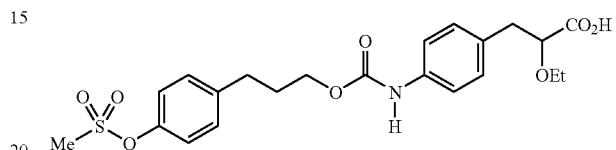

The title compound was obtained by hydrolyzing Ethyl 2-ethoxy-3-[4-{3-(4-methanesulfonyloxyphenyl) propyloxycarbonylamino}phenyl]propionate obtained in Example 4 using LiOH.H$_2$O following the procedure described in Example 14.
Obtained as a thick liquid.
$^1$H NMR (CDCl$_3$, 200 MHz): δ 1.19 (t, J=7 Hz, 3H; 2.01 (q, J=7 Hz, 2H; 2.75 (t, J=7.5 Hz, 2H; 2.90-3.10 (m, 2H); 3.13 (s, 3H); 3.35-3.55 (m, 1H); 3.55-3.75 (m, 1H); 4.08 (dd, J=7, 4.8 Hz, 1H); 4.21 (t, J=6.3 Hz, 2H); 6.85 (bs, NH); 7.10-7.35 (aromatics, 8H); 8.4 (bs, —COOH).
IR (neat) cm$^{-1}$: 3334, 3021, 2935, 1723, 1528

EXAMPLE 17

(S)-(-)-2-Ethoxy-3-[4-{3-(4-methanesulfonyloxyphenyl)propylamino}phenyl]propionic Acid

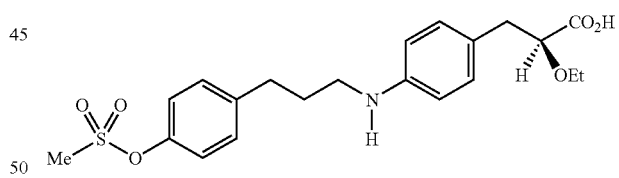

The desired compound was synthesized from (S) ethyl 2-ethoxy-3-[4-{3-(4-methanesulfonyloxyphenyl) propylamino}phenyl]propionate obtained in Example 3 by hydrolyzing with LiOH.H$_2$O following the procedure described in Example 14.
[α]$_D^{25}$: −16° (1.0, MeOH).
$^1$HNMR (CDCl$_3$, 200 MHz): δ 1.18 (t, J=7.1 Hz, 3H); 1.25 (s, 1H, N—H); 1.93 (quintet, 6.9 Hz, 2H); 2.74 (t, J=7.5 Hz, 2H); 2.80-3.02 (m, 2H); 3.02-3.18 (m, 5H); 3.40-3.62 (m, 2H); 4.03 (dd, J=6.9, 4.4 Hz, 1H); 4.07 (bs, CO$_2$H)); 7.05 (d, J=8.3 Hz, 2H); 7.22 (d, J=8.3 Hz, 2H); 7.15-7.24 (aromatics, 4H).
IR (neat) cm$^{-1}$: 3389, 2925, 1616, 1502.
Mass m/z (CI): 422 [M+1].

EXAMPLE 18

Ethoxy-3-[4-{3-(4-methanesulfonyloxyphenyl) propylamino}phenyl]propionic Acid

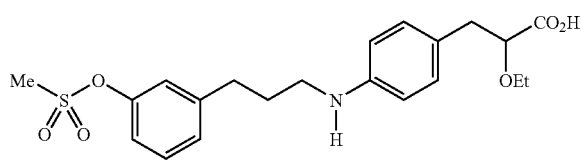

From ethyl 2-ethoxy-3-[4-{3-(3-methanesulfonyloxyphenyl) propylamino}phenyl] propionate (245 mg, 1.0 eq, 0.54 mmol), obtained in Example 5, the title compound was obtained as a thick liquid (73%) by hydrolyzing with LiOH.H$_2$O following the procedure described in Example 14.

$^1$H NMR (CDCl$_3$, 200 MHz): δ 1.19 (t, J=7.1 Hz, 3H); 1.25 (s, 1H, N—H); 1.90-2.02 (quintet, 6.9 Hz, 2H); 2.76 (t, J=7.9 Hz, 2H); 2.80-3.05 (m, 2H); 3.05-3.20 (m, 5H); 3.40-3.62 (m, 2H); 4.03 (dd, J=6.9 and 4.4 Hz, 1H); 4.60 (bs, CO$_2$H); 6.58 (d, J=8.3 Hz, 2H); 7.00-7.20 (aromatics, 5H); 7.22-7.29 (aromatics, 1H).

IR (neat) cm$^{-1}$: 3406, 2931, 1613, 1521.

Mass m/z (CI): 422 [M+1].

EXAMPLE 19

2-ethoxy-3-[4-{3-(4-(toluene-4-sulfonyloxy)phenyl) propylamino}phenyl]propionate

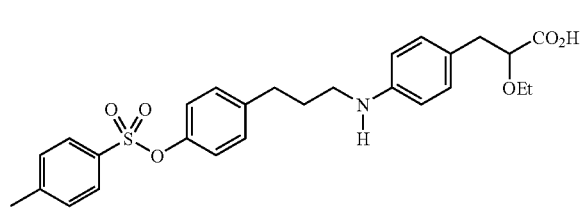

From ethyl 2-ethoxy-3-[4-{3-(4-(toluene-4-sulfonyloxy) phenyl) propylamino}phenyl]propionate (450 mg, 1.0 eq, 0.85 mmol), obtained in Example 6, the title compound was obtained as a white solid (310 mg, 72%) by hydrolyzing with LiOH.H$_2$O following the procedure described in Example 14.

Mp: 98-100° C.

$^1$H NMR (CDCl$_3$, 200 MHz) δ: 1.16 (t, J=6.8 Hz, 3H); 1.88 (quintet, J=7.3 Hz, 2H); 2.42 (s, 3H); 2.66 (t, J=6.9 Hz, 2H); 2.80-3.30 (m, 4H); 3.35-3.65 (m, 2H); 4.01 (dd, J 7.1, 4.4 Hz, 1H); 4.40 (bs, OH, NH); 6.53 (d, J=8.3 Hz, 2H); 6.86 (d, J=8.3 Hz, 2H); 7.00-7.10 (aromatics, 4H); 7.28 (d, J=8.3 Hz, 2H); 7.68 (d, J=8.3 Hz, 2H).

IR (neat) cm$^{-1}$: 3411, 2925, 1731, 1618, 1525, 1502.

Mass m/z (CI): 498 [M+1].

EXAMPLE 20

2-Ethoxy-3-[3-{3-(4-methanesulfonyloxyphenyl) propylamino}phenyl]propionic Acid

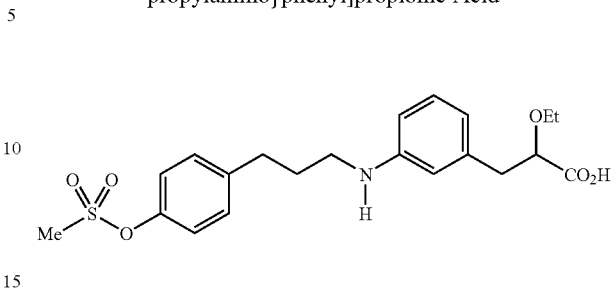

From ethyl 2-ethoxy-3-[3-{3-(4-methanesulfonyloxyphenyl) propylamino}phenyl]propionate (800 mg, 1.0 eq, 1.78 mmol), obtained in Example 7, the title compound was obtained as a thick liquid (500 mg, 67%) by hydrolyzing with LiOH.H$_2$O following the procedure described in Example 14.

$^1$H NMR (CDCl$_3$, 200 MHz) δ: 1.16 (t, J=7.0 Hz, 3H); 1.92 (quintet, 7.3 Hz, 2H); 2.73 (t, J=7.6 Hz, 2H); 2.90 (dd, J=14 and 7.5 Hz, 1H); 3.08 (dd, J=14, 4.3 Hz, 1H); 3.02-3.20 (m, 5H); 3.32-3.50 (m, 1H); 3.50-3.68 (m, 1H); 4.07 (dd, J=7.5, 4.3 Hz, 1H); 4.16 (q, J=7.0 Hz, 2H); 6.42-6.62 (aromatics, 3H); 7.00-7.30 (aromatics, 5H).

IR (neat) cm$^{-1}$: 3500, 3021, 2936, 1723, 1607, 1504.

Mass m/z (CI): 422 [M+1].

EXAMPLE 21

2-Isopropoxy-3-[4-{3-(4-methanesulfonyloxyphenyl)propylamino}phenyl]propionic Acid

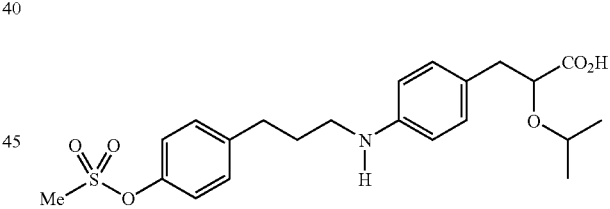

From ethyl 2-Isopropoxy-3-[4-{3-(4-methanesulfonyloxyphenyl) propylamino}phenyl]propionate (300 mg, 1.0 eq, 0.65 mmol), obtained in Example 8, the title compound was obtained as a white solid (74%) by hydrolyzing with LiOH.H$_2$O following the procedure described in Example 14.

Mp: 143-145° C.

$^1$H NMR (CDCl$_3$, 200 MHz) δ: 1.04 (d, J=6.3 Hz, 3H); 1.16 (d, J=6.0 Hz, 3H); 1.25 (s, 1H, NH); 1.93 (quintet, 7.3 Hz, 2H); 2.74 (t, J=7.8 Hz, 2H); 2.87 (dd, J=14.2 and 7.9 Hz, 1H); 3.01 (dd, J=14.1, 3.4 Hz, 1H); 3.05-3.20 (m, 5H); 3.55 (apparent quintet, J=6.0 Hz, 1H); 4.07 (dd, J=7.9 and 3.4 Hz, 1H); 4.17 (q, J=7.3 Hz, 2H); 4.90 (bs, CO$_2$H); 6.52 (d, J=8.3 Hz, 2H); 7.04 (d, J=8.3 Hz, 2H).

IR (neat) cm$^{-1}$: 3406, 2974, 2939, 1739, 1616, 1522.

Mass m/z (CI): 436 [M+1].

EXAMPLE 22

2-ethoxy-3-[4-(4-methanesulfonyloxybenzylamino) phenyl]propionic Acid

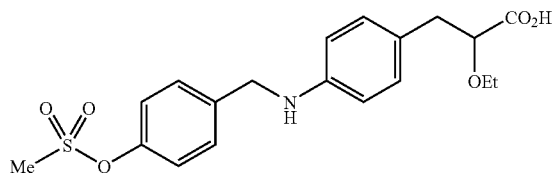

From methyl 2-ethoxy-3-[4-(4-methanesulfonyloxybenzylamino) phenyl]propionate (500 mg, 1.0 eq, 1.2 mmol), obtained in Example 13, the title compound was obtained as a viscus liquid (400 mg, 83%) by hydrolyzing with LiOH.H$_2$O following the procedure described in Example 14.

$^1$H NMR (CDCl$_3$, 200 MHz): δ 1.16 (t, J=6.8 Hz, 3H); 2.87 (dd, J=14.1 and 7.3 Hz, 1H); 2.99 (dd, J=14.1 and 4.4 Hz, 1H); 3.11 (s, 3H); 3.28-3.62 (m, 2H); 4.00 (dd, J=7.3, 4.4 Hz, 1H); 4.30 (s, 2H); 5.23 (bs, NH); 6.53 (d, J=8.3 Hz, 2H); 7.03 (d, J=8.3 Hz, 2H); 7.22 (d, J=8.3 Hz, 2H); 7.39 (d, J=8.3 Hz, 2H).

IR (neat) cm$^{-1}$: 3397, 2977, 2932, 1730, 1615, 1522, 1503.

Mass m/z: 393[M].

EXAMPLE 23

2-ethoxy-3-[4-(4-methanesulfonyloxyphenethylamino)phenyl]propionic Acid

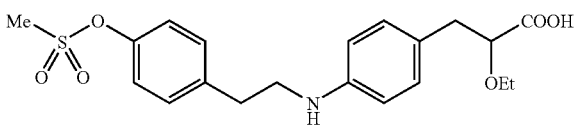

To a solution of ethyl 2-ethoxy-3-[4-(4-methylsulfonyloxyphenethylamino)-phenyl]propionate (0.22 g, 0.51 mmol), obtained from Example 9, in methanol (10 mL) sodium carbonate (268 mg, 2.53 mmol) in water (5 mL) was added at RT and stirred for 36 h at RT. Methanol was evaporated under reduced pressure and the residue was diluted with water (20 mL). The aqueous layer was washed with ethyl acetate (50 mL). The aqueous layer was acidified with 2N HCl to pH ~4 and extracted with ethyl acetate (2×50 mL). The organic layer was washed with brine, dried (Na$_2$SO$_4$) and concentrated. The residue was purified by column chromatography using 50% ethyl acetate in pet ether to yield the title compound (80 mg, 39%).

$^1$H NMR (200 MHz, CDCl$_3$): δ 1.19 (t, J=6.8 Hz, 3H); 2.82-3.05 (m, 4H); 3.15 (s, 3H); 3.40 (t, J=7.2 Hz, 3H); 3.45-3.62 (m, 1H); 4.01-4.10 (m, 1H); 6.63 (d, J=8.3 Hz, 2H); 7.08 (d, J=8.4 Hz, 2H); 7.18-7.30 (m, 4H).

Mass m/z (CI): 408 [M+1].

EXAMPLE 24

(S)-2-ethoxy-3-[4-(4-methanesulfonyloxyphenethylamino)phenyl]propionic Acid

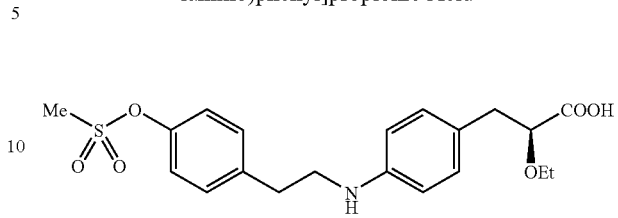

The title compound was obtained (180 mg, 56.6%) from ethyl (S)-2-ethoxy-3-[4-(4-methylsulfonyloxyphenethylamino)-phenyl]propionate (0.34 g, 0.78 mmol), obtained from example 10, by hydrolyzing in methanol (5 mL) using sodium carbonate (414 mg, 3.91 mmol) in water (5 mL) at RT for 24 h following the same procedure as described in the Example 23.

$^1$H NMR (200 MHz, CDCl$_3$): δ 1.19 (t, J=7.0 Hz, 3H); 2.84-3.03 (m, 4H); 3.14 (s, 3H); 3.39 (t, J=7.0 Hz, 3H); 3.42-3.61 (m, 2H); 4.04 (dd, J=4.4 and 7.1 Hz, 1H); 6.55 (d, J=8.3 Hz, 2H); 7.05 (d, J=8.3 Hz, 2H); 7.22-7.27 (m, 4H).

Mass m/z (CI): 408 [M+1].

EXAMPLE 25

(S)-2-Ethoxy-3-{4-[(E)-3-(4-methanesulfonyloxyphenyl)-2-prope-nylamino]phenyl}propionic Acid

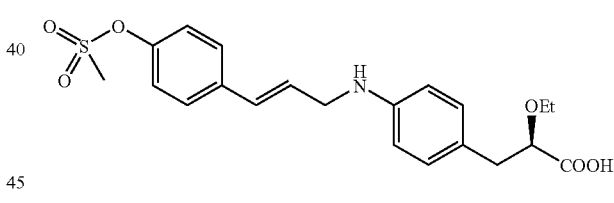

The title compound was synthesized by hydrolyzing ethyl 2-ethoxy-3-{4-[(E)-3-(4-methylsulfonyloxyphenyl)-2-propenylamino]-phenyl}propionate obtained in Example 12 (4 g, 8.95 mmol) in methanol-THF-water (45:4:9, 58 mL) using lithium hydroxide (563 mg, 13.42 mmol) following the same procedure as described in the Example 14 (1.2 g, 32%).

[α]$_D^{25}$=−18° (c 0.1, MeOH).

Mp: 156-158° C.

$^1$H NMR (CD$_3$OD, 200 MHz): δ 1.11 (t, J=6.8 Hz, 2H); 2.74-2.98 (m, 2H); 3.19 (s, 3H); 3.25-3.70 (m, 2H); 3.88-4.02 (m, 3H); 6.36 (td, J=16.1 and 5.4 Hz, 1H); 6.62-6.75 (m, 3H); 7.02 (d, J=7.8 Hz, 2H); 7.24 (d, J=8.3 Hz, 2H); 7.45 (d, J=8.8 Hz, 2H).

Mass m/z (ES): 420 [M+1].

EXAMPLE 26

Ethyl 2-ethoxy-3-[4-(4-methanesulfonyloxycarboxamido)phenyl]propionate

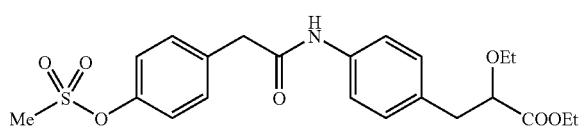

To a cooled solution of 2-(4-methylsulfonyloxyphenyl) acetic Acid (0.53 g, 2.3 mmol), obtained in preparation 14, in DCM (25 mL) HOBt (311 mg, 2.30 mmol) was added slowly followed by the addition of EDC (442 mg, 2.30 mmol) and the mixture was stirred for 10 min. A solution of ethyl 2-ethoxy-3-(4-aminophenyl) propionate (601 mg, 2.535 mmol), obtained in preparation 5, in DCM (5 mL) was added to the above reaction mixture and stirred at RT for 18 h. The reaction mixture was diluted with DCM and washed with saturated NaHCO$_3$ solution, water and brine, dried (Na$_2$SO$_4$) and concentrated. The residue was purified by column chromatography using ethyl acetate-pet ether (1:3) to afford the title compound (710 mg, 69%).

$^1$H NMR (200 MHz, CDCl$_3$): δ 1.13 (t, J=7.1 Hz, 3H); 1.23 (t, J=7.1 Hz, 3H); 2.95 (d, J=5.9 Hz, 2H); 3.16 (s, 3H); 3.21-3.41 (m, 1H); 3.51-3.67 (m, 1H); 3.71 (s, 2H); 3.95 (t, J=6.6 Hz, 1H); 4.16 (q, J=6.8 Hz, 2H); 7.09-7.43 (m, 8H).

Mass m/z (CI): 450 [M+1].

EXAMPLE 27

2-Ethoxy-3-{4-[(E)-3-(4-methanesulfonyloxyphenyl)-2-propenylamino]phenyl}propionic Acid

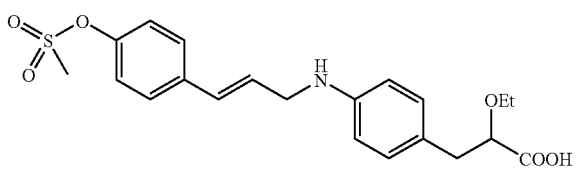

The title compound was synthesized by hydrolyzing ethyl 2-ethoxy-3-{4-[(E)-3-(4-methylsulfonyloxyphenyl)-2-propenylamino]-phenyl}propionate obtained in example 11 (140 mg, 0.313 mmol) in methanol-water (2:1, 6 mL) using lithium hydroxide (17 mg, 0.407 mmol) following the same procedure as described in the Example 14 (40 mg, 30.5%).

Mp: 146-148° C.

$^1$H NMR (200 MHz, CDCl$_3$): δ 1.12 (t, J=6.6 Hz, 3H); 2.72-3.00 (m, 2H); 3.20 (s, 3H); 3.25-3.42 (m, 2H); 3.50-3.68 (m, 1H); 3.88-4.00 (m, 2H); 6.30-6.48 (m, 1H); 6.60-6.70 (m, 3H); 7.04 (d, J=7.3 Hz, 2H); 7.25 (d, J=7.8 Hz, 2H); 7.47 (d, J=8.3 Hz, 2H).

EXAMPLE 28

2-Ethoxy-3-[4-(4-methanesulfonyloxybenzylcarboxamido)phenyl]propionic Acid

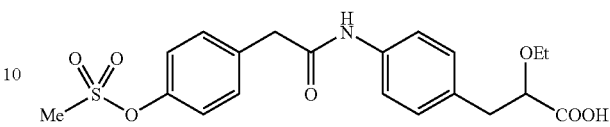

The title compound was obtained (220 mg, 33.5%) as white solid from Ethyl 2-ethoxy-3-[4-(4-methylsulfonyloxybenzylcarboxamido)phenyl]-propionate obtained in example 26 (0.7 g, 1.56 mmol) by hydrolyzing in methanol-water (3:1, 20 mL) using sodium carbonate for 60 h at room temperature following the method as described in Example 23.

Mp: 162-164° C.

$^1$H NMR (200 MHz, CDCl$_3$+DMSO-d$_6$): δ 1.14 (t, J=7.0 Hz, 3H); 2.84-3.10 (m, 2H); 3.15 (s, 3H); 3.25-3.40 (m, 1H); 3.55-3.67 (m, 1H); 3.70 (s, 2H); 3.95 (dd, J=4.7 and 7.9 Hz, 1H); 7.18-7.52 (m, 8H).

Mass m/z (CI): 422 [M+1].

EXAMPLE 29

Ethyl 2-ethoxy-3-[4-{3-(4-tert-butoxy-4-methylsulfonamidophenyl) propylamino}phenyl]propionate

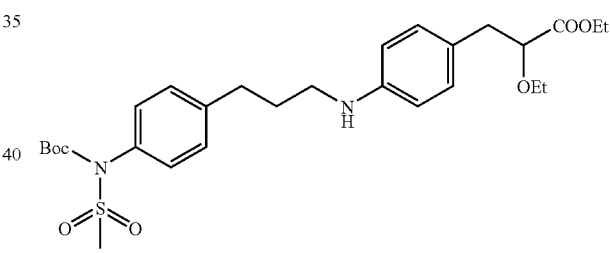

Ethyl 2-ethoxy-3-(4-aminophenyl)propionate obtained in preparation 5 (0.29 g, 1.22 mmol) and potassium carbonate (506 mg, 3.67 mmol) were stirred in toluene (20 mL) at room temperature for 30 min. 3-(4-tert-Butoxy-4-methylsulfonamidophenyl)propyl methanesulfonate obtained in preparation 19, (0.6 g, 1.47 mmol) in toluene (10 mL) was added drop wise followed by the addition of tetrabutyl ammonium bromide (39 mg, 0.122 mmol). The reaction mixture was stirred for 40 h at 90-100° C. The reaction mixture was cooled to rt and diluted with EtOAc (100 mL) and washed with water. The water layer was extracted with ethyl acetate and the combined organic layer was washed with brine, dried (Na$_2$SO$_4$) and evaporated. The residue was purified on silica gel to give the title compound (190 mg, 28.3%).

$^1$H NMR (200 MHz, CDCl$_3$): δ 1.16 (t, J=6.8 Hz, 3H); 1.26 (t, J=7.2 Hz, 3H); 1.50 (s, 9H); 1.64-1.82 (m, 2H); 2.59 (t, J=7.6H, 2H); 2.84 (s, 3H); 3.02 (d, J=6.7 Hz, 2H); 3.26-3.42 (m, 1H); 3.55-3.70 (m, 3H); 4.02 (t, J=6.6 Hz, 1H); 4.19 (q, J=6.2 Hz, 2H); 6.39 (bs, 1H, D$_2$O exchangeable); 7.00 (d, J=8.3 Hz, 2H); 7.20-7.34 (m, 6H).

Mass m/z (CI): 548 [M].

EXAMPLE 30

2-Ethoxy-3-[4-{3-(4-tert-butoxy-4-methylsulfonamidophenyl) propylamino}-phenyl]propionic Acid

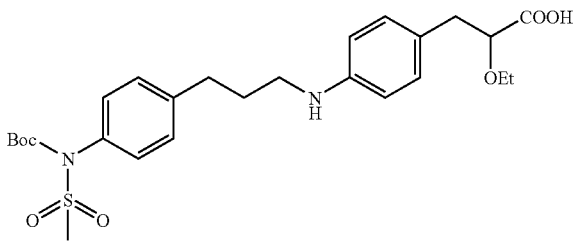

Ethyl 2-ethoxy-3-[4-{3-(4-tert-butoxy-4-methylsulfonamidophenyl)propylamino}-phenyl]propionate (180 mg, 0.33 mmol), obtained in Example 29, was hydrolyzed by treating with LiOH.H$_2$O (18 mg, 0.43 mmol) in MeOH-water (2:1) solvent mixture (6 mL) at RT for overnight. The reaction mixture was condensed, diluted with water and acidified to pH ~4 with aqueous HCl. Finally the crude acid was extracted out by ethyl acetate. Ethyl acetate layer was dried (Na$_2$SO$_4$), condensed, and chromatographed using ethyl acetate—pet ether (1:1) to obtain the desired compound (140 mg, 82%) as white solid.

Mp: 78-80° C.

$^1$H NMR (200 MHz, CDCl$_3$): δ 1.21 (t, J=6.8 Hz, 3H); 1.51 (s, 9H); 1.70-1.88 (m, 2H); 2.60 (t, J=7.3H, 2H); 2.85 (s, 3H); 3.00-3.22 (m, 2H); 3.38-3.70 (m, 4H); 4.08-4.20 (m, 1H); 6.48 (bs, 1H, D$_2$O exchangeable); 7.97 (d, J=8.3 Hz, 2H); 7.20-7.35 (m, 6H).

EXAMPLE 31

Ethyl 2-ethoxy-3-{4-[(E)-2-(4-methylsulfonyloxyphenyl)-1-ethenylcarboxami-do]phenyl}propionate

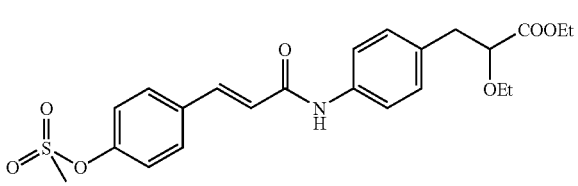

The title compound was prepared (0.24 g, 25.2%) from (E)-3-(4-methylsulfonyloxyphenyl)-2-propenoic acid (0.5 g, 2.07 mmol), obtained in preparation 23, HOBt (279 mg, 2.07 mmol), EDC (396 mg, 2.07 mmol) and ethyl 2-ethoxy-3-(4-aminophenyl)propionate (539 mg, 2.273 mmol), obtained in preparation 5, using DCM (25 mL) at RT for 48 h following the same procedure as described in the Example 26.

$^1$H NMR (200 MHz, CDCl$_3$): δ 1.17 (t, J=7.0 Hz, 3H); 1.27 (t, J=7.1 Hz, 3H); 3.00 (d, J=6.2 Hz, 2H); 3.19 (s, 3H); 3.28-3.45 (m, 1H); 3.55-3.70 (m, 1H); 4.01 (t, J=6.6 Hz, 1H); 4.16 (q, J=6.3 Hz, 2H); 6.54 (d, J=15.3 Hz, 1H); 7.20-7.35 (m, 4H); 7.50-7.60 (m, 4H); 7.72 (d, J=15.6 Hz, 1H).

Mass m/z (CI): 462 [M+1].

EXAMPLE 32

2-Ethoxy-3-{4-[(E)-2-(4-methylsulfonyloxyphenyl)-1-ethenylcarboxamido]-phenyl}propionic Acid

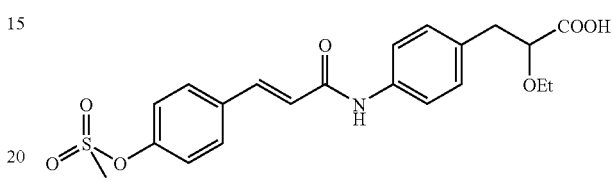

The title compound was obtained as white solid (35 mg, 18.6%); mp: 178-180° C.; by hydrolyzing ethyl 2-ethoxy-3-{4-[(E)-2-(4-methylsulfonyloxyphenyl)-1-ethenylcarboxamido]phenyl}propionate obtained from example 31, in methanol (10 mL) using sodium carbonate (230 mg, 2.17 mmol) in water (5 mL) at RT for 48 h following the same method as described in the Example 23.

$^1$H NMR (200 MHz, CDCl$_3$): δ 1.15 (t, J=7.0 Hz, 3H); 2.84-3.10 (m, 2H); 3.22 (s, 3H); 3.22-3.42 (m, 1H); 3.55-3.72 (m, 1H); 3.97 (dd, J=4.8 and 8.0 Hz, 1H); 6.80 (d, J=15.6 Hz, 1H); 7.20-7.35 (m, 4H); 7.50-7.70 (m, 5H).

Mass m/z (CI): 434 [M+1].

EXAMPLE 33

Ethyl 2-ethoxy-3-[4-(4-methylsulfonyloxyphenethylcarboxamido)phenyl]-propionate

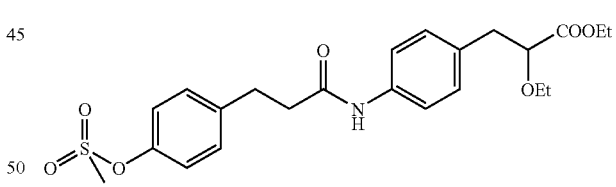

The title compound was prepared as white solid (0.5 g, 52.7%); mp: 90-92° C.; from 3-(4-methylsulfonyloxyphenyl)propionic acid (0.5 g, 2.049 mmol), obtained in preparation 24, HOBt (277 mg, 2.049 mmol), EDC (393 mg, 2.049 mmol) and ethyl 2-ethoxy-3-(4-aminophenyl)propionate (534 mg, 2.254 mmol), obtained in preparation 5, using DCM (25 mL) at RT for 20 h following the same procedure as described in the Example 26.

$^1$H NMR (200 MHz, CDCl$_3$): δ 1.15 (t, J=7.0 Hz, 3H); 1.24 (t, J=7.5 Hz, 3H); 2.64 (t, J=7.5 Hz, 2H); 2.96 (d, J=6.4 Hz, 2H); 3.07 (t, J=7.5 Hz, 2H); 3.12 (s, 3H); 3.25-3.42 (m, 1H); 3.52-3.66 (m, 1H); 3.97 (t, J=6.4 Hz, 1H); 4.17 (q, J=7.2 Hz, 2H); 7.18-7.42 (m, 8H).

Mass m/z (CI): 464 [M+1].

EXAMPLE 34

2-Ethoxy-3-[4-(4-methylsulfonyloxyphenethyl-carboxamido)phenyl]-propaionic Acid

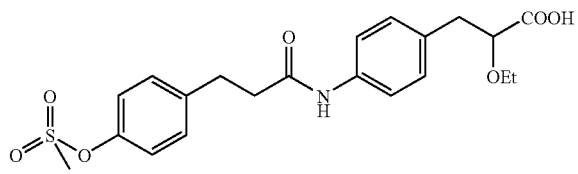

The title compound was obtained as white solid (70 mg, 23%); mp: 164-166° C.; by hydrolyzing ethyl 2-ethoxy-3-[4-(4-methylsulfonyloxyphenethenylcarboxamido)phenyl] propionate obtained from Example 33, in methanol (10 mL) using sodium carbonate (372 mg, 3.51 mmol) in water (5 mL) at RT for 24 h following the same method as described in the Example 23.

$^1$H NMR (200 MHz, CDCl$_3$): δ 1.13 (t, J=7.1 Hz, 3H); 2.54-2.70 (m, 2H); 2.88-3.10 (m, 4H); 3.12 (s, 3H); 3.22-3.40 (m, 11H); 3.52-3.72 (m, 1H); 3.94 (dd, J=4.9 and 7.8 Hz, 1H); 7.12-7.50 (m, 8H).

EXAMPLE 35

2-Ethoxy-3-[4-{3-(4-methanesulfonyloxyphenyl) propylamino}phenyl]propionic Acid and Arginine Salt

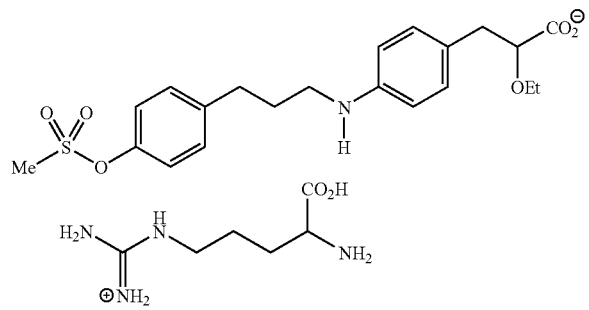

2-Ethoxy-3-[4-{3-(4-methanesulfonyloxyphenyl) propylamino}phenyl]propionic Acid (100 mg, 1 eq, 0.237 mmol) obtained in Example 15 and L-arginine (41.2 mg, 1 eq, 0.237 mmol) were taken in dry methanol (3 ml) and stirred at RT for 2-3 h. The solvent was removed on rotavapour followed by benzene azeotrope. The residue was dried under high vacuum pump to yield the title compound as a free flowing solid (yield 100%).

Mp: 85-87° C.

$^1$H NMR (DMSO-d$_6$, 200 MHz): δ 1.02 (t, J=6.8 Hz, 3H); 1.24 (s, 1H, N—H); 1.50-1.90 (m, 6H); 2.55-3.22 (m, 10H); 3.32 (s, 3H); 3.42-3.65 (m, 2H); 6.43 (d, J=8.1 Hz, 2H); 6.92 (d, J=8.1 Hz, 2H); 7.24 (d, J=8.6 Hz, 2H); 7.32 (d, J=8.6 Hz, 2H); 8.18 (bs, D$_2$O exchangeable).

EXAMPLE 36

2-ethoxy-3-[4-{3-(4-methanesulfonyloxyphenyl) propyloxycarbonylamino}phenyl]propionic Acid and Arginine Salt

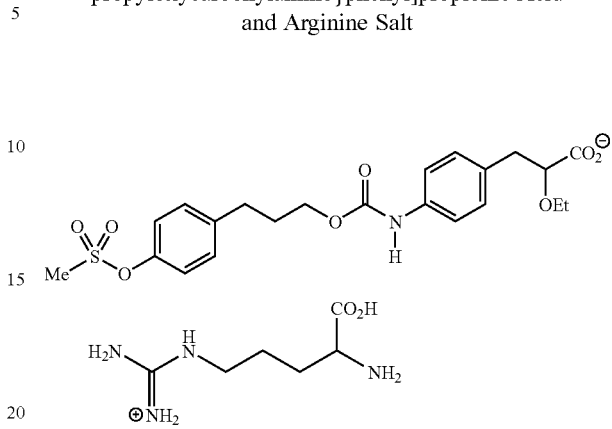

The title compound was obtained from 2-Ethoxy-3-[4-{3-(4-methanesulfonyloxyphenyl) propyloxycarbonylamino}phenyl] propionic Acid obtained in Example 16 and L-arginine following procedure of Example 35.

Mp: 180-82° C.

EXAMPLE 37

2-Ethoxy-3-[4-{3-(3-methanesulfonyloxyphenyl) propylamino}phenyl]propionic Acid and Arginine Salt

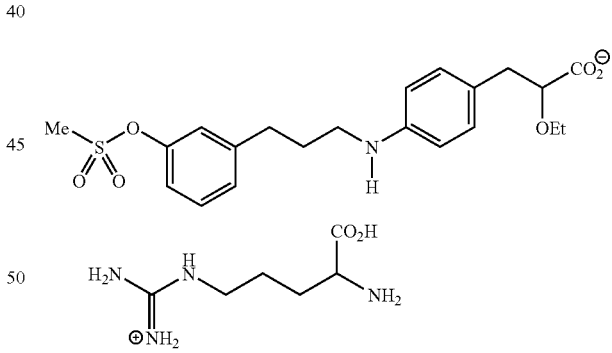

From 2-ethoxy-3-[4-{3-(3-methanesulfonyloxyphenyl) propylamino}phenyl]propionic Acid (95 mg, 0.22 mmol) obtained in example 18 and L-arginine (39.3 mg, 0.22 mmol), the title compound was obtained as a free flowing solid (100%) following procedure of Example 35.

Mp: 80-82° C.

$^1$H NMR (DMSO-d$_6$, 200 MHz): δ 0.99 (t, J=6.8 Hz, 3H); 1.50-1.90 (m, 7H); 2.55-3.30 (m, 10H); 3.35 (s, 3H); 3.42-3.65 (m, 2H); 5.36 (bs, D$_2$O-exchangable); 6.43 (d, J=8.1 Hz, 2H); 6.92 (d, J=8.1 Hz, 2H); 7.10-7.30 (aromatics, 3H); 7.30-7.40 (aromatics, 1H); 8.18 (bs, D$_2$O exchangeable).

EXAMPLE 38

2-Ethoxy-3-[4-(4-methanesulfonyloxybenzylamino) phenyl]propionic Acid and Arginine Salt

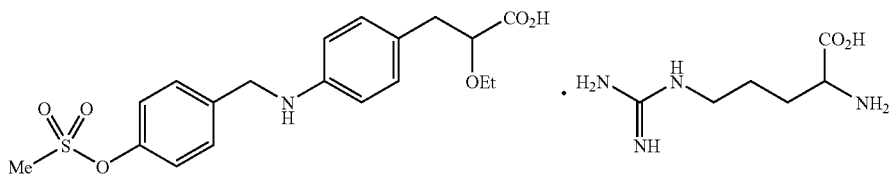

From 2-ethoxy-3-[4-(4-methanesulfonyloxybenzylamino)phenyl]propionic Acid (140 mg, 0.35 mmol) obtained in example 22 and L-arginine (68 mg, 0.35 mmol), the title compound was obtained as a free flowing solid (yield 100%) following procedure of Example 35.

Mp: 138-140° C.

$^1$H NMR (DMSO-d$_6$, 200 MHz): δ 0.98 (t, J=6.7 Hz, 3H); 1.42-1.82 (m, 4H); 2.55-3.60 (m, 8H); 3.34 (s, 3H); 4.23 (s, 1H); 4.26 (s, 1H); 6.06 (bs, 1H); 6.45 (d, J=8 Hz, 2H); 6.90 (d, J=8.1 Hz, 2H); 7.28 (d, J=8.6 Hz, 2H); 7.45 (d, J=8.6 Hz, 2H); 8.18 (bs, D$_2$O exchangeable).

EXAMPLE 39

2-Ethoxy-3-[3-{3-(4-methanesulfonyloxyphenyl) propylamino}phenyl]propionic Acid and Arginine Salt

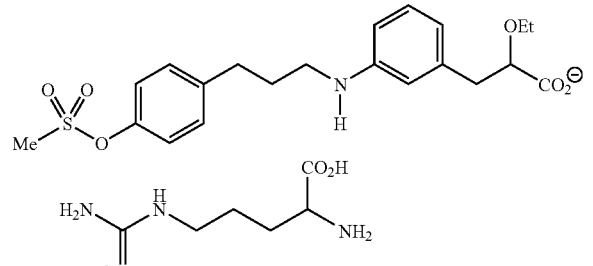

From 2-ethoxy-3-[3-{3-(4-methanesulfonyloxyphenyl) propylamino}phenyl]propionic Acid (200 mg, 0.475 mmol) obtained in example 20 and L-arginine (83 mg, 0.475 mmol), the title compound was obtained as a free flowing solid (yield 100%) following procedure of Example 35.

Mp: 162-164° C.

EXAMPLE 40

Magnesium Salt of 2-ethoxy-3-[4-(4-methanesulfonyloxyphenethylamino)-phenyl]propionic Acid

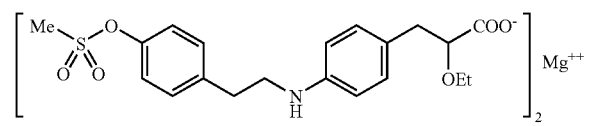

To a solution of 2-ethoxy-3-[4-(4-methylsulfonyloxyphenethylamino)phenyl]propionic acid (70 mg, 171 μmol), obtained from example 23, in methanol (5 mL) Mg(OH)$_2$ (5 mg) was added and refluxed for 24 h. Methanol was evaporated off and the residue was flushed with toluene to give the title compound (50 mg, 68%) as a white solid.

Mp: 130-134° C.

$^1$H NMR (200 MHz, CD$_3$OD): δ 1.10 (t, J=6.8 Hz, 3H); 2.70-2.96 (m, 4H); 3.18 (s, 3H); 3.22-3.40 (m, 3H); 3.50-3.66 (m, 1H); 3.78-3.91 (m, 1H); 6.58 (d, J=8.3 Hz, 2H); 7.05 (d, J=8.3 Hz, 2H); 7.23 (d, J=8.8 Hz, 2H); 7.32 (d, J=8.3 Hz, 2H).

EXAMPLE 41

Magnesium Salt of (S)-2-ethoxy-3-[4-(4-methanesulfonyloxyphenethylamino)-phenyl]propionic acid

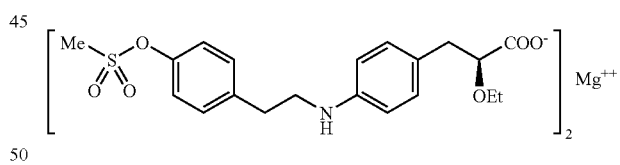

To a solution of (S)-2-ethoxy-3-[4-(4-methylsulfonyloxyphenethylamino)phenyl]-propionic acid (170 mg, 418 μmol), obtained in Example 24, in methanol (10 mL) Mg(OH)$_2$ (12 mg) was added and refluxed for 20 h. Methanol was evaporated off and the residue was flushed with toluene to give the title compound (135 mg) as a white solid.

Mp: 134-138° C.

$[α]_D^{25}$=−26.8° (c 0.5, MeOH)

$^1$H NMR (200 MHz, CD$_3$OD): δ 1.10 (t, J=7.0 Hz, 3H); 2.70-2.95 (m, 4H); 3.18 (s, 3H); 3.22-3.40 (m, 3H); 3.50-3.70 (m, 1H); 3.78-3.90 (m, 1H); 6.57 (d, J=8.1 Hz, 2H); 7.05 (d, J=8.3 Hz, 2H); 7.23 (d, J=8.6 Hz, 2H); 7.32 (d, J=8.3 Hz, 2H).

Mass m/z (ES): 837.2 [M+1].

EXAMPLE 42

(S) Ethyl 2-methoxy-3-[4-{(E)-3-(4-methanesulfonyloxyphenyl)-2-propenylamino}phenyl]propionate

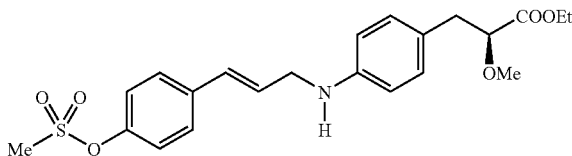

The title compound was obtained following the procedure of example 9, by reacting compound obtained in preparation 22 (892 mg, 2.91 mmole) and (S) ethyl 2-methoxy-3-(4-aminophenyl)propionate obtained in preparation 27 (500 mg, 2.24 mmole) using $K_2CO_3$ (928 mg, 6.72 mmole) and tetrabutyl ammonium bromide (72 mg, 0.22 mmole) heating in toluene for 16 h. (Yield 300 mg, 31%).

$^1$H NMR (200 MHz, CDCl$_3$): δ 1.23 (t, J=7.2 Hz, 3H); 2.91 (d, J=6.4 Hz, 2H); 3.13 (s, 3H); 3.52 (s, 3H); 3.82-3.98 (m, 2H); 4.03-4.21 (m, 3H); 6.30 (td, J=5.4 and 15.8 Hz, 1H; 6.54-6.65 (m, 3H); 7.05 (d, J=8.3 Hz, 2H); 7.22 (d, J=8.9 Hz, 2H); 7.40 (d, J=8.6 Hz, 2H).

Mass m/z (CI): 434 [M+1].

EXAMPLE 43

(S)-2-Methoxy-3-[4-{(E)-3-(4-methanesulfonyloxyphenyl)-2-propenylamino}phenyl]propionic Acid

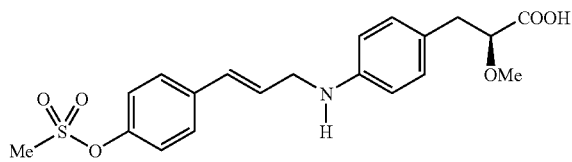

The title compound was obtained as pale yellow solid from the compound obtained in Example 42 (300 mg, 0.69 mmole) using LiOH.H$_2$O (44 mg, 1.04 mmole) in methanol-water (3.5 ml) at room temperature for 5 h following the procedure described in Example 14. (620 mg, 51%).

Mp: 116-118° C.

$^1$H NMR (200 MHz, DMSO d$_6$): δ 2.75 (t, J=7.3 Hz, 2H); 3.20 (s, 3H); 3.34 (s, 3H); 3.75-3.92 (m, 3H); 6.40-6.63 (m, 4H); 6.92 (d, J=8.3 Hz, 2H); 7.28 (d, J=8.6 Hz, 2H); 7.51 (d, J=8.6 Hz, 2H).

Mass m/z (ES): 406 [M+1].

EXAMPLE 44

(S) Ethyl 2-methoxy-3-[4-{3-(3-methanesulfonyloxyphenyl) propenylamino}phenyl]propanoate

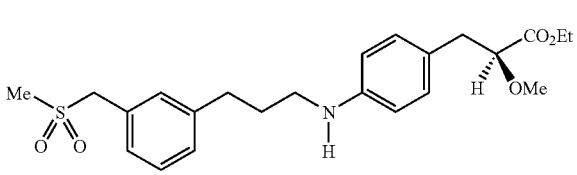

Starting from 3-(3-methanesulfonyloxypropyl)phenylmethanesulfonate, (911 mg, 2.95 mmol, 1.1 eq), obtained in preparation 2, and (S) ethyl 2-methoxy-3-(4-aminophenyl) propionate, (600 mg, 2.69 mmol, 1.0 eq), obtained in preparation 27, the title compound was obtained as thick liquid (220 mg, 35%) following the procedure described in Example 1.

$^1$H NMR (CDCl$_3$, 200 MHz) δ: 1.23 (t, J=7.2 Hz, 3H); 1.92 (quintet, 7.0 Hz, 2H); 2.75 (t, J=7.0 Hz, 2H); 2.90 (d, J=6.7 Hz, 2H); 3.02-3.20 (m, 5H); 3.34 (s, 3H); 3.89 (t, J=6.7 Hz, 1H); 4.17 (q, J=7.2 Hz, 2H); 6.50 (d, J=8.3 Hz, 2H); 7.02 (d, J=8.3 Hz, 2H); 7.10-7.40 (aromatics, 4H).

IR (neat) cm$^{-1}$: 3405, 2935, 1739, 1615, 1376.

Mass m/z(CI): 436 [M+1].

EXAMPLE 45

(S) 2-Methoxy-3-[4-{3-(3-methanesulfonyloxyphenyl)propylamino}phenyl]propionic Acid

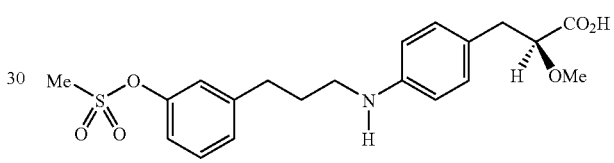

(S) Ethyl 2-methoxy-3-[4-{3-(3-methanesulfonyloxyphenyl)propylamino}phenyl]propanoate, (220 mg, 1.0 eq, 0.50 mmol), obtained in Example 44, was hydrolyzed following the procedure of Example 14, to obtain the desired acid (170 mg, 83%) as thick liquid after purification using column chromatography.

$^1$H NMR (CDCl$_3$, 400 MHz) δ: 1.94 (quintet, 7.0 Hz, 2H); 2.75 (t, J=7.0 Hz, 2H); 2.92 (dd, J=14, 7.3 Hz, 1H); 3.03 (dd, J=14, 4.3 Hz, 1H); 3.10-3.18 (m, 5H); 3.40 (s, 3H); 3.96 (dd, J=7.3, 4.3 Hz, 1H); 4.40 (bs, NH, CO$_2$H)); 6.53 (d, J=8.3 Hz, 2H); 7.04 (d, J=8.3 Hz, 2H); 7.11-7.35 (aromatics, 4H).

IR (neat) cm$^{-1}$: 3380, 2924, 1739, 1611, 1522, 1364.

Mass m/z(ES): 408 [M+1], 430 [M+Na$^+$], 815 [M$_2$+1].

EXAMPLE 46

(S) 2-Methoxy-3-[4-{3-(3-methanesulfonyloxyphenyl)propylamino}phenyl]propionic Acid Arginine Salt

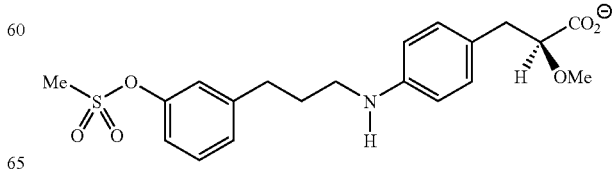

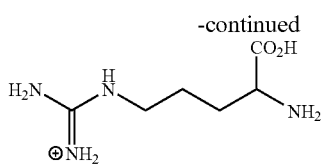

The title compound was obtained from (S) 2-Methoxy-3-[4-{3-(3-methanesulfonyloxyphenyl)propylamino}phenyl]propanoic acid obtained in Example 45 (170 mg, 1 eq, 0.41 mmol), and L-arginine (73 mg, 1 eq, 0.41 mmol) as a free flowing solid (yield 100%) following the procedure described in Example 35.

Mp: 110-112° C.

EXAMPLE 47

(S) Ethyl 2-ethoxy-3-{4-[(E)-3-(4-methylsulfonyloxyphenyl)-2-propenyl(phenyl)carboxamido]phenyl}propionate

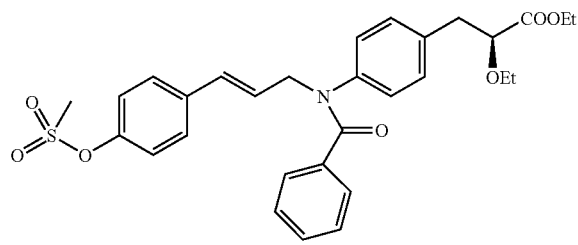

To a solution of (S) Ethyl 2-ethoxy-3-{4-[(E)-3-(4-methylsulfonyloxyphenyl)-2-propenylamino]phenyl}propionate obtained in Example 12 (0.2 g, 0.447 mmol) and potassium carbonate (0.185 g, 1.34 mmol) in dry DMF (3 ml) at RT was added benzoyl chloride (62 μl, 0.537 mmol) drop wise and stirred for 20 h. Reaction mixture was diluted with water, extracted with ethyl acetate washed with water, brine, dried over sodium sulfate and evaporated. Residue was chromatographed on silica gel using 20% ethyl acetate-petroleum ether to afford the title compound (0.2 g, 81%).

$^1$H NMR [200 MHz, CDCl$_3$]: δ 7.41-7.05 (m, 11H), 6.94 (d, J=8.3 Hz, 2H), 6.45-6.34 (m, 2H), 4.65 (d, J=5.4 Hz, 2H), 4.11 (q, J=6.8 Hz, 2H), 3.89 (dd, J=5.2 and 7.9 Hz, 1H), 3.68-3.46 (m, 1H), 3.35-3.19 (m, 1H), 3.13 (s, 3H), 3.02-2.85 (m, 2H), 1.18 (t, J=7.2 Hz, 3H), 1.06 (t, J=7.0 Hz, 3H).

Mass: m/z (CI): 552 (M$^+$+1, 100).

EXAMPLE 48

(S) 2-ethoxy-3-{4-[(E)-3-(4-methylsulfonyl-oxyphenyl)-2-propenyl(phenyl) carboxamido]phenyl}propionic Acid

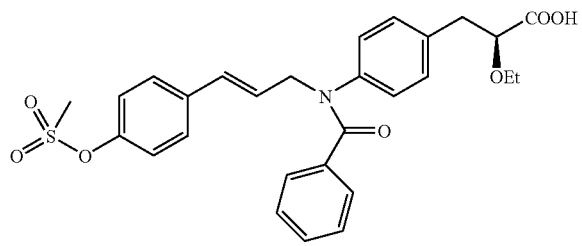

To a solution of (S) Ethyl 2-ethoxy-3-{4-[(E)-3-(4-methylsulfonyloxyphenyl)-2-propenyl(phenyl)carboxamido]phenyl}propanoate obtained in Example 47 (0.2 g, 0.363 mmol) in methanol (4 ml) was added a solution of sodium carbonate (0.192 g, 1.82 mmol) in water (2 ml) drop wise and stirred at RT for 72 h. Methanol was removed under reduced pressure. The residue was diluted with water and extracted with ethyl acetate. The aqueous layer was cooled to 0° C., acidified using 2N HCl up to pH ~2, extracted with ethyl acetate. The organic layer was washed with brine, dried over sodium sulfate and evaporated. Crude mass was chromatographed on silica gel using 2% methanol-chloroform to give the title compound (100 mg, 53%).

$^1$H NMR [200 MHz, CDCl$_3$]: δ 7.40-7.04 (m, 11H), 6.96 (d, J=8.3 Hz, 2H), 6.46-6.37 (m, 2H), 4.66 (d, J=5.6 Hz, 2H), 4.02-3.92 (m, 1H), 3.60-3.41 (m, 1H), 3.39-3.20 (m, 1H), 3.13 (s, 3H), 3.05-2.80 (m, 2H), 1.06 (t, J=7.0 Hz, 3H).

EXAMPLE 49

(S)-2-ethoxy-3-{4-[(E)-3-(4-methylsulfonyl-oxyphenyl)-2-propenyl(phenyl)carboxamido]phenyl}propionic Acid Magnesium Salt

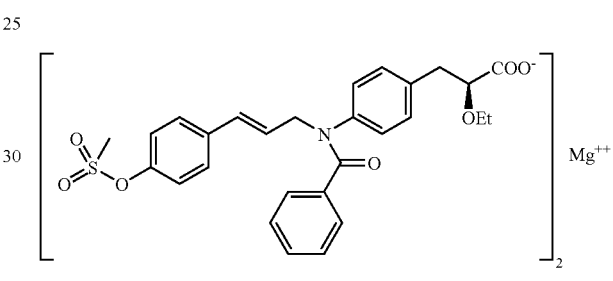

To a solution of (S) 2-ethoxy-3-{4-[(E)-3-(4-methylsulfonyl-oxyphenyl)-2-propenyl(phenyl) carboxamido]phenyl}propanoic acid obtained in Example 48 (70 mg, 0.134 mmol) in methanol (5 ml) was added magnesium hydroxide (4 mg, 0.065 mmol) and refluxed for overnight. Methanol was evaporated under reduced pressure, flushed twice with toluene and triturated with petroleum ether to obtain product as solid (65 mg, 89%); mp >250° C.

$^1$H NMR [200 MHz, CD$_3$OD]: δ 7.44 (d, J=8.6 Hz, 2H), 7.35-7.10 (m, 9H), 7.04 (d, J=8.1 Hz, 2H), 6.50-6.39 (m, 2H), 4.66 (d, J=5.4 Hz, 2H), 3.78-3.68 (m, 1H), 3.60-3.40 (m, 1H), 3.19 (s, 3H), 3.18-0.02 (m, 1H), 3.00-2.84 (m, 1H), 2.82-2.65 (m, 1H), 0.94 (t, J=7.0 Hz, 3H).

Mass: m/z (ES): 1069 (M$^+$, 24).

EXAMPLE 50

(S) Methyl 2-methoxy-3-{4-[(E)-3-(4-methyl-sulfonyloxyphenyl)-2-propenyl(phenyl)carboxamido]phenyl}propionate

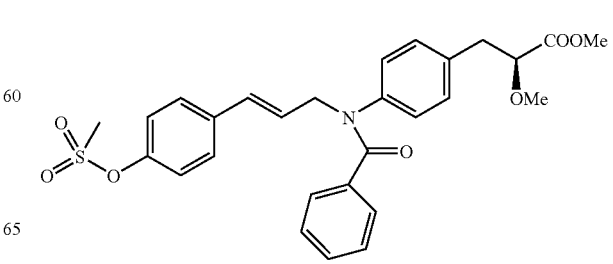

A solution of (S) Ethyl 2-methoxy-3-[4-{(E)-3-(4-methylsulfonyloxyphenyl)-2-propenylamino}phenyl]propionate obtained in Example 42 (0.650 g, 1.50 mmol) and potassium carbonate (0.621 g, 4.50 mmol) in dry DMF (10 ml) was stirred at RT for 20 min. Benzoyl chloride (0.21 ml, 1.80 mmol) was added drop wise and stirred at RT for 16 h. The reaction mixture was diluted with water and extracted with ethyl acetate washed with water, brine, dried over sodium sulfate and rotary evaporated to dryness. The residue was chromatographed on silica gel using 20% ethyl acetate-petroleum ether to afford the title compound (372 mg, 47%).

$^1$H NMR [200 MHz, CDCl$_3$]: δ 7.48-7.18 (m, 9H), 7.10 (d, J=8.3 Hz, 2H), 6.98 (d, J=8.3 Hz, 2H), 6.52-6.32 (m, 2H), 4.69 (d, J=5.4 Hz, 2H), 3.91 (t, J=6.4 Hz, 1H), 3.65 (s, 3H), 3.32 (s, 3H), 3.16 (s, 3H), 3.02-2.88 (m, 2H).

Mass: m/z (CI): 524 (M$^+$+1).

EXAMPLE 51

(S)-2-methoxy-3-{4-[(E)-3-(4-methylsulfonyl-oxyphenyl)-2-propenyl(phenyl)carboxamido]phenyl}propionic Acid

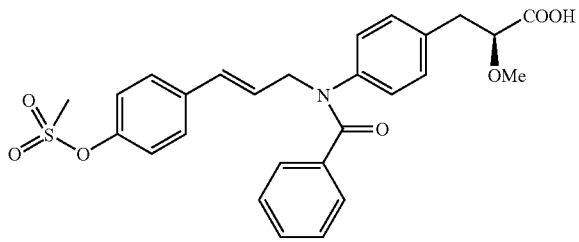

To a solution of (S) Methyl 2-methoxy-3-{4-[(E)-3-(4-methylsulfonyloxyphenyl)-2-propenyl(phenyl)carboxamido]phenyl}propanoate obtained in example 50(0.318 g, 0.608 mmol) in methanol (5 ml) was added a solution of sodium carbonate (0.322 g, 3.04 mmol) in water (1 ml) drop wise and stirred at RT for 18 h. Methanol was removed under reduced pressure and the residue was diluted with water and extracted with ethyl acetate. The aqueous layer was cooled to 0° C., acidified with 2N HCl up to pH ~2 and extracted with ethyl acetate. The organic layer was washed with water, brine, dried over sodium sulfate and concentrated. The residue was chromatographed on silica gel using 40% ethyl acetate-petroleum ether to give the title compound (220 mg, 73%).

$^1$H NMR [200 MHz, CDCl$_3$]: δ 7.44-7.20 (m, 7H), 7.16 (d, J=7.5 Hz, 2H), 7.08 (d, J=8.3 Hz, 2H), 6.96 (d, J=8.1 Hz, 2H), 6.50-6.28 (m, 2H), 4.66 (d, J=5.6 Hz, 2H), 3.92 (dd, J=4.2 and 7.4 Hz, 1H), 3.31 (s, 3H), 3.13 (s, 3H), 3.10-2.85 (m, 2H).

Mass: m/z (CI): 510 (M$^+$+1).

EXAMPLE 52

(S) 2-methoxy-3-{4-[(E)-3-(4-methylsulfonyl-oxyphenyl)-2-propenyl(phenyl)carboxamido]phenyl}propionic Acid and Magnesium Salt

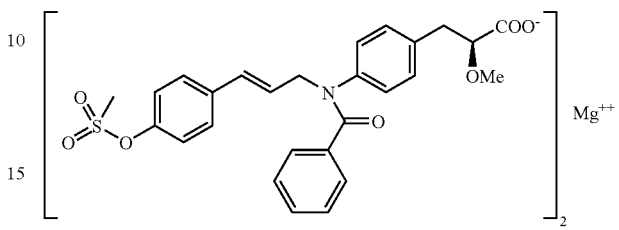

To a solution of (S)-2-methoxy-3-{4-[(E)-3-(4-methylsulfonyl-oxyphenyl)-2-propenyl(phenyl)carboxamido]phenyl}propanoic acid obtained in Example 51 (0.175 g, 0.354 mmol) in methanol (3 ml) was added magnesium hydroxide (10 mg, 0.175 mmol) and refluxed for 16 h. Methanol was removed under reduced pressure and flushed twice with toluene and the residue was triturated with petroleum ether to obtain the product (180 mg, 99%); mp >250° C.

$^1$H NMR [200 MHz, CD$_3$OD]: δ 7.40 (d, J=8.8 Hz, 2H), 7.36-6.96 (m, 11H), 6.44-6.24 (m, 2H), 4.62 (d, J=5.4 Hz, 2H), 3.27 (s, 3H), 3.16 (s, 3H), 3.12-2.99 (m, 2H).

Mass: m/z (ES): 1041 (M$^+$+1).

Demonstration of Efficacy of Compounds

A) In Vitro:

a) Determination of hPPARα activity Ligand binding domain of hPPARα was fused to DNA binding domain of Yeast transcription factor Gal 4 in eucaryotic expression vector. Using superfect (Qiagen, Germany) as transfecting reagent HEK-293 cells are transfected with this plasmid and a reporter plasmid harboring the luciferase gene driven by a GAL4 specific promoter. Compound can be added at different concentrations after 42 hrs of transfection and incubated overnight. Luciferase activity as a function of compound binding/activation capacity of PPARα will be measured using Packard Luclite kit (Packard, USA) in Top Count (Ivan Sadowski, Brendan Bell, Peter Broag and Melvyn Hollis. Gene. 1992. 118: 137-141; Superfect Transfection Reagent Handbook. February 1997. Qiagen, Germany).

b) Determination of hPPARγ activity Ligand binding domain of hPPARγ1 is fused to DNA binding domain of Yeast transcription factor GAL4 in eucaryotic expression vector. Using lipofectamine (Gibco BRL, USA) as transfecting reagent HEK-293 cells are transfected with this plasmid and a reporter plasmid harboring the luciferase gene driven by a GAL4 specific promoter. Compound can be added at 1 μM concentration after 48 hrs of transfection and incubated overnight. Luciferase activity as a function of drug binding/activation capacity of PPARγ1 will be measured using Packard Luclite kit (Packard, USA) in Packard Top Count (Ivan Sadowski, Brendan Bell, Peter Broag and Melvyn Hollis. Gene. 1992. 118: 137-141; Guide to Eukaryotic Transfections with Cationic Lipid Reagents. Life Technologies, GIBCO BRL, USA).

| Example No | Concentration | PPARα | Concentration | PPARγ |
|---|---|---|---|---|
| Example 14 | 50 μM | 9.4 | 1 μM | 0.7 |
| Example 15 | 50 μM | 6.1 | 1 μM | 0.7 |
| Example 27 | 50 μM | 8.5 | 1 μM | 0.8 | c) Determination of HMG CoA reductase inhibition activity Liver microsome bound reductase is prepared from 2% cholestyramine fed rats at mid-dark cycle. Spectrophotometric assays are carried out in 100 mM $KH_2PO_4$, 4 mM DTT, 0.2 mM NADPH, 0.3 mM HMG CoA and 125 μg of liver microsomal enzyme. Total reaction mixture volume was kept as 1 ml. Reaction was started by addition of HMG CoA. Reaction mixture is incubated at 37° C. for 30 min and decrease in absorbance at 340 nm was recorded. Reaction mixture without substrate was used as blank (Goldstein, J. L and Brown, M. S. Progress in understanding the LDL receptor and HMG CoA reductase, two membrane proteins that regulate the plasma cholesterol. J. Lipid Res. 1984, 25: 1450-1461). The test compounds will inhibit the HMG CoA reductase enzyme.

B) In Vivo a) Efficacy in genetic models Mutation in colonies of laboratory animals and different sensitivities to dietary regimens has made the development of animal models with non-insulin dependent diabetes and hyperlipidemia associated with obesity and insulin resistance possible. Genetic models such as db/db and ob/ob (Diabetes, (1982) 31(1): 1-6) mice and zucker fa/fa rats have been developed by the various laboratories for understanding the pathophysiology of disease and testing the efficacy of new antidiabetic compounds (Diabetes, (1983) 32: 830-838; Annu. Rep. Sankyo Res. Lab. (1994). 46: 1-57). The homozygous animals, C57 BL/KsJ-db/db mice developed by Jackson Laboratory, US, are obese, hyperglycemic, hyperinsulinemic and insulin resistant (J. Clin. Invest., (1990) 85: 962-967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention will be tested for blood sugar and triglycerides lowering activities.

Male C57BL/KsJ-db/db mice of 8 to 14 weeks age, having body weight range of 35 to 60 grams, bred at Dr. Reddy's Research Foundation (DRF) animal house, were used in the experiment. The mice are provided with standard feed (National Institute of Nutrition (NIN), Hyderabad, India) and acidified water, ad libitum. The animals having more than 350 mg/dl blood sugar will be used for testing. The number of animals in each group will be 4.

Test compounds are suspended on 0.25% carboxymethyl cellulose and administered to test group at a dose of 0.1 mg to 30 mg/kg through oral gavage daily for 6 days. The control group receives vehicle (dose 10 ml/kg). On 6th day the blood samples will be collected one hour after administration of test compounds/vehicle for assessing the biological activity.

The random blood sugar and triglyceride levels can be measured by collecting blood (100 μl) through orbital sinus, using heparinised capillary in tubes containing EDTA which was centrifuged to obtain plasma. The plasma glucose and triglyceride levels can be measured spectrometrically, by glucose oxidase and glycerol-3-$PO_4$ oxidase/peroxidase enzyme (Dr. Reddy's Lab. Diagnostic Division Kits, Hyderabad, India) methods respectively.

The blood sugar and triglycerides lowering activities of the test compound are calculated according to the formula.

| Compound | Dose (mg/kg) | Reduction in Blood Glucose Level (%) | Triglyceride Lowering (%) |
|---|---|---|---|
| Example 16 | 3 | 15 | 39 |
| Example 39 | 3 | 56 | 36 |
| Example 42 | 3 | 63 | 56 |

*results after 6 days b) Plasma triglyceride and Cholesterol lowering activity in hypercholesterolemic rat models Male Sprague Dawley rats (NIN stock) were bred in DRF animal house. Animals were maintained under 12 hour light and dark cycle at 25±1° C. Rats of 180-200 gram body weight range were used for the experiment. Animals are made hypercholesterolemic by feeding 2% cholesterol and 1% sodium cholate mixed with standard laboratory chow [National Institute of Nutrition (NIN), Hyderabad, India] for 6 days. Throughout the experimental period the animals were maintained on the same diet (Petit, D., Bonnefis, M. T., Rey, C and Infante, R. Effects of ciprofibrate on liver lipids and lipoprotein synthesis in normo- and hyperlipidemic rats. Atherosclerosis. 1988. 74: 215-225).

The test compounds can be administered orally at a dose 0.1 to 30 mg/kg/day for 3 days. Control group was treated with vehicle alone (0.25% Carboxymethylcellulose; dose 10 ml/kg).

The blood samples can be collected in fed state 1 hour after drug administration on 0 and 3 day of compound treatment. The blood can be collected from the retro-orbital sinus through heparinised capillary in EDTA containing tubes. After centrifugation, plasma sample will be separated for total cholesterol, HDL and triglyceride estimations. Measurement of plasma triglyceride, total cholesterol and HDL were done using commercial kits (Dr. Reddy's Laboratory, Diagnostic Division, India). LDL and VLDL cholesterol can be calculated from the data obtained for total cholesterol, HDL and triglyceride. The reductions of various parameters examined are calculated according to the formula.

| Compound | Dose (mg/kg) | Reduction in Total Cholesterol (%) | Triglyceride Lowering (%) | Increase in High Density Liproprotien (%) | Reduction in Low Density Liproprotein (%) |
|---|---|---|---|---|---|
| Example 43 | 1 | 53 | 55 | 77 | 56 |

*results after 3 days c) Plasma triglyceride and total cholesterol lowering activity in Swiss albino mice Male Swiss albino mice (SAM) were obtained from NIN and housed in DRF animal house. All these animals are maintained under 12 hour light and dark cycle at 25±1° C. Animals are given standard laboratory chow (NIN, Hyderabad, India) and water, ad libitum. SAM of 20-25 g body weight range and Guinea pigs of 500-700 g body weight range are used (Oliver, P., Plancke, M. O., Marzin, D., Clavey, V., Sauzieres, J and Fruchart, J. C. Effects of fenofibrate, gemfibrozil and nicotinic acid on plasma lipoprotein levels in normal and hyperlipidemic mice. Atherosclerosis. 1988. 70: 107-114).

The test compounds can be administered orally to Swiss albino mice at 0.3 to 30 mg/kg/day dose for 6 days. Control mice are treated with vehicle (0.25% Carboxymethylcellulose; dose 10 ml/kg). The test compounds are administered orally to Guinea pigs at 0.3 to 30 mg/kg/day dose for 6 days. Control animals are treated with vehicle (0.25% Carboxymethylcellulose; dose 5 ml/kg). The blood samples can be collected in fed state 1 hour after drug administration on 0 and 6 day of treatment. The blood can be collected from the retro-orbital sinus through heparinised capillary in EDTA containing tubes. After centrifugation, plasma sample was separated for triglyceride (Wieland, O. Methods of Enzymatic analysis. Bergermeyer, H. O., Ed., 1963. 211-214; Trinder, P. Ann. Clin. Biochem. 1969. 6: 24-27). Measurement of plasma triglyceride is done using commercial kits (Dr. Reddy's Diagnostic Division, Hyderabad, India).

| Compound | Dose (mg/kg) | Triglyceride Lowering (%) |
| --- | --- | --- |
| Example 19 | 1 | 39 |
| Example 30 | 3 | 41 |
| Example 38 | 1 | 41 |

*results after 6 days d) Body weight reducing effect in cholesterol fed hamsters: Male Syrian Hamsters are procured from NIN, Hyderabad, India. Animals are housed at DRF animal house under 12 hour light and dark cycle at 25+1° C. with free access to food and water. Animals are maintained with 1% cholesterol containing standard laboratory chow (NIN) from the day of treatment.

The test compounds can be administered orally at 1 to 30 mg/kg/day dose for 15 days. Control group animals are treated with vehicle (Mill Q water, dose 10 ml/kg/day). Body weights are measured on every $3^{rd}$ day.

| | Dose (mg/kg) | Reduction in Total Cholesterol (%) | Reduction in Triglyceride (%) | Reduction in Body weight (%) |
| --- | --- | --- | --- | --- |
| Compound Example 16 | 3 | 63 | 77 | 19 |

Formulae for Calculation:
1. Percent reduction in Blood sugar/triglycerides/total cholesterol will be calculated according to the formula:

$$\text{Percent reduction (\%)} = \left[1 - \frac{TT/OT}{TC/OC}\right] \times 100$$

OC=Zero day control group value
OT=Zero day treated group value
TC=Test day control group value
TT=Test day treated group value 2. LDL and VLDL cholesterol levels will be calculated according to the formula:

LDL cholesterol in mg/dl =

$$\left[\text{Total } cholesterol - HDL \text{ cholesterol} - \frac{\text{Triglyceride}}{5}\right] \text{mg/dl}$$

VLDL cholesterol in mg/dl=[Total cholesterol−HDL cholesterol−LDL cholesterol]mg/dl.

What is claimed is:
1. A compound of the formula (I)

wherein $R^1$ represents hydrogen, hydroxy, halogen, linear or branched $(C_1-C_{12})$ alkyl, linear or branched $(C_1-C_{12})$ alkoxy, or substituted or unsubstituted arylalkyl;

$R^2$ represents hydrogen, halogen, linear or branched $(C_1-C_{12})$ alkyl, linear or branched $(C_1-C_{12})$ alkoxy, $(C_1-C_{12})$ alkanoyl, aroyl, arylalkanoyl, or substituted or unsubstituted arylalkyl;

$R^3$ represents hydrogen or a substituted or unsubstituted group which is linear or branched $(C_1-C_{12})$alkyl, cycloalkyl, cycloalkylalkyl, cycloalkenyl, aryl, $(C_1-C_{12})$alkanoyl, aroyl, arylalkyl, arylalkanoyl, alkoxyalkyl, alkoxycarbonyl, aryloxycarbonyl, alkylaminocarbonyl, or arylaminocarbonyl;

$R^4$ represents hydrogen;

Y represents oxygen;

$R^5$ represents hydrogen or a substituted or unsubstituted group which is alkyl, alkenyl, cycloalkyl, cycloalkylalkyl, aryl or arylalkyl;

Ar represents substituted or unsubstituted group which is divalent phenylene, or naphthylene;

X represents a bond;

$R^6$ represents $-OSO_2R^8$, $-SO_2R^8$, $-SOR^8$, $-SR^8$, $-SO_2NR^8R^9$, or $-SO_2OR^8$, wherein $R^8$ and $R^9$ which may be the same or different, independently represent hydrogen, substituted or unsubstituted alkyl, aryl, arylalkyl, alkoxycarbonyl or arylalkoxycarbonyl; or with the provisio that $R^6$ is hydrogen, when $R^{13}$ is at the third position of the phenyl ring and does not represent hydrogen;

$R^{13}$ represents hydrogen, $-OSO_2R^8$, $-SO_2R^8$, $-SOR^8$, $-SR^8$, $-SO_2NR^8R^9$, $-SO_2OR^8$, wherein $R^8$ and $R^9$, which may be the same or different, independently represent hydrogen, substituted or unsubstituted alkyl, aryl, arylalkyl, alkoxycarbonyl or arylalkoxycarbonyl;

n is 1 to 6, and m is 0 to 6;

and stereoisomers, tautomeric forms, pharmaceutically acceptable salts, and pharmaceutically acceptable solvates of the compound of the formula (I).

2. The compound of formula (I) as claimed in claim 1, wherein:
$R^1$ is hydrogen or linear or branched $(C_1$-$C_6)$alkyl;
$R^2$ is hydrogen or linear or branched $(C_1$-$C_6)$alkyl;
$R^3$ is hydrogen, linear or branched $(C_1$-$C_{12})$alkyl, $(C_3$-$C_7)$cycloalkyl, aryl or arylalkyl;
$R^4$ hydrogen;
$R^5$ is hydrogen, $(C_1$-$C_{12})$alkyl or $(C_3$-$C_7)$cycloalkyl;
$R^6$ is —$OSO_2R^8$;
$R^8$ is hydrogen, linear or branched $(C_1$-$C_6)$alkyl or substituted or unsubstituted aryl;
$R^9$ is hydrogen, linear or branched $(C_1$-$C_6)$alkyl;
$R^{13}$ is hydrogen or —$OSO_2R^8$;
X represents a bond;
Y is oxygen;
m is an integer from 0 to 1; and
n is an integer from 1 to 2.

3. The compound of formula (I) as claimed in claim 2, wherein
$R^1$ is hydrogen;
$R^2$ is hydrogen;
$R^3$ is hydrogen, or linear or branched $(C_1$-$C_{12})$alkyl;
$R^4$ is hydrogen;
$R^5$ is hydrogen or $(C_1$-$C_{12})$alkyl;
$R^6$ is —$OSO_2R^8$;
$R^8$ is or linear or branched $(C_1$-$C_6)$alkyl, or substituted aryl group wherein the substituent is linear or branched $(C_1$-$C_6)$alkyl;
$R^9$ is linear or branched $(C_1$-$C_6)$alkyl;
$R^{13}$ is hydrogen or —$OSO_2R^8$; and
X represents a bond.

4. The compound according to claim 1, wherein the pharmaceutically acceptable salt is selected from the group consisting of Li, Na, K, Ca, Mg, Fe, Cu, Zn, Al, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, theobromine, valinol, diethylamine, triethylamine, trimethylamine, tripropylamine, tromethamine, adamentyl amine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, pyrimidine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; salts of acidic amino acids selected from aspartic acid or glutamic acid; guanidine, substituted guanidine wherein the substituents are selected from nitro, amino, alkyl, alkenyl or alkynyl; ammonium, substituted ammonium salts; sulphates, nitrates, phosphates, perchlorates, borates, hydrohalides (HCl, HBr, HI), acetates, tartrates, maleates, citrates, succinates, palmoates, methanesulphonates, benzoates, salicylates, hydroxynaphthoates, benzenesulfonates, ascorbates, glycerophosphates, or ketoglutarate salt.

5. The compound according to claim 1, wherein the substituent on the group represented by $R^3$ is selected from the group consisting of hydrogen linear or branched groups selected from $(C_1$-$C_{12})$alkyl, $(C_3$-$C_7)$cycloalkyl, aryl or arylalkyl.

6. The compound according to claim 1, wherein the substituent on the group represented by $R^5$ is selected from the group consisting of hydrogen linear or branched groups selected from $(C_1$-$C_{12})$alkyl, or $(C_3$-$C_7)$cycloalkyl.

7. The compound according to claim 1, wherein the substituent on the group represented by $R^6$ is —$OSO_2R^8$.

8. The compound according to claim 1, wherein the substituents on the group represented by $R^{13}$ are selected from the group consisting of hydrogen or —$OSO_2R^8$.

9. The compound according to claim 1, wherein the substituents on the groups represented by, $R^8$ or $R^9$ are selected from the group consisting of hydrogen, linear or branched $(C_1$-$C_6)$alkyl, or substituted or unsubstituted aryl group wherein the substituent is linear or branched $(C_1$-$C_6)$ alkyl.

10. A composition comprising a) the compound of claim 1 in accordance with the formula (I) its pharmaceutically acceptable salts, or its pharmaceutically acceptable solvates, and b) a pharmaceutically acceptable carrier, diluent, or excipients.

11. The composition of claim 10, wherein, for said compound, said salt or said solvate,
$R^1$ is hydrogen, linear or branched $(C_1$-$C_6)$alkyl;
$R^2$ is hydrogen, linear or branched $(C_1$-$C_6)$alkyl;
$R^3$ is hydrogen, linear or branched $(C_1$-$C_{12})$alkyl, $(C_1$-$C_7)$cycloalkyl;
$R^4$ is hydrogen;
$R^5$ is hydrogen, $(C_1$-$C_{12})$alkyl or $(C_3$-$C_7)$cycloalkyl;
$R^6$ is —$OSO_2R^8$;
$R^8$ is hydrogen, linear or branched $(C_1$-$C_6)$alkyl or substituted or unsubstituted aryl;
$R^9$ is hydrogen, linear or branched $(C_1$-$C_6)$alkyl, t-butyloxycarbonyl or benzyloxycarbonyl;
$R^{13}$ is hydrogen or —$OSO_2R^8$;
X represents a bond;
Y is oxygen;
m is an integer from 0 to 1; and
n is an integer from 1 to 2.

12. The composition of claim 10, wherein
$R^1$ hydrogen;
$R^2$ is hydrogen;
$R^3$ is hydrogen, or linear or branched $(C_1$-$C_{12})$alkyl;
$R^4$ is hydrogen;
$R^5$ hydrogen or $(C_1$-$C_{12})$alkyl;
$R^6$ is —$OSO_2R^8$;
$R^8$ is or linear or branched $(C_1$-$C_6)$alkyl, or substituted aryl group wherein the substituent is linear or branched $(C_1$-$C_6)$alkyl;
$R^9$ is linear or branched $(C_1$-$C_6)$alkyl, t-butyloxycarbonyl or benzyloxycarbonyl;
$R^{13}$ is hydrogen or —$OSO_2R^8$; and
X represents a bond.

13. The composition of claim 10, which is in the form of a tablet, capsule, powder, syrup, solution or suspension.

14. The composition of claim 10, further comprising insulin.

* * * * *